US005990386A

United States Patent [19]

An

[11] Patent Number: 5,990,386
[45] Date of Patent: Nov. 23, 1999

[54] GENES CONTROLLING FLORAL DEVELOPMENT AND APICAL DOMINANCE IN PLANTS

[75] Inventor: Gynhueng An, Pohang, Rep. of Korea

[73] Assignee: Washington State University Research Foundation, Pullman, Wash.

[21] Appl. No.: 08/867,087

[22] Filed: Jun. 2, 1997

Related U.S. Application Data

[63] Continuation-in-part of application No. 08/485,981, Jun. 7, 1995, Pat. No. 5,861,542, which is a continuation-in-part of application No. 08/323,449, Oct. 14, 1994, Pat. No. 5,859,326.

[51] Int. Cl.$^6$ .......................... C12N 15/82; C12N 15/29; C12N 5/04; A01H 5/00
[52] U.S. Cl. ...................... 800/290; 800/278; 800/298; 435/419; 435/468; 536/23.6
[58] Field of Search ........................ 536/23.6; 800/278, 800/290, 298; 435/468, 419

[56] References Cited

FOREIGN PATENT DOCUMENTS

WO 96 11566  4/1996  WIPO .

OTHER PUBLICATIONS

Mena et al. Plant J 8(6): 845 854, 1995.
Lu et al. Plant Mol. Biol. 23:901–904, 1993.
Matsuoka et al. Plant Cell 5:1039–1048, Sep. 1993.
Kang and An, "Isolation and Characterization of a Rice MADS Box Gene Belonging to the AGL2 Gene Family," Mol. Cells 7:45–51 (1997).
Kang et al., "Phenotypic alterations of petal and sepal by ectopic expression of a rice MADS box gene in tobacco," Plant Molecular Biology, 29:1–10 (1995).
Chung et al., "Characterization of two rice MADS box genes homologous to GLOBOSA," Plant Science 109:45–56 (1995).
Greco et al., "MADS box genes expressed in developing inflorescences of rice and sorghum," Mol. Gen. Genet. 253:615–623 (1997).
Ma et al., "AGL1–AGL6, an Arabidopsis Gene Family With Similarity to Floral Homeotic and Transcription Factor Genes," Genes Dev. 5:484–495 (1991).
Huijser et al., "Bracteomania, and Inflorescence Anomaly, is Caused by the Loss of Function of the MADS–Box Gene squamosa in Antirrhinum majus," EMBO J. 11:1239–1249 (1992).
Schwarz–Sommer et al., "Characterization of the Antirrhinum Floral Homeotic MADS–Box Gene deficiens: Evidence for DNA Binding and Autoregulation of its Persistent Expression Through Flower Development," EMBO J. 11:251–263 (1992).
Bradley et al., "Complementary Floral Homeotic Phenotypes Result From Opposite Orientations of a Transposon at the plena Locus of Antirrhinum," Cell 72:85–95 (1993).

Kempin et al., "Conversion of Perianth into Reproductive Organs by Ectopic Expression of the Tobacco Floral Homeotic Gene NAGI," Plant Physiol. 103:1041–1046 (1993).
Sommer et al., "Deficiens, a Homeotic Gene Involved in the Control of Flower Morphogenesis in Antirrhinum majus: The Protein Shows Homology to Transcription Factors," EMBO J. 9:605–613 (1990).
Angenent et al., "Differential Expression of Two MADS Box Genes in Wild–Type and Mutant Petunia Flowers," Plant Cell 4:983–993 (1992).
Chung et al., "Early Flowering and Reduced Apical Dominance Result from Ectopic Expression of a Rice MADS Box Gene," Plant Mol. Biol. 0:1–9 (1994).
Tsuchimoto et al., "Ectopic Expression of pMADS3 in Transgenic Petunia Phenocopies the Petunia blind Mutant," Plant Cell 5:843–853 (1993).
Coen et al., "floricaula: A Homeotic Gene Required for Flower Development in Antirrhinum majus," Cell 63:1311–1322 (1990).
Trobner et al., "GLOBOSA: A Homeotic Gene Which Interacts With Deficiens in the Control of Antirrhinum Floral Organogenesis," EMBO J. 11:4693–4704 (1992).
Jack et al., "The Homeotic Gene APETALA3 of Arabidopsis thaliana Encodes a MADS Box and is Expressed in Petals and Stamens," Cell 68:683–697 (1992).
Tamas, "Hormonal Regulation of Apical Dominance." In: Davies PJ (ed), Plant Hormones and Their Role in Plant Growth and Development, pp. 393–410. Martinus Nijhoff Pub., Dordrecht, Netherlands (1987).
Schmidt et al., "Identification and Molecular Characterization of ZAG1, the Maize Homolog of the Arabidopsis Floral Homeotic Gene Agamous," Plant Cell 5:729–737 (1993).
Pnueli et al., "Isolation of the Tomato Agamous Gene TAG1 and Analysis of its Homeotic Role in Transgenic Plants," Plant Cell 6:163–173 (1994).
Weigel et al., "Leafy Controls Floral Meristem Identity in Arabidopsis," Cell 69:843–859 (1992).
Mandel et al., "Molecular Characterization of the Arabidopsis Floral Homeotic Gene APETALA1," Nature 360:273–277 (1992).
Pnueli et al., "The MADS Box Gene Family in Tomato: Temporal Expression During Floral Development, Conserved Secondary Structures and Homology with Homeotic Genes From Antirrhinum and Arabidopsis," Plant J. 1:255–266 (1991).

(List continued on next page.)

Primary Examiner—David T. Fox
Attorney, Agent, or Firm—Klarquist Sparkman Campbell Leigh & Whinston, LLP

[57] ABSTRACT

The present invention provides compositions and methods for affecting the transition from vegetative to reproductive growth in a wide variety of plants. Several MADS-box genes have been isolated that, when expressed in transgenic plants, result in such phenotypes as, for example, reduced apical dominance or dwarfism and early flowering.

33 Claims, 12 Drawing Sheets

OTHER PUBLICATIONS

Mandel et al., "Manipulation of Flower Structure in Transgenic Tobacco," *Cell* 71:133–143 (1992).

Gasser, "Molecular Studies on the Differentiation of Floral Organs," *Annu. Rev. Plant Physiol. Plant Mol. Biol.* 42:621–649 (1991).

Yanofsky et al., "The Protein Encoded by the Arabidopsis Homeotic Gene agamous Resembles Transcription Factors," *Nature* 346:35–39 (1990).

An, "Regulatory Genes Controlling Flowering Time or Floral Organ Development," *Plant Mol. Biol.* 25:335–337 (1994).

Coen, "The Role of Homeotic Genes in Flower Development and Evolution," *Annu. Rev. Plant Physiol. Plant Mol. Biol.* 42:241–279 (1991).

Pnueli et al., "The TM5 MADS Box Gene Mediates Organ Differentiation in Three Inner Whorls of Tomato Flowers," *Plant Cell* 6:175–186 (1994).

Mizukami et al., "Ectopic Expression of the Floral Homeotic Gene Agamous in Transgenic Arabidopsis Plants Alters Floral Organ Identity," *Cell* 71:119–131 (1992).

Coupland, "Leafy Blooms in Aspen," *Nature* 377:482–483 (1995).

Weigel et al., "A Developmental Switch Sufficient for Flower Initiation in Diverse Plants," *Nature* 377:495–500 (1995).

Mandel et al., "A Gene Triggering Flower Formation in Arabidopsis," *Nature* 377:522–524 (1995).

Kang and An, "AC U78782" EMBL Database, Jul. 31, 1997, Heidelberg.

Theissen and Heinz, "MADS–Box Gene in Plant Ontogeny and Phylogeny: Haeckel' 'Biogenetic Law' Revisited," *Current Opinion in Genetics and Development* 5:628–639 (1995).

```
   1  AAAACTAGCTTGCAAAGGGGATAGAGTAGTAGAGAGAGAGAGAGAGGAGAGGAGGAGGAA

61  GAAGATGGGGAGGGGGAAGGTGGAGCTGAAGCGGATCGAGAACAAGATCAGCCGGCAGGT
           MetGlyArgGlyLysValGluLeuLysArgIleGluAsnLysIleSerArgGlnVa    19
                                                                   MADS BOX
 121  GACGTTCGCCAAGCGCAGGAACGGCCTGCTCAAGAAGGCCTACGAGCTCTCCCTCCTCTG
      lThrPheAlaLysArgArgAsnGlyLeuLeuLysLysAlaTyrGluLeuSerLeuLeuCy    39

181  CGACGCCGAGGTCGCCCTCATCATCTTCTCCGGCCGCGGCCGCCTCTTCGAGTTCTCCAG
      sAspAlaGluValAlaLeuIleIlePheSerGlyArgGlyArgLeuPheGluPheSerSe    59

241  CTCATCATGCATGTACAAAACCTTGGAGAGGTACCGCAGCTGCAACTACAACTCACAGGA
      rSerSerCysMetTyrLysThrLeuGluArgTyrArgSerCysAsnTyrAsnSerGlnAs    79

301  TGCAGCAGCTCCAGAAAACGAAATTAATTACCAAGAATACCTGAAGCTGAAAACAAGAGT
      pAlaAlaAlaProGluAsnGluIleAsnTyrGlnGluTyrLeuLysLeuLysThrArgVa    99

361  TGAATTTCTTCAAACCACACAGAGAAATATTCTTGGTGAGGATTTGGGCCCACTAAGCAT
      lGluPheLeuGlnThrThrGlnArgAsnIleLeuGlyGluAspLeuGlyProLeuSerMe   119
                                                                   K BOX
 421  GAAGGAGCTGGAGCAGCTTGAGAACCAGATAGAAGTATCCCTCAAACAAATCAGGTCAAG
      tLysGluLeuGluGlnLeuGluAsnGlnIleGluValSerLeuLysGlnIleArgSerAr   139

481  AAAGAACCAAGCACTGCTTGATCAGCTGTTTGATCTGAAGAGCAAGGAGCAACAGCTGCA
      gLysAsnGlnAlaLeuLeuAspGlnLeuPheAspLeuLysSerLysGluGlnGlnLeuGl   159

541  AGATCTCAACAAAGACTTGAGGAAAAAGTTACAGGAAACCAGTGCAGAGAATGTGCTCCA
      nAspLeuAsnLysAspLeuArgLysLysLeuGlnGluThrSerAlaGluAsnValLeuHi   179

601  TATGTCCTGGCAAGATGGTGGTGGGCACAGCGGTTCTAGCACTGTTCTTGCTGATCAGCC
      sMetSerTrpGlnAspGlyGlyGlyHisSerGlySerSerThrValLeuAlaAspGlnPr   199

661  TCATCACCATCAGGGTCTTCTCCACCCTCACCCAGATCAGGGTGACCATTCCCTGCAGAT
      oHisHisHisGlnGlyLeuLeuHisProHisProAspGlnGlyAspHisSerLeuGlnIl   219

721  TGGGTATCATCACCCTCATGCTCACCATCACCAGGCCTACATGGACCATCTGAGCAATGA
      eGlyTyrHisHisProHisAlaHisHisHisGlnAlaTyrMetAspHisLeuSerAsnGl   239

781  AGCAGCAGACATGGTTGCTCATCACCCCAATGAACACATCCCATCCGGCTGGATATGATG
      uAlaAlaAspMetValAlaHisHisProAsnGluHisIleProSerGlyTrpIle***    257

841  TGTGTGTTCAGTTCAGGCTTCAGGCTTCAGAGAAGCCAATGCAAACAGTGTCCTGTAATC

901  CAGTAATTACAGGGCATATGTAATGTAATGTAATGTAATCCCTGATCTATATTTTGCTAA

961  GTACGTGCGTGCTCTCTTACGACCTTCTCCCCAAACAGTTAATCAGGGGAATAATAATT

1021  TCGTTTGATGCACGTACTGTATGTCTGTATCTGTCACTGTATCGTAGGACCGTCCATGTA

1081  TAACAATTTCCGTTTTGGATGTGGTAACAATTAATTGGCACTTAAATTTATATTTGTGAT

```
GRGKVELKRIENKISRQVTFAKRRNGLLKKAYELSLLCDAEVALIIFSGRGRLFEF          OsMADS1

***R*Q********N*****S***A******H*I*V********VV**HK*K***Y          Ap1
*****Q********N*****S***G******H***V**********V**NK*K***Y         SQUA

****I*I****TTN*C**************V******VS****Y*Y    AG
****I*I****ITN*C**************V*****VVS****Y*Y    PLE

*G*R*Q****QTNYS**F*HTV**R*SI*M**SSNK*H*Y           Ap3
A***IQI*****QTN****YS******F***H***V****K*SI*MI*STQK*H*Y           DEF A
```

FIG. 1B

```
  1 CCGGCCGCTGAGAAAAATGGGAAGGGGTAGGGTTGAGCTTAAGAGAATAGAGAACAAGATC        15
                   M  G  R  G  R  V  E  L  K  R  I  E  N  K  I
 61 AACAGGCAAGTGACCTTCGCTAAGAGAAATGGACTTTTGAAAAAAGCTTATGAGCTT           35
     N  R  Q  V  T  F  A  K  R  R  N  G  L  L  K  K  A  Y  E  L
121 TCTGTTCTTTGTGATGCTGAGGTTGCTCTCATCTTCTCCAATAGGGAAAACTGTAC            55
     S  V  L  C  D  A  E  V  A  L  I  I  F  S  N  R  G  K  L  Y
181 GAGTTCTGCAGTAGCTCTAGCATGCTCAAGACATTAGAGAGGTACCAGAAGTGCAACTAC        75
     E  F  C  S  S  S  M  L  K  T  L  E  R  Y  Q  K  C  N  Y
241 GGAGCACCAGAGACCAATATATCCACACGAGAAGCACTGAAATAAGTAGCCAACAAGAA         95
     G  A  P  E  T  N  I  S  T  R  E  A  L  E  I  S  S  Q  Q  E
301 TACTTGAAGCTTAAAGCACGTTACGAAGCATTACAGCGATCACAGAGAAATCTTCTTTGGT      115
     Y  L  K  L  K  A  R  Y  E  A  L  Q  R  S  Q  R  N  L  L  G
361 GAAGATCTTGGCCCCTTTGAATAGCAAGGAACTTGAATCACTTGAGAGGCAGCTTGATATG      135
     E  D  L  G  P  L  N  S  K  E  L  E  S  L  E  R  Q  L  D  M
421 TCACTGAAACAGATTCGATCAACTCGGACTCAGTTAATGTTGGATCAACTTACAGATCTT      155
     S  L  K  Q  I  R  S  T  R  T  Q  L  M  L  D  Q  L  T  D  L
481 CAGAGAAGGAACATGCATTAAACGAACGCAAACAGAACCTTGAAACAAAGGTTGATGGAA      175
     Q  R  K  E  H  A  L  N  E  A  N  R  T  L  K  Q  R  L  M  E
541 GGAAGCCAACTAAATCTGCAGTGGCAACAAAATGCACAAGATATGGCTACGCCGCAA         195
     G  S  Q  L  N  L  Q  W  Q  Q  N  A  Q  D  M  G  Y  G  R  Q
601 ACAACTCAAACTCAGGGCGATGGCTTTTTCATCCTTTGGAATGTGAACCCACTTTGCAA       215
     T  T  Q  T  Q  G  D  G  F  F  H  P  L  E  C  E  P  T  L  Q
661 ATTGGGTATCAGAATGATCCAATAACAGTAGGAGGAGCAGGGCCCAGTGTGAATAACTAC      235
     I  G  Y  Q  N  D  P  I  T  V  G  G  A  G  P  S  V  N  N  Y
721 ATGGCTGGTTGCCTTGAAATTAAGCTCATTTCCGATAAGATTGATTATATAAACAT          241
     M  A  G  W  L  P  *
781 ATGCTCAATGTTTTCCTATCATAAACACTCTCCTAATTTGTGTTATATGTTGTTGCCG
841 AATTCTGGACTAATTTGGGATCCATAAGACAGACCCGTTATTGTTACTTAATCATAAACT
901 AGATTTCCCTGAGTGACTAATCACTAAAGCTTATTACTTTCCTCC(A)
```

FIG. 2

```
Nt    1  MGRGRVELKRIENKINRQVTFAKRRNGLLKKAYELSVLCDAEVALIIFSN                          50
         |||| |||||||||| |:||||||||||||||||||||:|||||||||
Os    1  MGRGKVELKRIENKISRQVTFAKRRNGLLKKAYELSLLCDAEVALIIFSG                          50

51  RGKLYEFCSSSSMLKTLERYQKCNYGAPETNISTREALEISSQQEYLKLK                          100
         ||:|:||.||||.|||||||:.|.||..      .|.:||||||||
     51  RGRLFEFSSSSCMYKTLERYRSCNYNSQDAAAPENEI......NYQEYLKLK                        96

101  ARYEALQRSQRNLLGEDLGPLNSKELESLERQLDMSLKQIRSTRTQLMLD                          150
         .|.||.|| :|||||||||||.|||||||:.|:|||:|||:.||||.||
     97  TRVEFLQTTQRNILGEDLGPLSMKELEQLENQIEVSLKQIRSRKNQALLD                          146

151  QLTDLQRKEHALNEANRTLKQRLMEGSQ...LNLQWQQNAQDMG.....YG                         193
         ||.|||::|: |.: |:||:||:|..:        |.:    :  |.
    147  QLFDLKSKEQQLQDLNKDLRKKLQETSAENVLHMSWQDGGGHSGSSTVLA                          196

194  RQTTQTQGDGFFHPLECEPTLQIGYQNDPI...........TVGGAGPSVNN                        234
         ..|.|: ||.: ||  |  :.|:||::|::            ::  .|:
    197  DQPHHHQGLLHPHPDQGDHSLQIGYHHPHAHHHQAYMDHLSNEAADMVAH                          246

235  YMAGWLP 241
         :  :: |
    247  HPNEHIP 253
```

FIG. 3

```
   1 TACCCGCGGGAATCGTTCGATCGATCGGGCGAGATGGGGAGGGGAAGAGTTGAGCTGAAG
                                       M  G  R  G  R  V  E  L  K     9

61 CGCATCGAGAACAAGATCAACAGGCAGGTCACCTTCTCCAAGCGCCGCAACGGCCTCCTC
      R  I  E  N  K  I  N  R  Q  V  T  F  S  K  R  R  N  G  L  L    29
                                                                   MADS BOX
 121 AAGAAGGCCTACGAGCTGTCCGTTCTCTGCGACGCCGAGGTCGCGCTCATCATCTTCTCC
      K  K  A  Y  E  L  S  V  L  C  D  A  E  V  A  L  I  I  F  S    49

181 AGCCGCGGCAAGCTCTACGAGTTCGGCAGCGCCGGCATAACAAAGACTTTAGAAAGGTAC
      K  S  R  G  L  Y  E  F  G  S  A  G  I  T  K  T  L  E  R  Y    69

241 CAACATTGTTGCTACAATGCTCAAGATTCCAACAATGCACTTTCTGAAACTCAGAGTTGG
      Q  H  C  C  Y  N  A  Q  D  S  N  N  A  L  S  E  T  Q  S  W    89

301 TACCATGAAATGTCAAAGTTGAAAGCAAAATTTGAAGCTTTGCAGCGCACTCAAAGGCAC
      Y  H  E  M  S  K  L  K  A  K  F  E  A  L  Q  R  T  Q  R  H   109
                                                                    K BOX
 361 TTGCTTGGGGAGGATCTTGGACCACTCAGCGTCAAAGAATTGCAGCAGCTGGAGAAACAG
      L  L  G  E  D  L  G  P  L  S  V  K  E  L  Q  Q  L  E  K  Q   129

421 CTTGAATGTGCACTATCACAGGCGAGACAGAGAAAGACGCAACTGATGATGGAACAGGTG
      L  E  C  A  L  S  Q  A  R  Q  R  K  T  Q  L  M  M  E  Q  V   149

481 GAGGAACTTCGCAGAAAGGAGCGTCAGCTGGGTGAAATTAATAGGCAACTCAAGCACAAG
      E  E  L  R  R  K  E  R  Q  L  G  E  I  N  R  Q  L  K  H  K   169

541 CTCGAGGTTGAAGGTTCCACCAGCAACTACAGAGCCATGCAGCAAGCCTCCTGGGCTCAG
      L  E  V  E  G  S  T  S  N  Y  R  A  M  Q  Q  A  S  W  A  Q   189

601 GGCGCCGTGGTGGAGAATGGCGCCGCATACGTGCAGCCGCCGCCACACTCCGCGGCCATG
      G  A  V  V  E  N  G  A  A  Y  V  Q  P  P  P  H  S  A  A  M   209

661 GACTCTGAACCCACCTTGCAAATTGGGTATCCTCATCAATTTGTGCCTGCTGAAGCAAAC
      D  S  E  P  T  L  Q  I  G  Y  P  H  Q  F  V  P  A  E  A  N   229

721 ACTATTCAGAGGAGCACTGCCCCTGCAGGTGCAGAGAACAACTTCATGCTGGGATGGGTT
      T  I  Q  R  S  T  A  P  A  G  A  E  N  N  F  M  L  G  W  V   249

781 CTTTGAGCTAAGCAGCCATCGATCAGCTGTCAGAAGTTGGAGCTAATAATAAAAGGGATG
      L  *                                                          250
 841 TGGAGTGGGCTACATGTATCTCGGATCTCTCTGCGAGCCACCTAATGGTCTTGCGTGGCC
 901 CTTTAATCTGTATGTTTTTGTGTGTAAGCTACTGCTAGCTGTTTGCACCTTCTGCGTCCG
 961 TGGTTGTGTTTCCGTGCTACCTTTTTATGTTTTGATTTGGATCTTGTTTGAAAATAATCT
1021 TACCAGCTTTGGGTAAACTGTTT(A)n
```

FIG. 4

```
   1 TATCCCCTTCCTCCAGGTGGCTTGTTTCTTGCAGTGGTGGTGGTGGTGGTGGTGAGATCT
  61 AGCTTGGTTGGTTGGTGGCAGCTGGAGATCGATCGGGATGGGAGGGGGCGGGTGGAGCT
                                       M  G  R  G  R  V  E  L     8
                                                          MADS BOX
 121 GAAGAGGATCGAGAACAAGATCAACCGGAAGGTGACGTTCGCCAAGAGGAGGAATGGCCT
      K  R  I  E  N  K  I  N  R  K  V  T  F  A  K  R  R  N  G  L  28

181 GCTCAAGAAGGCGTACGAGCTCTCCGTCCTCTGCGACGCCGAGGTCGCCCTCATCATCTT
      L  K  K  A  Y  E  L  S  V  L  C  D  A  E  V  A  L  I  I  F  48

241 CTCCAACCGCGGCAAGCTCTACGAGTTCTGCAGCACCCAGAGCATGACTAAAACGCTTGA
      S  N  R  G  K  L  Y  E  F  C  S  T  Q  S  M  T  K  T  L  E  68

301 GAAGTATCAGAAATGCAGTTACGCAGGACCCGAAACAGCTGTCCAAAATAGAGAAAGTGA
      K  Y  Q  K  C  S  Y  A  G  P  E  T  A  V  Q  N  R  E  S  E  88

361 GCAATTGAAAGCTAGCCGCAATGAATACCTCAAACTGAAGGCAAGGGTTGAAAATTTACA
      Q  L  K  A  S  R  N  E  Y  L  K  L  K  A  R  V  E  N  L  Q 108
                                                             K BOX
 421 ACGGACTCAAAGAAATTTGCTGGGTCCAGATCTTGATTCATTAGGCATAAAAGAGCTCGA
      R  T  Q  R  N  L  L  G  P  D  L  D  S  L  G  I  K  E  L  E 128

481 GAGCCTAGAGAAGCAGCTTGATTCATCCCTGAAGCACGTCAGAACTACAAGGACAAAACA
      S  L  E  K  Q  L  D  S  S  L  K  H  V  R  T  T  R  T  K  H 148

541 TCTGGTCGACCAACTGACGGAGCTTCAGAGAAAGGAACAAATGGTTTCTGAAGCAAATAG
      L  V  D  Q  L  T  E  L  Q  R  K  E  Q  M  V  S  E  A  N  R 168

601 ATGCCTTAGGAGAAAACTGGAGGAAAGCAACCATGTTCGCGGGCAGCAAGTGTGGGAGCA
      C  L  R  R  K  L  E  E  S  N  H  V  R  G  Q  Q  V  W  E  Q 188

661 GGGCTGCAACTTAATTGGCTATGAACGTCAGCCTGAAGTGCAGCAGCCTCTTCACGGCGG
      G  C  N  L  I  G  Y  E  R  Q  P  E  V  Q  Q  P  L  H  G  G 208

721 CAATGGGTTCTTCCATCCACTTGATGCTGCTGGTGAACCCACCCTTCAGATTGGGTACCC
      N  G  F  F  H  P  L  D  A  A  G  E  P  T  L  Q  I  G  Y  P 228

781 TGCAGAGCATCATGAGGCGATGAACAGTGCGTGCATGAACACCTACATGCCCCCATGGCT
      A  E  H  H  E  A  M  N  S  A  C  M  N  T  Y  M  P  P  W  L 248

841 ACCATGATGATGACGGGACAATGAATTACGAAATAACAAGGATATGTGGCATATATGTGG
      P  *                                                       249

901 TGCCGCATACATGCATGTATCATGGCTAGCTACTTAATTGGAGTGATGGATTTGAACTAG
 961 TTTCGTATGTAGCCTGTTTGTGTGTAACTTGTGTGAGATACTACCTTAAAAACTATCGGT
1021 GTCTGTTGAACATATTCTGCGATCAACTTTAAGCGTATT(A)n
```

FIG. 5

```
   1 TGCTTTCCCCTCTCTTCCGCTTCGCGAGATTGGTTGATTCATCTCGCGATTGATCGAGCT
  61 CGAGCGGCGGTGAGGTGAGGTGGAGGAGGAGGAGGAGGAGATCGGGATGGGGAGAGG             4
                                                     M  G  R  G
                                                                   MADS BOX
 121 GAGGGTGGAGCTGAAGAGGATCGAGAACAAGATCAACAGGCAGGTGACGTTCGCGAAGCG
      R  V  E  L  K  R  I  E  N  K  I  N  R  Q  V  T  F  A  K  R    24

181 GAGGAATGGGCTGCTCAAGAAGGCGTACGAGCTCTCCGTGCTCTGCGACGCCGAGGTCGC
      R  N  G  L  L  K  K  A  Y  E  L  S  V  L  C  D  A  E  V  A    44

241 CCTCATCATCTTCTCCAACCGCGGCAAGCTCTACGAGTTCTGCAGCGGCCAAAGCATGAC
      L  I  I  F  S  N  R  G  K  L  Y  E  F  C  S  G  Q  S  M  T    64

301 CAGAACTTTGGAAAGATACCAAAAATTCAGTTATGGTGGGCCAGATACTGCAATACAGAA
      R  T  L  E  R  Y  Q  K  F  S  Y  G  G  P  D  T  A  I  Q  N    84

361 CAAGGAAAATGAGTTAGTGCAAAGCAGCCGCAATGAGTACCTCAAACTGAAGGCACGGGT
      K  E  N  E  L  V  Q  S  S  R  N  E  Y  L  K  L  K  A  R  V   104
                                                                   K BOX
 421 GGAAAATTTACAGAGGACCCAAAGGAATCTTCTTGGTGAAGATCTTGGGACACTTGGCAT
      E  N  L  Q  R  T  Q  R  N  L  L  G  E  D  L  G  T  L  G  I   124

461 AAAAGAGCTAGAGCAGCTTGAGAAACAACTTGATTCATCCTTGAGGCACATTAGATCCAC
      K  E  L  E  Q  L  E  K  Q  L  D  S  S  L  R  H  I  R  S  T   144

541 AAGGACACAGCATATGCTTGATCAGCTCACTGATCTCCAGAGGAGGGAACAAATGTTGTG
      R  T  Q  H  M  L  D  Q  L  T  D  L  Q  R  R  E  Q  M  L  C   164

601 TGAAGCAAATAAGTGCCTCAGAAGAAAACTGGAGGAGAGCAACCAGTTGCATGGACAAGT
      E  A  N  K  C  L  R  R  K  L  E  E  S  N  Q  L  H  G  Q  V   184

661 GTGGGAGCACGGCGCCACCCTACTCGGCTACGAGCGGCAGTCGCCTCATGCCGTCCAGCA
      W  E  H  G  A  T  L  L  G  Y  E  R  Q  S  P  H  A  V  Q  Q   204

721 GGTGCCACCGCACGGTGGCAACGGATTCTTCCATTCCCTGGAAGCTGCCGCCGAGCCCAC
      V  P  P  H  G  G  N  G  F  F  H  S  L  E  A  A  A  E  P  T   224

781 CTTGCAGATCGGGTTTACTCCAGAGCAGATGAACAACTCATGCGTGACTGCCTTCATGCC
      L  Q  I  G  F  T  P  E  Q  M  N  N  S  C  V  T  A  F  M  P   244

841 GACATGGCTACCCTGAACTCCTGAAGGCCGATGCGACAACCAATAAAAACGGATGTGACG
      T  W  L  P  *                                                 248

901 ACACAGATCAAGTCGCACCATTAGATTGATCTTCTCCTACAAGAGTGAGACTAGTAATTC
 961 CGCGTTTGTGTGCTAGCGTGTTGAAACTTTTCTGATGTGATGCACGCACTTTTAATTATT
1021 ATTAAGCGTTCAAGGACTAGTATGTGGTATAAAAGCCCGTACGTGACAGCCTATGGTTAT
1081 ATGCTGCGCAAAAACTACGTATGGTACAGTGCAGTGCCTGTACATTTCATAATTTGCGGG
1141 TAAAGTTTATTGACTATATATCCAGTGTGTCAAATATAAT(A)n
```

FIG. 6

MADS BOX

```
GRGRVELKRIENKINRQVTFSKRRNGLLKKAYELSVLCDAEVALIIFSSRGKLYEF    1
GRGRVELKRIENKINRQVTFSKRRNGLLKKAYELSVLCDAEVALIIFSSRGKLYEF    2
GRGRVELKRIENKINRQVTFSKRRNGLLKKAYELSVLCDAEVALIIFSGRGKLYEF    3
GRGRVEMKRIENKINRQVTFSKRRNGLLKKAYELSVLCDAEVALIIFSSRGKLYEF    4
GRGRVELKRIENKINRQVTFAKRRNGLLKKAYELSVLCDAEVALIIFSNRGKLYEF    5
GRGRVELKRIENKINRQVTFAKRRNGLLKKAYELSVLCDAEVALIIFSNRGKLYEF    6
GRGRVELKRIENKINRQVTFAKRRNGLLKKAYELSVLCDAEVALIIFSNRGKLYEF    7
GRGRVELKRIEGKINRQVTFAKRRNGLLKKAYELSVLCDAEVALIIFSNRGKLYEF    8
GRGRVELKMIENKINRQVTFAKRRKRLLKKAYELSVLCDAEVALIIFSNRGKLYEF    9
GRGRVELKRIENKINRQVTFAKRRNGLLKKAYELSVLCDAEVALIIFSNRGKLYEF   10
GRGRVELKRIENKINRQVTFAKRRNGLLKKAYELSVLCDAEVSLIVFSNRGKLYEF   11
GRGKVELKRIENKISRQVTFAKRRNGLLKKAYELSLLCDAEVALIIFSGRGRLFEF   12
GRGRVQLKRIENKINRQVTFSKRRAGLLKKAHEISVLCDAEVALVVFSHKGKLFEY   13
GRGKIEIKRIENTTNRQVTFCKRRNGLLKKAYELSVLCDAEVALIVFSSRGRLYEY   14
ARGKIQIKRIENQTNRQVTYSKRRNGLFKKAHELTVLCDARVSIIMFSSSNKLHEY   15
GRGKIEIKRIENANNRVVTFSKRRNGLVKKAKEITVLCDAKVALIIFASNGKMIDY   16
```

FIG. 7A

K BOX

```
HEMSKLKAKFEALQRTQ.RHLLGEDLGPLSVKELQQLEKQLECALSQARQRKTQLMMEQVEELRRK    1
QEMSKLRAKFEALQRTQ.RHLLGEELGPLSVKELQQLEKQLECALSQARQRKTQLMMEQVEELRRK    2
QEMSKLRAKFEALQRTQ.RHLLGEDLGPLSVKELQQLEKQLECALSQARQRKTQVMMEQVEELRRT    3
QEVTKLKSKYESLVRTN.RNLLGEDLGEMGVKELQALERQLEAALTATRQRKTQVMMEEMEDLRKK    4
NEYLKLKARVENLQRTQ.RNLLGEDLGTLGIKELEQLEKQLDSSLRHIRSTRTQHMLDQLTDLQRR    5
NEYLKLKARVENLQRTQ.RNLLGPDLDSLGIKELESLEKQLDSSLKHVRTTRTKHLVDQLTELQRK    6
QEYLKLKARYEALQRSQ.RNLLGEDLGPLNSKELESLERQLDMSLKQIRSTRTQLMLDQLQDLQRK    7
QEYLKLKGRYEALQRSQ.RNLLGEDLGPLNSKELESLERQLDMSLKQIRSTRTQLMLDQLTDYQRK    8
QEYLKLKNRVEALQRSQ.RNLLGEDLGPLGSKELEQLERQLDSSLRQIRSTRTQFMLDQLADLQRR    9
REYLKLKGRYENLQRQQ.RNLLGEDLGPLNSKELEQLERQLDGSLKQVRSIKTQYMLDQLSDLQNK   10
REYLKLKGRYENLQRQQ.RNLLGEDLGPLNSKELEQLERQLDGSLKQVRCIKTQYMLDQLSDLQGK   11
QEYLKLKTRVEFLQTTQ.RNILGEDLGPLSMKELEQLENQIEVSLKQIRSRKNQALLDQLFDLKSK   12
MEYNRLKAKIELLER.NQRHYLGEDLQAMSPKELQNLEQQLDTALKHIRTRKNQLMYESINELQKK   13
QESAKLRQQI.ISIQNSNRQLMGETIGSMSPKELRNLEGRLERSITRIRSKKNELLFSEIDYMQKR   14
QETKRKLLETNRNLRTQIKQRLGECLDELDIQELRRLEDEMENTFKLVRERKFKSLGNQIETTKKK   15
NE.IDRIKKENDSLQLELRHLKGE...DIQSLNLKNLMAVEHAIEHGLDKVRDHQMEILISKRRN.   16
```

FIG. 7B

C-TERMINAL END

| Sequence | # | Name |
|---|---|---|
| EPTLQIGYP.H.QFVPAEANTIQRSTAPAGAENNFML.GWVL | 1 | OsMADS6 (rice) |
| EPTLQIGYP.HHQFPPPEA.VNNIPRSAATGENNFML.GWVL | 2 | ZAG3 (maize) |
| EPTLQIGYPPHHQFLPSEA.ANNIPRSPPGGENNFML.GWVL | 3 | ZAG5 (maize) |
| EPFLQIG...FGQHYYVGGEGSSVSKSNVAGETNFVQ.GWVL | 4 | AGL6 (Arabidopsis) |
| EPTLQIG.............FTPEQMNNS.CVTAFMPT.WLP | 5 | OsMADS8 (rice) |
| EPTLQIGY...........PAEHHEAMNSACMNTYMPP.WLP | 6 | OsMADS7 (rice) |
| EPTLQIGY..........QNDPITVGGAGPSVNNYMAG.WLP | 7 | FBP2 (petunia) |
| EPTLQIGY..........QNDPITVGGAGPSVNNYMAG.WLP | 8 | TM5 (tomato) |
| EPTLQIGY...........HSDITMATATASTVNNYMPPGWLG+7 | 9 | Om1 (orchid) |
| NPTLQMGY....DNPVCSEQITATTQAQAQPGNGYIP.GWML | 10 | AGL2 (Arabidopsis) |
| DPTLQIGY....SHPVCSEQMAVTVQGQSQQGNGYIP.GWML | 11 | AGL4 (Arabidopsis) |
| DHSLQIGYHHPHAHHHQAYMDHLSNEAADMVAHHPNEHIPSG+2 | 12 | OsMADS1 (rice) |
| SPFLNMGGLYQEDDPMAMRNDLELTLEPVYNCNLGCFAA | 13 | AP1 (Arbidopsis) |
| VAALQPNNHHYSSAGRQDQTALQLV | 14 | AG (Arbidopsis) |
| FHQNHHHYYPNHGLHAPSASDIITFHLLE | 15 | AP3 (Arbidopsis) |
| VAALQPNLQEKIMSLVID | 16 | pi (Arbidopsis) |

FIG. 7C

FIG. 7D

```
   1 AAGACTGCAAGGGAGAGGGAGAGAGAGGGAAGCTTGCAGGCTGCAGCTAACTAGCTAGGC
  61 AAGGAGAGAGAGGAGATAGATCAAGAAGAGATTTTGAGACCGAGAGAGAGCTAGAGAGAG
 121 ATCGATGGGGCGAGGGAAAGTAGAGCTGAAGCGGATCGAGAACAAGATAAGCCGGCAGGT
       M  G  R  G  K  V  E  L  K  R  I  E  N  K  I  S  R  Q  V    19
                                                                MADS BOX
 181 GACGTTCGCGAAGAGGAGGAACGGGCTGCTGAAGAAGGCGTACGAGCTGTCCGTGCTCTG
       T  F  A  K  R  R  N  G  L  L  K  K  A  Y  E  L  S  V  L  C  39

241 CGACGCCGAGGTCGCCCTCATCATCTTCTCCACCCGCGGCCGCCTCTTCGAGTTCTCCAC
       D  A  E  V  A  L  I  I  F  S  T  R  G  R  L  F  E  F  S  T  59

301 CTCCTCCTGTATGTACAAGACACTGGAGCGATACCGCAGTTGCAACTACAACCTTAACTC
       S  S  C  M  Y  K  T  L  E  R  Y  R  S  C  N  Y  N  L  N  S  79

361 ATGTGAAGCATCTGCTGCACTGGAAACTGAACTAAGCAATTACCAAGAGTACTTAAAGTT
       C  E  A  S  A  A  L  E  T  E  L  S  N  Y  Q  E  Y  L  K  L  99
                                                                   K BOX
 421 AAAGACAAGAGTTGAGTTCCTACAAACAACTCAGAGAAATCTTCTTGGCGAGGACTTGGT
       K  T  R  V  E  F  L  Q  T  T  Q  R  N  L  L  G  E  D  L  V 119

481 TCCACTTAGCTTGAAGGAGCTCGAGCAACTTGAGAACCAGATCGAGATATCCCTCATGAA
       P  L  S  L  K  E  L  E  Q  L  E  N  Q  I  E  I  S  L  M  N 139

541 TATCAGGTCATCAAAGAATCAACAGTTGCTTGATCAAGTATTTGAGCTCAAACGTAAGGA
       I  R  S  S  K  N  Q  Q  L  L  D  Q  V  F  E  L  K  R  K  E 159

601 ACAACAACTTCAAGATGCTAATAAAGACTTAAAAAGGAAGATACAAGAAACTAGTGGAGA
       Q  Q  L  Q  D  A  N  K  D  L  K  R  K  I  Q  E  T  S  G  E 179

661 AAATATGCTTCATATATCTTGCCAAGATGTAGGGCCCAGTGGCCATGCTAGTGAAGCTAA
       N  M  L  H  I  S  C  Q  D  V  G  P  S  G  H  A  S  E  A  N 199

721 CCAAGAGTTTCTCCATCATGCAATTTGTGACCCTTCCCTGCATATAGGGTATCAAGCTTA
       Q  E  F  L  H  H  A  I  C  D  P  S  L  H  I  G  Y  Q  A  Y 219

781 CATGGATCACCTCAACCAATGAATGAATTGCTTATCACATTAATGGACATCTCCTATGTT
       M  D  H  L  N  Q  *                                         225

841 GGATGTGGTGTTTGACGTAATGCTCTCTTTTACATGCGGGTTTTACCTTAAGTGTGTGTG
 901 CTAAATTTAGTGCGTTTGTTTATGCTCTTTTGAACTGAACAAAGGAATGATCCCGGTTTG
 961 ATTGATGAATGCTGCAAGAACATAATCTATATGTTAGTCTGAATTCAGTATGTAATGAAG
1021 ATGTTTT(A)n
```

FIG. 9

MADS BOX

```
            GRGRVELKRIENKINRQVTFAKRRNGLLKKAYELSVLCDAEVALIIFSSRGKLYEF
OsMADS5     GRGKVELKRIENKISRQVTFAKRRNGLLKKAYELSVLCDAEVALIIFSTRGRLFEF
OsMADS1     GRGKVELKRIENKISRQVTFAKRRNGLLKKAYELSLLCDAEVALIIFSGRGRLFEF
FBP2        GRGRVELKRIENKINRQVTFAKRRNGLLKKAYELSVLCDAEVALIIFSNRGKLYEF
TM5         GRGRVELKRIEGKINRQVTFAKRRNGLLKKAYELSVLCDAEVALIIFSNRGKLYEF
AGL4        GRGRVELKRIENKINRQVTFAKRRNGLLKKAYELSVLCDAEVSLIVFSNRGKLYEF
AGL2        GRGRVELKRIENKINRQVTFAKRRNGLLKKAYELSVLCDAEVALIIFSNRGKLYEF
OM1         GRGRVELKMIENKINRQVTFAKRRKRLLKKAYELSVLCDAEVALIIFSNRGKLYEF
ZAG3        GRGRVELKRIENKINRQVTFSKRRNGLLKKAYELSVLCDAEVALIIFSSRGKLYEF
ZAG5        GRGRVELKRIENKINRQVTFSKRRNGLLKKAYELSVLCDAEVALIIFSGRGKLYEF
AGL6        GRGRVEMKRIENKINRQVTFSKRRNGLLKKAYELSVLCDAEVALIIFSSRGKLYEF
AP1         GRGRVQLKRIENKINRQVTFSKRRAGLLKKAHEISVLCDAEVALVVFSHKGKLFEY
AP3         ARGKIQIKRIENQTNRQVTYSKRRNGLFKKAHELTVLCDARVSIIMFSSSNKLHEY
PI          GRGKIEIKRIENANNRVVTFSKRRNGLVKKAKEITVLCDAKVALIIFASNGKMIDY
AG          GRGKIEIKRIENTTNRQVTFCKRRNGLLKKAYELSVLCDAEVALIVFSSRGRLYEY
```

I REGION

```
            CSGSSSMLKTLEERYQKCNYNAPESNNSAAEELESSYQWS
OsMADS5     -STSSCMYKTL-ER-RSCNYNLNSCEASAALETELSNY--
OsMADS1     -SSSSCMYKTL-ERYRSCNYN----SQDAAAPENEINY--
FBP2        CS-SSSMLKTLE-RYQKCNYGAPETNISTREALEISSQ--
TM5         CS-SSSMLKTLE-RYQKCNYGAPEPNISTREALEISSQ--
AGL4        CS-TSNMLKTLE-RYQKCSYGSIEVNNKPAKELENSY---
AGL2        CS-SSNMLKTL-DRYQKCSYGSIEVNNKPAKELENSY---
OM1         CS-STSMLKTLE-KYQKCNFGSPESTIISRE--TQSSQ--
ZAG3        --GSAGITKTL-ERYQHCCYNAQDSN-GALSETQSWY---
ZAG5        --GSAGVTKTL-ERYQHCCYNAQDSNNSALSESQSWY---
AGL6        --GSVGIEST-IERY-NRCYNCSLSNNKPEETTQSWC---
AP1         -STDSCMEKILE-RYERYSY---AERQLIAPESDVNTNWS
AP3         --ISPNTTTKEIVDLYQTISDVDVWATQYERM--------
PI          PSMDLGAMLDQYQKLSGKKLWDAKHENLS-----------
AG          --SNNSVKGT-IERYKKAISDNSNTGSVAEINAQYYQ---
```

K BOX

```
            QETYLKLKARYEALQRTQRNLLGEDLGPLSSKELEQLERQLEASLKQIRSRKTQLMLDQLEDLQRK
OsMADS5     QE-YLKLKTRVEFLQTTQRNLLGEDLVPLSLKELEQLENQIEISLMNIRSSKNQQLLDQVFELKRK
OsMADS1     QE-YLKLKTRVEFLQTTQRNILGEDLGPLSMKELEQLENQIEVSLKQIRSRKNQALLDQLFDLKSK
FBP2        QE-YLKLKARYEALQRSQRNLLGEDLGPLNSKELESLERQLDMSLKQIRSTRTQLMLDQLQDLQRK
TM5         QE-YLKLKGRYEALQRSQRNLLGEDLGPLNSKELESLERQLDMSLKQIRSTRTQLMLDQLTDYQRK
AGL4        RE-YLKLKGRYENLQRQQRNLLGEDLGPLNSKELEQLERQLDGSLKQVRCIKTQYMLDQLSDLQGK
AGL2        RE-YLKLKGRYENLQRQQRNLLGEDLGPLNSKELEQLERQLDGSLKQVRSIKTQYMLDQLSDLQNK
OM1         QE-YLKLKNRVEALQRSQRNLLGEDLGPLGSKELEQLERQLDSSLRQIRSTRTQFMLDQLADLQRR
ZAG3        QE-MSKLRAKFEALQRTQRHLLGEELGPLSVKELQQLEKQLECALSQARQRKTQLMMEQVEELRRK
ZAG5        QE-MSKLRAKFEALQRTQRHLLGEDLGPLSVKELQQLEKQLECALSQARQRKTQVMMEQVEELRRT
AGL6        QE-VTKLKSKYESLVRTNRNLLGEDLGEMGVKELQALERQLEAALTATRQRKTQVMMEEMEDLRKK
AP1         ME-YNRLKAKIELLERNQRHYLGEDLQAMSPKELQNLEQQLDTALKHIRTRKNQLMYESINELQKK
AP3         QETKRKLLETNRNLRTQIKQRLGECLDELDIQELRRLEDEMENTFKLVRERKFKSLGNQIETTKKK
PI          NE-IDRIKKENDSLQLELRHLKGED---IQSLNLKNLMAVEHAIEHGLDKVRDHQMEILISKRRN-
AG          QE-SAKLRQQIISIQNSNRQLMGETIGSMSPKELRNLEGRLERSITRIRSKKNELLFSEIDYMQKR
```

FIG. 10

GENES CONTROLLING FLORAL DEVELOPMENT AND APICAL DOMINANCE IN PLANTS

CROSS REFERENCE TO RELATED APPLICATION

This application is a continuation-in-part of U.S. patent application Ser. No. 08/485,981, filed Jun. 7, 1995, now U.S. Pat. No. 5,861,542, which is a continuation-in-part of U.S. patent application Ser. No. 08/323,449, filed on Oct. 14, 1994, now U.S. Pat. No. 5,859,326, incorporated herein by reference.

TECHNICAL FIELD

This invention is related to compositions and methods for affecting plant floral development and the timing of the transition from vegetative to reproductive growth.

BACKGROUND ART

Floral initiation is controlled by several factors including photoperiod, cold treatment, hormones, and nutrients (Coen, Plant Mol. Biol. 42:241–279, 1991; Gasser, Annu. Rev. Plant Physiol. Plant Mol. Biol. 42:621–649, 1991). Physiological studies have demonstrated that vegetative tissues are the site for signal perception and for generation of chemicals that cause the transition from vegetative growth to flowering (Lang, in: Encyclopedia of Plant Physiology, vol. 15, Berlin, ed., Springer-Verlag, pp. 1371–1536, 1965; Zeevaartm, in: Light and the Flowering Process, Vince-Prue et al., eds., Orlando Academic Press, pp. 137–142, 1984). Genetic analysis revealed that there are several types of mutants that alter flowering time. In *Arabidopsis thaliana*, there are at least two mutant groups based on their response to photoperiod and vernalization (Martinez-Zapater et al., in: *Arabidopsis*, Meyerowitz and Somerville, eds., Plainview, N.Y., Cold Spring Harbor Laboratory, pp. 403–433, 1994). These phenotypes suggest that there are multiple pathways that lead to flowering.

Study on mutants that interfere with normal flower development has provided some information on controlling the mechanisms of the development. This has led to the knowledge that there are at least two genes needed for induction of flower development: LEAFY (LFY) and APETALAI (API) genes in Arabidopsis (Weigel, Annu. Rev. Genet. 29:19–39, 1995), and FLORICAULA (FLO) and SQUA-MOSA (SQUA) genes in *Antirrhinum majus* (Bradley et al., Cell 72:85–95, 1993). Cloning and analysis of these genes revealed that the LFY and FLO genes are homologs and encode proteins that each contain a proline-rich region at the N-terminus and a highly acidic central region, which are features of certain types of transcription factors that contain a conserved MADS-box sequence (Huijser et al., EMBO J. 11:1239–1249, 1992; Mandel et al., Nature 360:273–277, 1992). MADS box-containing genes were isolated from several plant species and are known to play important roles in plant development, especially flower development. Arabidopsis homeotic genes—AGAMOUS (AG), PISTILATA (PI), and APETALA3 (AP3)—are members of the MADS box gene family (Yanofsky et al., Nature 346:35–39, 1990; Goto and Meyerowitz, Genes Devel. 8:1548–1560, 1994; Jack et al., Cell 68:683–697, 1992). Similar homeotic genes from *A. majus*—PLENA (PLE), GLOBOSA (GLO), and DEFICIENS A (DEFA)—are also MADS box genes (Bradley et al., Cell 72:85–95, 1993; Tröbner et al., EMBO J. 11:4693–4704, 1992; Sommer et al., EMBO J. 9:605–613, 1990). Characterization of these gene products showed that the conserved MADS box domain is for sequence-specific DNA binding, dimerization, and attraction of secondary factors (Pellegrini et al., Nature 376:490–498, 1995). The DNA sequence with which the MADS box domains interact is the consensus finding site, $CCA/T_6GG$ (Pollock and Treisman, Genes Dev. 5:2327–2341, 1991; Huang et al., Nucl. Acids Res. 21:4769–4776 1993). In addition to the MADS-box domain, the plant MADS box proteins include the K-box domain, a second conserved region carrying 65–70 amino acid residues. The K-box domain was named due to the structural resemblance to the coiled coil domain of keratin (Ma et al., Genes Dev. 5:484–495, 1991) and has been suggested to be related to protein-protein interactions (Pnueli et al., Plant J. 1:255–266, 1991). Similar MADS-box genes have also been studied in other plants including tomato, rape, tobacco, petunia, maize, and rice (Theiβen and Saedler, Curr. Opin. Genet. Dev. 5:628–639, 1995). A number of plant MADS box genes that deviate from the functions of the typical meristem identity and organ identity genes have been identified. These genes are involved in the control of ovule development (Angenent et al., Plant Cell 7:1569–1582, 1995), vegetative growth (Mandel et al., Plant Mol. Biol. 25:319–321, 1994), root development (Rounseley et al., Plant Cell 7:1259–1269, 1995), embryogenesis (Heck et al., Plant Cell 7:1271–1282, 1995), or symbiotic induction (Heard and Dunn, Proc. Natl. Acad. Sci. USA 5273–5277, 1995).

There are a large number of MADS box genes in each plant species. In maize, at least 50 different MADS box genes consist of a multigene family and these genes are dispersed throughout the plant genome (Mena et al., Plant J. 8:845–854, 1995; Fischer et al., Proc. Natl. Acad. Sci. USA 92:5331–5335, 1995). The MADS box multigene family can be divided into several subfamilies according to their primary sequences, expression patterns, and functions (Theiβen and Saedler, Curr. Opin. Genet. Dev. 5:628–639, 1995).

The timing of the transition from vegetative growth to flowering is one of the most important steps in plant development This step determines the quality and quantity of most crop species by affecting the balance between vegetative and reproductive growth. It would therefore be highly desirable to have means to affect the timing of this transition. The present invention meets this and other needs.

SUMMARY OF THE INVENTION

The present invention provides compositions and methods related to the OsMADS1, OsMADS5, OsMADS6, OsMADS7, and OsMADS8 genes of *Oryza sativa* and the NtMADS3 gene of *Nicotiana tabacum*, and alleles and homologs thereof. Expression of such genes in transgenic plants causes an altered phenotype, including phenotypes related to the timing of the transition between vegetative and reproductive growth.

It is an object of the invention to provide isolated nucleic acids that hybridize to an OsMADS1 cDNA (SEQ ID NO:1 and SEQ ID NO:2) under at least moderately stringent hybridization conditions and that, when expressed in transgenic plants, confer on the plants at least one phenotype including (1) diminished apical dominance, (2) early flowering, (3) a partially or completely altered daylength requirement for flowering, (4) greater synchronization of flowering, or (5) a relaxed vernalization requirement.

It is another object of the invention to provide isolated nucleic acids comprising (1) a sequence of at least 30 contiguous nucleotides of the native OsMADS5 (SEQ ID NO:54), OsMADS6 (SEQ ID NO:12), OsMADS7 (SEQ ID NO:14), or OsMADS8 gene (SEQ ID NO:16), or an allele or homolog thereof, or (2) a sequence of at least 100 contiguous nucleotides that has at least 70% nucleotide sequence similarity with OsMADS5 (SEQ ID NO:54), OsMADS6 (SEQ ID NO:12), OsMADS7 (SEQ ID NO:14), or OsMADS8 (SEQ ID NO:16). When expressed in a transgenic plant, such nucleic acids produce at least one phenotype including (1) diminished apical dominance, (2) early flowering, (3) a partially or completely altered day-length requirement for flowering, (4) greater synchronization of flowering, or (5) a relaxed vernalization requirement. Preferably, such isolated nucleic acids comprise only silent or conservative substitutions to a native (wild-type) gene sequence.

A further object of the invention is to provide transgenic plants comprising such nucleic acids.

A further object of the invention is to provide probes and primers comprising a fragment of the native OsMADS5 (SEQ ID NO:54), OsMADS6 (SEQ ID NO:12), OsMADS7 (SEQ ID NO:14), or OsMADS8 gene (SEQ ID NO:16) gene that is capable of specifically hybridizing under stringent conditions to the native gene from which the probes or primers are derived. Such probes and primers are useful, for example, for obtaining homologs of such genes from plants other than rice.

It is a further object of the invention to use the nucleic acids described above to produce transgenic plants having altered phenotypes, specifically, to introduce such nucleic acids into plant cells, thereby producing a transformed plant cell, and to regenerate from the transformed plant cell a transgenic plant comprising the nucleic acid.

The foregoing and other objects and advantages of the invention will become more apparent from the following detailed description and accompanying drawings.

BRIEF DESCRIPTION OF THE DRAWINGS

FIG. 1A shows the nucleotide and deduced amino-acid sequences of OsMADS1 cDNA (SEQ ID NO:1 and SEQ ID:2). MADS-box and K-box regions are underlined. The positions of nucleotides and amino acids are shown on the left and right, respectively.

FIG. 1B provides a comparison of MADS-box regions, showing the alignment of the MADS-box sequence of OsMADS1 (residues 2–57) (SEQ ID NO:3 with the MADS-box sequence of AP1 (SEQ ID NO:4), SQUA (SEQ ID NO:5), AG (SEQ ID NO:6), PLE (SEQ ID NO:7), AP3 (SEQ ID NO:8), and DEF A (SEQ ID NO:9). The asterisks indicate amino acids that are identical to corresponding amino acids of OsMADS1.

FIG. 2 shows the nucleotide and deduced amino-acid sequence of the NtMADS3 cDNA. (SEQ ID NO:10 and SEQ ID:11) The positions of nucleotides and amino acids are shown on the left and right, respectively.

FIG. 3 shows a comparison of the deduced NtMADS3 polypeptide sequence (top; SEQ ID NO: 11) and the deduced OsMADS polypeptide sequence with (bottom; SED ID NO:2.

FIG. 4 shows nucleotide and deduced amino-acid sequences of the OsMADS6 cDNA (SEQ ID NO:12 and SEQ ID NO:13). MADS-box and K-box regions are underlined. The positions of nucleotides and amino acids are shown on the left and right, respectively. The double underlined sequence is the PstI site, which was used to generate the gene-specific probe of the 360 bp fragment located at the 3' region of the OsMADS6 cDNA (SEQ ID NO:12).

FIG. 5 shows nucleotide and deduced amino-acid sequences of the OsMADS7 cDNA (SEQ ID NO:14 and SEQ ID NO:15). The MADS-box and K-box regions are underlined. The positions of nucleotides and amino acids are shown on the left and right, respectively. The double-underlined sequence is the PstI site, which was used to generate the gene-specific probe of the 280 bp fragment located at the 3'-end region of the OsMADS7 cDNA (SEQ ID NO:14).

FIG. 6 shows nucleotide and deduced amino-acid sequences of the OsMADS8 cDNA (SEQ ID NO:16 and SEQ ID NO:17). The MADS-box and K-box regions are underlined. The positions of nucleotides and amino acids are shown on the left and right, respectively. The double-underlined sequence is the NheI site, which was used to generate the gene-specific probe of the 230-bp fragment located at 3'-end region of the OsMADS8 cDNA (SEQ ID NO:16).

FIGS. 7A–7C show alignments of the OsMADS6 (SEQ ID NO:13) OsMADS7 (SEQ ID NO:15) and OsMADS8 (SEQ ID NO:17) proteins with other MADS-box proteins. The MADS-box region (A), K-box region (B), and the end of the C-terminal region (C) were aligned by introducing gaps (points) for maximum sequence homology. Dark highlights indicate conserved sequences among the AGL2 family, whereas the light highlights indicate conserved sequences within the FBP2 subfamily. 1, OsMADS6 (rice) (SEQ ID NO:13: MADS box, K box, and C-terminal end]; 2, ZAG3 (maize) (SEQ ID NO:18, MADS box; SEQ ID NO:30, K box; SEQ ID NO:42, C-terminal end); 3, ZAG5 (maize) (SEQ ID NO:19, MADS box; SEQ ID NO:31, K box; SEQ ID NO:43, C-terminal end); 4, AGL6 (Arabidopsis) (SEQ ID NO:20, MADS box; SEQ ID NO:32, K box; SEQ ID NO:44, C-terminal end); 5, OsMADS8 (rice) (SEQ ID NO:17, MADS box, K box, and C-terminal end); 6, OsMADS7 (rice) (SEQ ID NO:15, MADS box, K box, and C-terminal end); 7, FBP2 (petunia) (SEQ ID NO:21, MADS box; SEQ ID NO:33, K box; SEQ ID NO:45, C-terminal end); 8, TM5 (tomato) (SEQ ID NO:22, MADS box; SEQ ID NO:34, K box; SEQ ID NO:46, C-terminal end); 9, OM1 (orchid) (SEQ ID NO:23, MADS box; SEQ ID NO:35, K box; SEQ ID NO:47, C-terminal end); 10, AGL2 (Arabidopsis) (SEQ ID NO:24, MADS box; SEQ ID NO:36, K box; SEQ ID NO:48, C-terminal end); 11, AGL4 (Arabidopsis) (SEQ ID NO:25, MADS box; SEQ ID NO: 37, K box; SEQ ID NO:49, C-terminal end); 12, OsMADS1 (rice) (SEQ ID NO:2, MADS box, K box, and C-terminal end); 13, AP1 (Arabidopsis) (SEQ ID NO:26, MADS box; SEQ ID NO:38, K box; SEQ ID NO:50, C-terminal end); 14, AG (Arabidopsis) (SEQ ID NO:27, MADS box; SEQ ID NO:39, K box; SEQ ID NO:51, C-terminal end); 15, AP3 (Arabidopsis) (SEQ ID NO:28, MADS box; SEQ ID NO:40, K box; SEQ ID NO:52, C-terminal end); 16, PI (Arabidopsis) (SEQ ID NO:29, MADS box; SEQ ID NO:41, K box; SEQ ID NO:53, C-terminal end).

FIG. 7D shows the structure of MADS-box proteins. M, MADS-box region; I, I region: K, K-box region, C, C-terminal region; CE, C-terminal end region.

FIG. 9 shows nucleotide and deduced amino-acid sequences of the OsMADS5 cDNA (SEQ ID NO:54 and SED ID NO:55). The MADS-box and K-box regions are underlined. The positions of nucleotides and amino acids are shown on the left and right, respectively. The double-underlined sequences are EcoRI and HindIII sites, which were used to generate the genespecific 260-bp fragment.

FIG. 10 shows alignments of the OsMADS5 protein (SEQ ID NO:55) with other MADS-box proteins. Gaps (dashes) were introduced for maximum sequence homology. Highlights indicate conserved sequences. The consensus MADS-box, I-region, and K-box sequences are shown (SEQ ID NO: 56, SEQ ID NO:57, and SEQ ID NO:58, respectively).

DETAILED DESCRIPTION OF THE INVENTION

Figure 8:
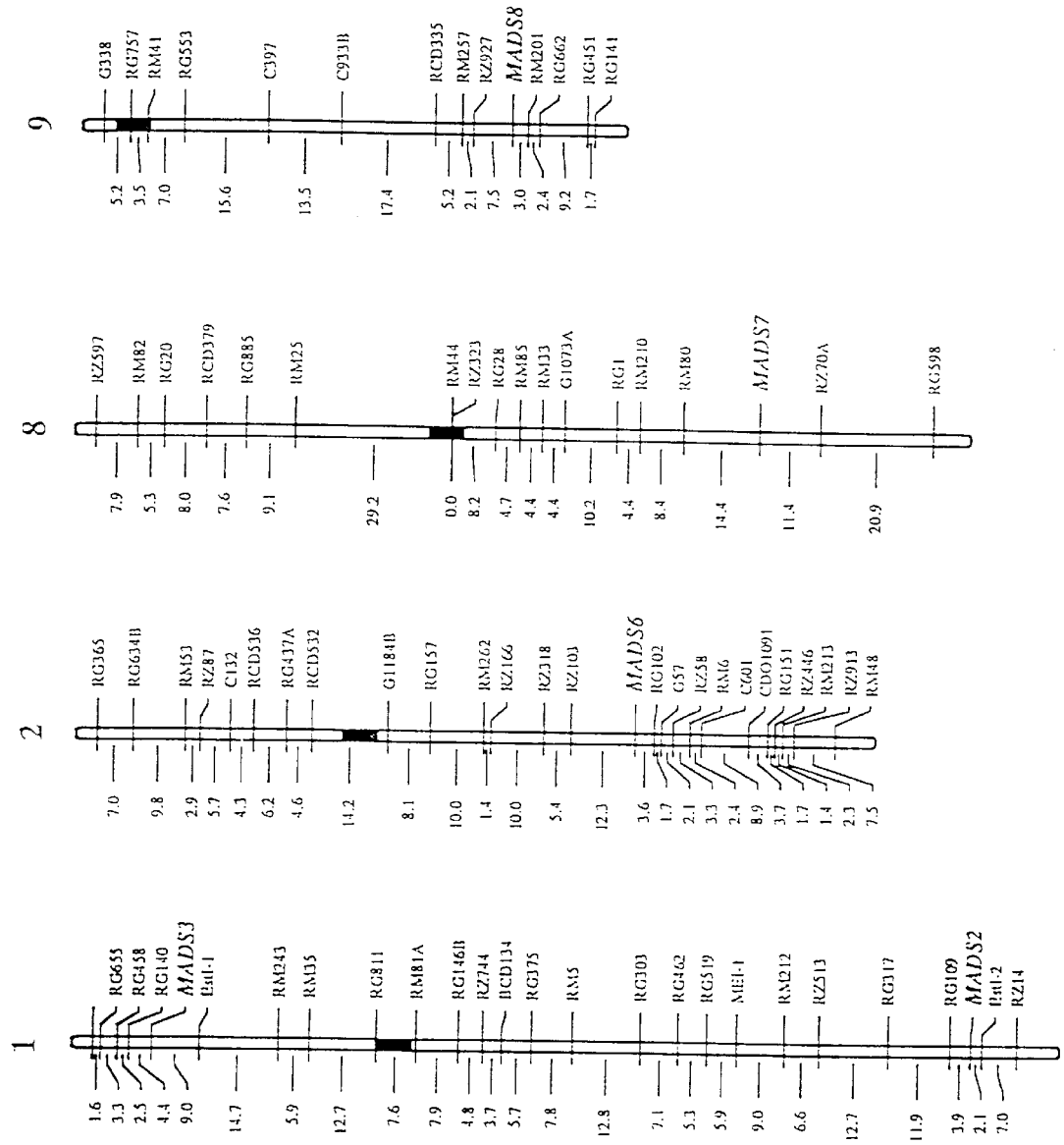
FIG. 8 shows genetic maps of the OsMADS genes. The locations of OsMADS genes along with RFLP markers (RG, G), cDNA markers (RZ and C), and microsatellite markers (RM) are indicated. Map distance is given in cM on the left of each chromosome. Dark bars represent the centromere regions.

Nine different MADS-box genes have been isolated, eight from rice, OsMADS1, OsMADS2, OsMADS3, OsMADS4, OsMADS5, OsMADS6, OsMADS7, and OsMADS8, and one from tobacco, NtMADS3. OsMADS2–8 were isolated from cDNA libraries under moderate stringency hybridization conditions using OsMADS1 as a probe, as described below.

Sequence similarity to other MADS-box genes indicated that OsMADS1 belongs to the AGL2 family (Example 1; Chung et al., 1994), OsMADS2 and OsMADS4 to the GLOBOSA family (Chung et al., 1995), and OsMADS3 to the AG family (Kang et al., 1995). Functional analysis by ectopic expression in a heterologous tobacco system indicated that OsMADS1 is involved in controlling the timing of flowering and OsMADS3 is important for anther development, as discussed in the Examples below.

The present invention provides compositions and methods related to additional MADS-box genes of rice, OsMADS5, OsMADS6, OsMADS7, OsMADS8, and their alleles and homologs (collectively referred to below as "OsMADS5–8"). These genes are useful, for example, for producing dwarf plants and for affecting the timing of the transition from vegetative to reproductive growth in a wide variety of plants, including various dicotyledonous and monocotyledonous crop plants and tree species (see Schwarz-Sommer et al., Science 250:931–936, 1990, regarding "MADS-box" genes).

Use of the Genes and their Alleles and Homologs for Crop Improvement

The MADS-box genes and polypeptides disclosed herein are useful for the following purposes, among others. For simplicity of expression, the OsMADS1 gene and polypeptide are discussed below, but such definitions apply equally to the other MADS-box genes or polypeptides disclosed herein.

Early flowering. The timing of the transition between vegetative and reproductive growth is an important agronomic trait, serving as a crucial factor in determining crop yields. Expression of the OsMADS1 gene in transgenic plants makes it possible to affect the transition from vegetative to reproductive growth in a wide variety of plants, whether the plants are long-day, short-day, or day-neutral plants.

When the OsMADS1 gene is expressed in transgenic plants of day-neutral species, the resulting transgenic plants flower earlier than control plants. Transgenic long-day and short-day flowering plants expressing the OsMADS1 gene also flower earlier under permissive conditions than control plants. The compositions and methods according to the present invention therefore permit one to reduce the length of the vegetative growth stage of cereal, fruit, vegetable, floricultural, and other crop species.

Producing dwarf plant varieties. Although it has been possible to enhance the harvest index in grain crops by the use of dwarfing genes, the isolation of these genes producing dwarf phenotypes has been difficult.

Transgenic plants comprising an OsMADS1 transgene are shorter than controls. Therefore, the OsMADS1 gene is useful for producing dwarf plant varieties for a variety of plants including cereal, fruit, and floricultural species.

Synchronizing reproductive growth. Transgenic plants expressing an OsMADS1 transgene flower more synchronously than controls. Therefore, the gene can be used for crops for which synchronized harvesting is economically beneficial, allowing more effective use of mechanized harvesting of fruit species or the production of floricultural species having improved flower quality, for example.

Producing day-neutral plant varieties. Expression of an OsMADS1 transgene in daylength-sensitive (i.e., long-day or short-day) plants at least partially overrides the photoperiod requirement for flowering and can completely override the photoperiod requirement. By introducing such a transgene into a wide variety of photoperiod-sensitive crop species, including, but not limited to rice and soybeans, these plants effectively become day-neutral, permitting multiple crops to be grown per year. For example, flowers can be induced the year-round by introducing the transgene into floricultural species such as chrysanthemum and orchid.

Delaying flowering and fruiting. By suppressing the expression of a native OsMADS1 gene by conventional approaches, e.g., by employing antisense, co-suppression, gene replacement, or other conventional approaches to suppressing plant gene expression, flowering and fruiting can be delayed. Delayed reproductive growth can thereby increase the length of the vegetative growth stage and cause the plants to grow faster, since the energy used for development of flowers and seeds can be saved for vegetative growth. Thus, delaying or eliminating reproductive growth results in a higher yield of vegetable species such as spinach, radish, cabbage, or tree species. In addition, such plants will be more desirable for as garden and street species, since their production of pollen allergens can be reduced or eliminated Overcoming the vernalization requirement. An OsMADS1 gene is useful for overriding the vernalization requirement of certain plant species. Induction of flowering of transgenic plants that constitutively express an OsMADS1 gene thus becomes insensitive to temperature.

Growing plants in space. Plants grown extraterrestrially are preferably insensitive to photoperiod and temperature for flowering. Transgenic plants carrying the OsMADS1 gene would be expected to flower in the extremely abnormal growth conditions found in a space shuttle or space station.

Cloning and analysis of alleles and homologs. The availability of OsMADS1 makes it possible to obtain alleles and homologs of these genes by conventional methods, through the use of nucleic acid and antibody probes and primers, as discussed below.

DEFINITIONS AND METHODS

The following definitions and methods are provided to better define the present invention and to guide those of ordinary skill in the art in the practice of the present invention. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994.

The term "plant" encompasses any plant and progeny thereof. The term also encompasses parts of plants, including seed, cuttings, tubers, fruit, flowers, etc.

A "reproductive unit" of a plant is any totipotent part or tissue of the plant from which one can obtain a progeny of the plant, including, for example, seeds, cuttings, buds, bulbs, somatic embryos, etc.

"Natural photoperiod conditions" are photoperiod (i.e., daylength) conditions as provided by sunlight at a given location, whether under field conditions. A photoperiod provided by artificial lighting but having a daylength approximating that of sunlight would also be considered a natural photoperiod condition.

Nucleic Acids

Nucleic acids useful in the practice of the present invention comprise at least one of the isolated genes disclosed herein, namely OsMADS1, OsMADS5, OsMADS6, OsMADS7, OsMADS8, and NtMADS3, and their alleles, homologs, fragments, and variant forms thereof.

As employed herein, the term MADS gene for example, refers to a plant gene that contains a MADS-box sequence, and preferably also a K-box sequence, and that is associated with one or more of the following phenotypes when expressed as a transgene in transgenic plants: (1) diminished apical dominance (as shown, for example, by dwarf stature) and (2) early flowering, and can also be associated with, for example, (3) altered daylength requirement for flowering; (4) greater synchronization of flowering; and (5) relaxed vernalization requirement. The MADS gene encompasses the respective coding sequences and genomic sequences flanking the coding sequence that are operably linked to the coding sequence, including regulatory elements and/or intron sequences. Also encompassed are alleles and homologs.

The term "native" refers to a naturally-occurring nucleic acid or polypeptide, including a wild-type sequence and an allele thereof.

A "homolog" of a particular MADS gene is a native gene sequence isolated from a plant species other than the species from which the MADS gene was originally isolated and having similar biologically activities, e.g., dwarfism and early flowering.

"Isolated". An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid-purification methods. The term also embraces nucleic acids prepared by recombinant expression in a host cell as well as chemically synthesized nucleic acids.

DNA constructs incorporating an a MADS gene or fragment thereof preferably place the protein-coding sequence under the control of an operably linked promoter that is capable of expression in a plant cell. Various promoters suitable for expression of heterologous genes in plant cells are known in the art, including constitutive promoters, e.g. the cauliflower mosaic virus (CaMV) 35S promoter, which is expressed in many plant tissues, organ- or tissue-specific promoters, and promoters that are inducible by chemicals such as methyl jasminate, salicylic acid, or Safener, for example.

Plant transformation and regeneration. In addition to the methods for plant transformation and regeneration described in the Examples below for making transgenic plants, other well-known methods can be employed.

Fragments, probes, and primers. "fragment " of a MADS nucleic acid according to the present invention is a portion of the nucleic acid that is less than full-length and comprises at least a minimum length capable of hybridizing specifically with the corresponding MADS nucleic acid (or a sequence complementary thereto) under stringent conditions as defined below. The length of such a fragment is preferably at least 15 nucleotides in length, more preferably at least 30 nucleotides, more preferably at least 50 nucleotides, and most preferably at least 100 nucleotides.

A "probe" comprises an isolated nucleic acid attached to a detectable label or reporter molecule well known in the art. Typical labels include radioactive isotopes, ligands, chemiluminescent agents, and enzymes.

"Primers" are short nucleic acids, preferably DNA oligonucleotides 15 nucleotides or more in length, that can be annealed to a complementary target DNA strand by nucleic acid hybridization to form a hybrid between the primer and the target DNA strand, then extended along the target DNA strand by a polymerase, preferably a DNA polymerase. Primer pairs can be used for amplification of a nucleic acid sequence, e.g., by the polymerase chain reaction (PCR) or other nucleic-acid amplification methods well known in the art. PCR-primer pairs can be derived from the sequence of a nucleic acid according to the present invention, for example, by using computer programs intended for that purpose such as Primer (Version 0.5, ©1991, Whitehead Institute for Biomedical Research, Cambridge, Mass.).

Methods for preparing and using probes and primers are described, for example, in Sambrook et al., Molecular Cloning: A Laboratory Manual, 2nd ed., vol. 1–3, ed. Sambrook et al., Cold Spring Harbor Laboratory Press, Cold Spring Harbor, NY, 1989; Current Protocols in Molecular Biology, ed. Ausubel et al., Greene Publishing and Wiley-Interscience, New York, 1987 (with periodic updates); and Innis et al., PCR Protocols: A Guide to Methods and Applications, Academic Press: San Diego, 1990.

Substantial similarity. A first nucleic acid is "substantially similar" to a second nucleic acid if, when optimally aligned (with appropriate nucleotide insertions or deletions) with the other nucleic acid (or its complementary strand), there is nucleotide sequence identity in at least about 75%–90% of the nucleotide bases, and preferably greater than 90% of the nucleotide bases. ("Substantial sequence complementarity" requires a similar degree of sequence complementarity.) Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

Operably linked. A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Techniques for nucleic-acid manipulation are described generally in, for example, Sambrook et al. (1989) and Ausubel et al[]. (1987, with periodic updates).

Preparation of recombinant or chemically synthesized nucleic acids; vectors, transformation, host cells. Large amounts of a nucleic acid according to the present invention can be produced by recombinant means well known in the art or by chemical synthesis.

Natural or synthetic nucleic acids according to the present invention can be incorporated into recombinant nucleic-acid constructs, typically DNA constructs, capable of introduction into and replication in a host cell. Usually the DNA constructs will be suitable for replication in a unicellular host, such as *E. coli* or other commonly used bacteria, but can also be introduced into yeast, mammalian, plant or other eukaryotic cells.

Preferably, such a nucleic-acid construct is a vector comprising a replication system recognized by the host. For the practice of the present invention, well-known compositions and techniques for preparing and using vectors, host cells, introduction of vectors into host cells, etc. are employed, as discussed, *inter alia*, in Sambrook et al., 1989, or Ausubel et al., 1987.

A cell, tissue, organ, or organism into which has been introduced a nucleic acid according to an embodiment of the present invention, such as a recombinant vector, is considered "transformed" or "transgenic." A recombinant DNA construct that is present in a transgenic host cell, particularly a transgenic plant, is referred to as a "transgene." The term "transgenic" or "transformed" when referring to a cell or organism, also includes (1) progeny of the cell or organism and (2) plants produced from a breeding program employing such a "transgenic" plant as a parent in a cross and exhibiting an altered phenotype resulting from the presence of the recombinant DNA construct.

Conventional methods for chemical synthesis of nucleic acids are used, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

Nucleic-Acid Hybridization; "Stringent Conditions"; "Specific". The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989 at 9.52–9.55. See also, Sambrook et al., 1989 at 9.47–9.52, 9.56–9.58; Kanehisa, Nuc. Acids Res. 12:203–213, 1984; and Wetmur and Davidson, J. Mol. Biol. 31:349–370, 1968. According to one embodiment of the invention, "moderate stringency" hybridization conditions are hybridization at 60° C. in a hybridization solution including 6× SSC, 5× Denhardt's reagent, 0.5% SDS, 100 μg/mL denatured, fragmented salmon sperm DNA, and the labeled probe (Sambrook et al., 1989), and "high stringency" conditions are hybridization at 65–68° C. in the same hybridization solution.

Regarding the amplification of a target nucleic-acid sequence (e.g., by PCR) using a particular amplification primer pair, stringent conditions are conditions that permit the primer pair to hybridize only to the target nucleic-acid sequence to which a primer having the corresponding wild-type sequence (or its complement) would bind.

Nucleic-acid hybridization is affected by such conditions as salt concentration, temperature, or organic solvents, in addition to the base composition, length of the complementary strands, and the number of mismatched bases between the hybridizing nucleic acids.

When referring to a probe or primer, the term "specific for (a target sequence)" indicates that the probe or primer hybridizes only to the target sequence in a given sample comprising the target sequence.

Nucleic-acid amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, Innis et al. eds., Academic Press, San Diego, 1990.

In situ hybridization. A number of techniques have been developed in which nucleic-acid probes are used to locate specific DNA sequences on intact chromosomes in situ, a procedure called "in situ hybridization." See, e.g., Pinkel et al., Proc. Natl. Acad. Sci. USA 85:9138–9142, 1988 (regarding fluorescence in situ hybridization), and Lengauer et al., Hum. Mol. Genet. 2:505–512, 1993 (regarding "chromosomal bar codes"). Well-known methods for in situ hybridization and for the preparation of probes or primers for such methods are employed in the practice of the present invention, including direct and indirect in situ hybridization methods.

Methods of obtaining genomic clones, alleles, and homologs. Based upon the availability of the nucleotide sequences of the OsMADS1 gene disclosed herein, other MADS-box genes (e.g., alleles and homologs) and genomic clones corresponding to the OsMADS gene can be readily obtained from a wide variety of plants by cloning methods known in the art.

For example, one or more primer pairs can be used to amplify such alleles or homologs by the polymerase chain reaction (PCR). Alternatively, the disclosed OsMADS1 cDNA or a fragment thereof can be used to probe a cDNA or genomic library made from a given plant species.

Nucleotide-Sequence and Amino-Acid Sequence Variants. "Variant" DNA molecules are DNA molecules containing minor changes to a native, or wild-type, sequence, i.e., changes in which one or more nucleotides of a native sequence are deleted, added, and/or substituted while substantially maintaining wild-type biological activity. Variant DNA molecules can be produced, for example, by standard DNA mutagenesis techniques or by chemically synthesizing the variant DNA molecule. Such variants do not change the reading frame of the protein-coding region of the nucleic acid.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence (i.e., a truncation of the native sequence) and are preferably made in adjacent base pairs. Substitutions, deletions, insertions or any combination thereof can be combined to arrive at a final construct. For the sequences disclosed herein, amino acid substitutions preferably are located outside sequences that are conserved among OsMADS1 and OsMADS5–8 and homologs thereof, such as NtMADS3.

Preferably, variant nucleic acids according to the present invention are "silent" or "conservative" variants. "Silent" variants are variants of a native sequence in which there has been a substitution of one or more base pairs but no change in the amino-acid sequence of the polypeptide encoded by the sequence. "Conservative" variants are variants of a native sequence in which at least one codon in the protein-coding region of the native sequence has been changed, resulting in a conservative change in one or more amino-acid residues of the polypeptide encoded by the nucleic-acid sequence, i.e., an amino-acid substitution. A number of conservative amino-acid substitutions are listed in Table 1. In addition, there can be a substitution (resulting in a net gain or loss) of one or more cysteine residues, thereby affecting disulfide linkages in the encoded polypeptide.

TABLE 1

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those in Table 1, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Polypeptides

The term "MADS protein (or polypeptide)" refers to a protein encoded by an OsMADS gene that has at least about 70% homology with a given native OsMADS1 polypeptide and preferably retains biological activity of the native polypeptide. MADS polypeptide can be isolated from a natural source, produced by the expression of a recombinant MADS nucleic acid, or be chemically synthesized by conventional methods, for example.

Polvpeptide sequence homoloqy. Ordinarily, the polypeptides encompassed by the present invention are at least about 70% homologous to a native polypeptide, preferably at least about 80% homologous, and more preferably at least about 95% homologous. Preferably, such polypeptides also have characteristic structural features and biological activity of the native polypeptide.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated," "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60–90% by weight of a sample is composed of the polypeptide, preferably 95% or more, and more preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other methods known in the art.

Protein purification. The polypeptides of the present invention can be purified by any of the means known in the art. Various methods of protein purification are described, e.g., in Guide to Protein Purification, ed. Deutscher, Meth. Enzymol. 185, Academic Press, San Diego, 1990; and Scopes, Protein Purification: Principles and Practice, Springer Verlag, New York, 1982.

Variant forms of polypeptides; labeling. Variant polypeptides are those in which there have been substitutions, deletions, insertions or other modifications of a native polypeptide sequence. Variant polypeptides substantially retain structural and/or biological characteristics and are preferably silent or conservative substitutions of one or a small number of amino acid residues.

Native polypeptide sequences can be modified by conventional methods, e.g., by acetylation, carboxylation, phosphorylation, glycosylation, ubiquitination, and labeling, whether accomplished by in vivo or in vitro enzymatic treatment of a native polypeptide or by protein synthesis using modified amino acids.

Any of a variety of conventional methods and reagents for labeling polypeptides and fragments thereof can be employed in the practice of the invention. Typical labels include radioactive isotopes, ligands or ligand receptors, fluorophores, chemiluminescent agents, and enzymes. Methods for labeling and guidance in the choice of labels appropriate for various purposes are discussed, e.g., in Molecular Cloning: A Laboratory Manual, 2nd ed., vol. 1–3, ed. Sambrook et al., Cold Spring Harbor Laboratory Press: Cold Spring Harbor, N.Y., 1989; and Current Protocols in Molecular Biology, ed. Ausubel et al., Greene Publishing and Wiley-Interscience: New York, 1987 (with periodic updates).

Polypeptide Fragments. The present invention also encompasses polypeptide fragments that lack at least one residue of a native full-length polypeptide yet retain at least one of the biological activities characteristic of the native polypeptide. For example, the fragment can cause early flowering or dwarf phenotypes when expressed as a transgene in a host plant. An immunologically active fragment of a given full-length polypeptide is capable of raising antibodies specific for the full-length polypeptide in a target immune system (e.g., murine or rabbit) or of competing with the full-length polypeptide for binding to such specific antibodies, and is thus useful in immunoassays for the presence of the native polypeptide in a biological sample. Such immunologically active fragments typically have a minimum size of 7 to 17 amino acids.

Fusion polypeptides. The present invention also provides fusion polypeptides including, for example, heterologous fusion polypeptides, e.g., a fusion between an OsMADS1 polypeptide sequence or fragment thereof and a heterologous polypeptide sequence, e.g., a sequence from a different polypeptide. Such heterologous fusion polypeptides generally exhibit biological properties (such as ligand-binding, catalysis, secretion signals, antigenic determinants, etc.) derived from each of the fused sequences. Fusion partners include, for example, immunoglobulins, beta galactosidase, trpE, protein A, beta lactamase, alpha amylase, alcohol dehydrogenase, yeast alpha mating factor, and various signal and leader sequences which, e.g., can direct the secretion of the polypeptide. Fusion polypeptides can be made, for example, by the expression of recombinant nucleic acids or by chemical synthesis.

Polypeptide sequence determination. The sequence of a polypeptide can be determined by any conventional methods. In order to determine the sequence of a polypeptide, the polypeptide is typically fragmented, the fragments separated, and the sequence of each fragment determined. To obtain fragments of a polypeptide for sequence determination, for example, the polypeptide can be digested with an enzyme such as trypsin, clostripain, or Staphylococcus protease, or with chemical agents such as cyanogen bromide, o-iodosobenzoate, hydroxylamine or 2-nitro-5-thiocyanobenzoate. Peptide fragments can be separated, e.g., by reversed-phase high-performance liquid chromatography (HPLC) and analyzed by gas-phase sequencing, for example.

Antibodies

The present invention also encompasses polyclonal and/or monoclonal antibodies capable of specifically binding to any of the polypeptides disclosed herein. Such antibodies can be produced by any conventional method. "Specific" antibodies are capable of distinguishing a given polypeptide from other polypeptides in a sample. Specific antibodies are useful, for example in purifying a polypeptide from a biological sample; in cloning alleles or homologs of a given gene sequence from an expression library; as antibody probes for protein blots and immunoassays; etc.

For the preparation and use of antibodies according to the present invention, including various antibody labelling and immunoassay techniques and applications, see, e.g., Goding, Monoclonal Antibodies: Principles and Practice, 2d ed, Academic Press, New York, 1986; and Harlow and Lane, Antibodies: A Laboratory Manual, Cold Spring Harbor Laboratory, Cold Spring Harbor, N.Y., 1988. Suitable labels for antibodies include radionuclides, enzymes, substrates, cofactors, inhibitors, fluorescent agents, chemiluminescent agents, magnetic particles and the like.

The invention will be better understood by reference to the following Examples, which are intended to merely illustrate the best mode now known for practicing the invention. The scope of the invention is not to be considered limited thereto, however.

EXAMPLES

EXAMPLE 1
Isolation and Analysis of a MADS-Box Gene from Rice, OsMADS1

Bacterial Strains, Plant Materials, and Plant Transformation. *Escherichia coli* MC1000 (ara, leu, lac, gal, str) was used as the recipient for routine cloning experiments. Rice (*Oryza sativa* L. cv. M201) plants were grown in a growth chamber at 26° C. with 10.5-hr day cycle.

cDNA Library Construction and Molecular Characterization. A cDNA library was constructed using the λZapII vector (Stratagene, La Jolla, Calif.) and poly(A)+mRNA isolated from rice flowers. An adapter containing EcoRI and NotI sites (Pharmacia LKB Biotechnology, Piscataway, N.J.) was used to ligate the vector and cDNA. The library was divided into 20 sublibraries and amplified in an *E. coli* host strain, XL-1 Blue [F'::Tn10 pro+B+, lacIq, (lac Z)MI5/recAJ. endAI, gyrA96 (Nar), thi, hsdR17(rk$^-$, mk$^+$), sup44, reLA1, lac] (Stratagene, La Jolla, Calif.).

Plaque hybridization was performed with $10^5$ plaques that were lifted onto nitrocellulose membranes. The plasmid pBluescript containing the OsMADS1 cDNA was rescued in vivo from the bacteriophage λ using f1 helper phage, R408 (Stratagene, La Jolla, Calif.). Both strands of the cDNA inserts were sequenced by the dideoxynucleotide chain-termination method using double-stranded DNA as a template (Sanger et al., Proc. Natl. Acad. Sci. USA 74:5463–5467, 1977).

Southern and Northern Blot Analyses. Genomic DNA was prepared from two-week-old rice seedlings by the CTAB (cetyltrimethylammonium bromide) method (Rogers and Bendich, Extraction of DNA from plant tissues, In: Gelvin and Schilperoort, eds., Plant Molecular Biology Manual, Kluwer Academic, Dordrecht, Belgium, 1988, pp. A6/1–10). Four $\mu$g of DNA were digested with appropriate restriction enzymes, separated on a 0.7% agarose gel, blotted onto a nylon membrane, and hybridized with a $^{32}$P-labeled probe labeled by the random-priming method (Sambrook et al., Molecular Cloning: A Laboratory Manual, Cold Spring Harbor Laboratory Press, Cold Spring Harbor, N.Y., 1989). Ten $\mu$g of total RNA isolated by the guanidium thiocyanate method were used for the northern analysis (id.).

In situ Localization. Rice flowers were dehydrated with ethanol, fixed (1.4% glutaraldehyde, 2% paraformaldehyde, 50 mM PIPES, pH 7.2), and embedded in paraffin. Eight-$\mu$m sections were attached to gelatin-coated glass slides and hybridized with $^{35}$S-labeled antisense RNA (Cox and Goldberg, Analysis of plant gene expression, In: Shaw, ed., Plant Molecular Biology: A Practical Approach, IRL Press, Oxford, 1988, pp. 1–34). The RNA probe was prepared by in vitro transcription using pBluescript carrying the OsMADS1 cDNA clone as a template The sections were coated with an X-ray emulsion film and exposed for four days. The samples were stained with 0.5% toluidine blue to visualize tissue sections. Photographs were taken with a brightfield microscope.

Results. A cDNA clone, OsMADS1, was isolated by screening a λZapII cDNA library prepared from immature rice flower mRNA using mixed probes of different MADS-box cDNA clones isolated from Arabidopsis (Ma et al., Genes Dev. 5:484–495, 1991; Yanofsky et al., Nature 346:35–39, 1990), Brassica (Mandel et al., Cell 71:133–143, 1992), tobacco (Kempin et al., Plant Physiol. 103:1041–1046, 1933), and tomato (Pnueli et al., Plant J. 1:255–266, 1991).

DNA sequence analysis showed that the rice clone encodes a protein of 257 amino-acid residues (FIG. 1A) SEQ ID NO:1 and SED ID NO:2. The deduced amino-acid sequence contains the conserved MADS-box domain between amino acids 2 and 57 (FIG. 1B) SEQ ID NO:3–9. A second domain present in MADS-box proteins, the "K-box," is located between residues 90 and 143. The OsMADS1 clone appears to be nearly full length, since the estimated transcript length by northern hybridization analysis is similar to that of the cDNA clone. The conserved MADS-box region is located immediately after the start methionine codon in the rice gene, as has been observed in most MADS-box genes. Therefore it is unlikely that the rice clone encodes a truncated protein.

These observations indicate that OsMADS1 is a member of the MADS-box gene family. Among characterized MADS-box proteins, the OsMADS1 amino-acid sequence is most homologous to AP1 (44.4% identity) and SQUA (42.6% identity). In addition, OsMADS1 shows extensive similarity to the functionally anonymous Arabidopsis MADS-box genes AGL2 (56.2% identity) and AGL4 (55.4% identity).

To determine the number of MADS-box genes present in rice, Southern blot analysis was performed. Rice DNA was digested with EcoRI, HindIII, or PstI, fractionated on a 0.7% agarose gel, and hybridized with a probe prepared from the entire OsMADS1 cDNA or an OsMADS1 cDNA probe lacking the conserved MADS-box region. More than ten restriction fragments hybridized with the entire cDNA probe, whereas a single fragment was detected by a probe lacking the conserved MADS-box region. This result indicates that the rice genome contains a large number of genes encoding MADS-box proteins, similar to what is observed in other plant species (Angenent et al., Plant Cell 4:983–993, 1992; Ma, Genes Dev. 5:484–495, 1991; Pnueli et al., Plant J. 1:255–266, 1991; Schmidt et al., Plant Cell 5:729–737, 1993).

Northern blot analyses were conducted to study the expression pattern of the OsMADS1 gene in rice organs. Ten-μg samples of total RNA isolated from leaf and root of two-week-old seedlings, and anther, carpel, and palea/lemma of anthesis-stage flowers was hybridized with the OsMADS1 probe lacking the MADS domain. Ethidium bromide staining of 25S and 18S rRNAs demonstrated equal amounts of RNA loading.

The temporal pattern of OsMADS1 gene expression during rice flower development was studied by Northern blot analysis. Twenty μg of total RNA was isolated from rice flowers at different developmental stages: young inflorescence (panicle size <1 cm), young flowers (panicle size=1 to 6 cm), flowers at the early vacuolated pollen stage, and flowers at the late vacuolated pollen stage. RNA samples were subjected to gel electrophoresis, transferred to membranes, and probed with an OsMADS1 cDNA lacking the conserved MADS-box region in order to avoid cross-hybridization with other MADS-box genes. This probe was selected in order to observe the specific expression pattern of the gene. OsMADS1 transcripts were present in the palea/lemma and carpel of anthesis-stage flowers, but not in the anther or vegetative organs (e.g., leaf or root). The gene was active during the young inflorescence stage and expression continued into the early and late vacuolated pollen stages.

The localization of the OsMADS1 transcript in rice flowers and phenotypes of transgenic tobacco plants expressing OsMADS1 was studied by in situ hybridization experiments using longitudinal sections of young inflorescence, and cross sections of the upper and lower rice flower at the vacuolated pollen stage (anther, filament, flower primordia, lemma, ovary, palea, sheath, and sterile lemma). 8-μm sections were hybridized with $^{35}$S-labeled antisense RNA lacking the MADS-box domain. The sections were coated with an X-ray emulsion film and exposed for four days. The samples were stained with 0.5% toluidine blue to visualize tissue sections which show negative expression of the gene. A sense probe did not show any hybridization above the background level. These in situ experiments revealed that the OsMADS1 transcript was uniformly present in young flower primordia during early flower development and later became localized in certain floral organs. In young inflorescences, strong hybridization signals were detected in flower primordia but not in other tissues. In vacuolated pollen-stage flowers, OsMADS1 mRNA was detected in the palea, lemma, and ovary. However, the hybridization signal was not uniform in these tissues. In particular, the tissues near the palea/lemma junction and the palea tissues covered by lemma exhibited little or no expression of the gene. No significant signal was observed in the anther, filament, or sterile lemma. These results indicate that the OsMADS1 gene is preferentially expressed in certain floral tissues, as has been observed with most MADS-box genes.

The expression pattern of the OsMADS1 gene closely resembled that of AP1 and SQUA (Juijser et al., EMBO J. 11:1239–1249, 1992; Mandel et al., Nature 360:273–277, 1992). Flower-specific expression is also common for other MADS-box genes (Angenant et al., Plant Cell 4:983–993, 1992; Jack et al., Cell 68:683–697, 1992; Kempin et al., Plant Physiol. 103:1041–1046, 1993; Ma et al., Genes Dev. 5:484–495, 1991; Mandel et al., Nature 360:273–277, 1992; Pnueli et al., Plant J. 1:255–266, 1991; Schmidt et al., Plant Cell 5:729–737, 1993; Sommer et al., EMBO J. 9:605–613, 1990; Tsuchimoto et al., Plant Cell 5:843–853, 1993).

Nine independent clones that contain the conserved MADS-box have been isolated.

EXAMPLE 2

Expression of OsMADS1 in Transgenic Tobacco Plants Results in Early Flowering and Dwarf Phenotypes Bacterial Strains, Plant Materials, and Plant Transformation. *Agrobacterium tumefaciens* LBA4404 (Hoekema et al., Nature 303:179–181, 1983), containing the Ach5 chromosomal background and a disarmed helper-Ti plasmid pAL4404, was used for transformation of tobacco plants (*Nicotiana tabacum* L. cv. Petit Havana SR1) by the co-cultivation method (An et al., Binary Vectors, In: Gelvin and Schilperoort, eds., Plant Molecular Biology Manual, Kluwer Academic, Dordrecht, Belgium, 1988, pp. A3/1–19). Transgenic plants were maintained in a greenhouse.

Results. Ectopic expression of floral homeotic genes alters floral organ identity in homologous (Kempin et al., Plant Physiol. 103:1041–1046, 1993; Mizukami and Ma, Cell 71:119–131, 1992; Pnueli et al., Plant Cell 6:163–173, 1994; Tsuchimoto et al., Plant Cell 5:843–853, 1993) and heterologous systems (Mandel et al., Cell 71:133–143, 1992).

In order to characterize the functional role of OsMADS1, tobacco plants were used as a heterologous expression system. The cDNA clone encoding the entire OsMADS1 coding region was placed under the control of cauliflower mosaic virus 35S promoter (Benfey and Chua, Science 250:959–966, 1990) and transcript 7 terminator using a binary vector pGA748, which is a derivative of pGA643 (An et al., Binary Vectors, In: Gelvin and Schilperoort, eds., Plant Molecular Biology Manual, Kluwer Academic, Dordrecht, Belgium, 1988, pp. A3/1–19). The chimeric molecule (pGA1209) was transferred to tobacco (*Nicotiana tabacum* cv. Petite Havana SR1) plants using the Agrobacterium-mediated Ti plasmid vector system (An et al., Binary Vectors, In: Gelvin and Schilperoort, eds., Plant Molecular Biology Manual, Kluwer Academic, Dordrecht, Belgium, 1988, pp. A3/1–19). Twenty independent transgenic plants were studied.

Most of the primary transgenic plants flowered much earlier than control plants that were transformed with the Ti plasmid vector alone. The transgenic plants were significantly shorter and contained several lateral branches. These phenotypes were inherited to the next generation as a dominant Mendelian trait.

Northern-blot analysis was conducted on seven transgenic plants which displayed the early flowering phenotype. Transcripts from a control plant and seven different transgenic plants exhibiting the early flowering and dwarf phenotypes were sampled for preparation of total RNA from leaves and flowers. Twenty μg of total RNA was hybridized with $^{32}$P-labeled probe prepared from the OsMADS1 cDNA lacking the MADS domain. The results showed that all of the transgenic plants accumulated the OsMADS1 transcripts in both vegetative and reproductive organs. Although there were significant differences in gene expression among the transgenic plants, the relative expression level was similar between the leaf and flower. Transgenic plant #7, which displayed the most severe symptoms, accumulated the highest level of the transcript. Plants #4, #5, #6, with less severely altered phenotypes, expressed the gene at reduced levels, indicating that the level of OsMADS1 RNA correlated with phenotype.

However, progeny from the same parent displayed phenotypic variation. The basis of this variation was investigated with T1 offspring of the transgenic plant #2 in which the transgene segregates as a single locus. OsMADS1 homozygotes were much shorter (34.2±0.8 cm) compared to heterozygotes (51.6±1.4 cm), while the wild-type tobacco plants were 119.8±2.2 cm. The homozygotes flowered two days earlier than the heterozygotes and eight days earlier than wild type plants. This result indicates that the variation was due to gene dosage.

Table 2 summarizes characteristics of four independently transformed plants from the T1 generation. Seeds were collected from selfed fruits of the primary transgenic plants (T0 generation). The seeds were germinated in a peat pellet and grown for two weeks at 16 hr light/8 hr dark cycles under fluorescent lights. The resulting T1 plants were grown under greenhouse conditions. Ten to twenty plants were analyzed for each transgenic line. Standard errors are shown in parentheses. Progeny carrying the transgenes were identified by visually scoring T2 seedlings for kanamycin resistance. The kanamycin-sensitive segregants were used as controls (C). Days to flowering include the time from seed germination to the first anthesis. Height and internode length were measured when fruits were fully developed (90 days post-germination). The data in Table 2 show that transgenic plants flowered 7 to 10 days earlier than wild-type plants and their height and internode length appear to be significantly reduced.

TABLE 2

Comparison of phenotypes of transgenic plants with non-transformed control

| Transgenic Line (#) | Days to Flowering | Height (cm) | Internode Length (cm) |
|---|---|---|---|
| 1 | 53.0 (2.0) | 61.2 (5.8) | 5.7 (0.5) |
| 2 | 54.2 (0.3) | 47.6 (1.9) | 4.6 (0.2) |
| 3 | 53.0 (0.4) | 64.3 (3.5) | 5.8 (0.3) |
| 4 | 50.6 (0.9) | 40.2 (4.4) | 3.5 (0.3) |
| C | 61.0 (0.2) | 119.8 (2.2) | 9.0 (0.3) |

EXAMPLE 3
Ectopic Expression of OsMADS1 Overcomes Photoperiod Dependency of Long-Day and Short-Day Flowering Plants Transgenic plants that constitutively express a rice MADS-box gene, OsMADS1, flower earlier than untransformed controls, indicating that the OsMADS1 gene is involved in controlling flowering time.

Nicotiana sylvestris, a long-day flowering plant, and N. tabacum cv. Maryland Mammoth, a short-day flowering plant, were transformed with pGA1209, which contains a kanamycin selectable marker and a chimeric fusion between the CaMV 35S promoter and OsMADS1-coding region by the Agrobacterium-mediated co-cultivation method (An et al., Binary vectors, In Gelven and Schilperoort, eds., Plant Molecular Biology Manual A3:1–19, Kluwer Academic Publishers, Dordrecht, Belgium, 1988). Transgenic plants were regenerated on kanamycin-containing culture medium. Transgenic plants were selfed and kanamycin-resistant T1 offspring were used for the entire experiment. Plants were grown under either a short-day growth condition (10 hr light) or a long-day growth condition (16 hr light).

Total RNA was isolated from leaves of transgenic plants by the guanidium thiocyanate method (Sambrook et al., Molecular Cloning: A Laboratory Manual, Cold Spring Harbor Press, Cold Spring Harbor, N.Y., 1989). Twenty μg of total RNA was electrophoresed on a 1.3% agarose gel, blotted onto a nylon membrane, and hybridized with a $^{32}$P-labeled probe prepared by the random-priming method (Sambrook et al., Molecular Cloning: A Laboratory Manual, Cold Spring Harbor Press, Cold Spring Harbor, N.Y., 1989).

Transgenic N. sylvestris flowered earlier than untransformed controls under the permissive flowering (long-day) conditions. Plants were short and branched with clustered flowers compared to the controls. These phenotypes are similar to day-neutral transgenic tobacco plants expressing the OsMADS1 gene.

In order to confirm whether the phenotypes were stably inherited, five independently transformed transgenic N. sylvestris plants were chosen for further studies. T1 offspring were selected on a kanamycin-containing medium and the seedlings were grown under the long-day (16 hr daylength) or short-day (10 hr daylength) growth conditions. Under the long-day condition, the transgenic plants flowered 7–11 days earlier than the controls which flowered in 106 days after seed germination. The data are summarized in

TABLE 3

Ectopic expression of OsMADS1 in Nicotiana sylvestris

| Transgenic Plant | Short Day Conditions | | Long Day Conditions | |
|---|---|---|---|---|
| | Days to Flowering | Height (cm) | Days to Flowering | Height (cm) |
| 1 | 102 | 62 | 98 | 68 |
| 2 | 85 | 35 | 95 | 45 |
| 3 | 146 | 65 | 99 | 72 |
| 4 | 84 | 36 | 96 | 46 |
| 5 | 97 | 52 | 97 | 52 |
| control | — | — | 106 | 85 |

The transgenic plants also showed short and branched phenotypes. When the transgenic plants were grown under the short-day (non-permissive) condition, they flowered within 85–146 days, whereas the untransformed control plants did not flower (Table 3). Transgenic lines 2 and 4 flowered earlier under the short-day condition and line 3 flowered under the long-day condition, while lines 1 and 5 flowered at approximately the same time.

In order to confirm whether the phenotypes observed resulted from the expression of the OsMADS1 gene, OsMADS1 transcripts in transgenic N. sylvestris were studied by northern blotting using as a probe an OsMADS1 cDNA lacking the MADS-box domain. Since a constitutive promoter was used for expression of the gene, it was expected that the transcript was present in all the plant parts, since the 35S promoter-driven OsMADS1 transcript is almost equally expressed in both leaves and flowers. Total RNA was prepared from fully expanded leaves of five transgenic lines exhibiting early flowering under both permissive and non-permissive conditions and an untransformed N. sylvestris control, and the level of OsMADS1 transcript in each line was measured. All of the transgenic plants expressed the OsMADS1 transcript. The amount of the transcript was in direct correlation with the degree of the phenotypes. Transgenic lines 2 and 4, which flowered earliest, expressed the highest level of the OsMADS1 mRNA, whereas line 3, which flowered latest among the five transgenic lines, expressed the lowest level of the OsMADS1 mRNA. Transgenic lines with intermediate phenotypes expressed intermediate levels of the transcript.

These results suggest that expression of the OsMADS1 gene caused a change in the timing of flowering in a long-day flowering plant *N. sylvestris*. Under permissive long-day conditions, transgenic plants flowered earlier than controls. Under non-permissive short-day conditions, expression of the transgene overcame the day-length requirement for flowering. The degree of the phenotype correlated with the level of expression of the transgene, especially under short-day conditions. Interestingly, transgenic plants expressing a high level of the OsMADS transcript flowered earlier under short-day conditions than under long-day conditions, the latter being permissive flowering conditions for untransformed *N. sylvestris*.

Expression of the OsMADS1 gene can also overcome the day-length requirement of a short-day flowering plant, *N. tabacum* cv. Maryland Mammoth. Transgenic plants were obtained that expressed the OsMADS1 chimeric molecule. As observed with the day-neutral or long-day plant, transformation of the OsMADS1 chimeric gene into the short-day plant resulted in early flowering and bushy phenotypes under a short-day (permissive) condition.

Three independently transformed lines of transgenic *N. tabacum* cv. Maryland Mammoth plants that express OsMADS1 and exhibit early flowering under both permissive and non-permissive conditions were further studied. T1 offspring were selected on kanamycin-containing medium and grown under a short-day (10 hr daylength; permissive) or a long-day (16 hr daylength; non-permissive) conditions Under permissive conditions, T1 transgenic lines flowered 16–21 days earlier than untransformed controls, which flowered in 119 days (Table 4). The height of the transgenic plants was less than one-half that of the control plants. Under non-permissive conditions, transgenic plants flowered in 202–206 days, whereas the control did not flower (Table 4).

RNA blot analysis (using as a probe an OsMADS1 cDNA lacking the MADS-box domain) showed that all three lines expressed the OsMADS1 transcript. Again, the degree of the phenotype correlated with the level of OsMADS1 transgene expression. Thus, expression of the OsMADS1 gene also overcame the day-length requirement of a short-day plant.

TABLE 4

Ectopic expression of OsMADS1 in *Nicotiana tabacum* cv. Maryland Mammoth

| Transgenic Plant | Short Day Conditions | | Long Day Conditions | |
|---|---|---|---|---|
| | Days to Flowering | Height (cm) | Days to Flowering | Height (cm) |
| 1 | 98 | 61 | 202 | 102 |
| 2 | 103 | 65 | 206 | 105 |
| 3 | 98 | 63 | 203 | 104 |
| control | 119 | 143 | — | — |

Ectopic expression of OsMADS1 overcomes the day-length dependence of flowering. The effect was more evident when the gene was highly expressed. The fact that OsMADS1 overcomes the day-length dependence of both short-day and long-day plants indicates that a common gene product controls the timing of flowering in both short-day and long-day plants. It is likely that, under natural conditions, expression of the OsMADS1 gene is tightly controlled by environmental conditions and the flowering process is initiated by triggering OsMADS1 gene expression.

EXAMPLE 4

Isolation and Analysis of a MADS-Box Gene from Nicotiana tabacum, NtMADS3

A homolog of OsMADS1 was isolated from a *Nicotiana tabacum* cDNA library constructed using the λZapII vector (Stratagene, La Jolla, Calif.) and poly(A)+mRNA isolated from tobacco flowers as described above. Using the OsMADS1 cDNA as a probe under moderately stringent hybridization conditions (60° C.) in an initial screen, several tobacco MADS-box genes were obtained.

In a secondary screen to identify a tobacco homolog of OsMADS1, the OsMADS1 cDNA was split into two parts between the MADS-box and K-box sequences and used to probe the tobacco MADS-box cDNAs. Only one of the cDNAs, NtMADS3, hybridized to both halves of the OsMADS1 sequence, i.e., to the half containing the MADS-box sequence and the half containing the OsMADS1 K-box sequence.

To further confirm the identity of NtMADS3 as a homolog of OsMADS1, all isolated tobacco MADS-box genes obtained in the primary screening of the tobacco flower library were placed under the control of the 35S promoter and transformed into *N. tabacum* as described above. Only transgenic *N. tabacum* expressing the NtMADS3 transgene exhibited early flowering and dwarf phenotypes.

The nucleotide sequence of the NtMADS3 cDNA was obtained and compared to OsMADS1. NtMADS3 is 945 bp long and contains an open reading frame of 242 amino acid residues (FIG. 2) SEQ ID NO:10 and SEQ ID NO:11. The deduced NtMADS3 polypeptide sequence showed 56% homology with that of OsMADS1, with 96.5% homology in the MADS-box and 77.3w homology in the K-box (FIG. 3) SEQ ID NO:2 and SEQ ID NO:11.

EXAMPLE 5

Isolation and Characterization of Three Rice MADS-Box Genes That Control the Timing of Flowering—OsMADS6, OsMADS7, and OsMADS8

Experimental procedures

Bacterial strains, plant materials, and plant transformation. *Escherichia coli* JM 83 was used as the recipient for routine cloning experiments. *Agrobacterium tumefaciens* LBA4404 (Hoekema et al., Nature 303:179–181 1983) containing the Ach5 chromosomal background and a disarmed helper-Ti plasmid pAL4404 was used for transformation of tobacco plants (*N. tabacum* L. cv. Xanthi) by the cocultivation method (An et al., in: Plant Molecular Biology Manual, Gelvin and Schilperoort, eds., Kluwer Academic, Dordrecht, Belgium, pp. A3/1–19, 1988). Transgenic tobacco plants were maintained under greenhouse conditions. Rice (*Oryza sativa* L. cv. M201) plants were grown in a growth chamber 29° C. with a 10.5 h day cycle.

Library screening and sequence analysis. cDNA libraries were constructed using λZapII vector (Stratagene) and mRNA was prepared from rice flowers at floral primordial stage when the length of the panicles was below 1 cm. Hybridization was performed with $10^5$ plaques using a $^{32}$P-labeled probe of the OsMADS1 coding region. The cDNA insert was rescued in vivo using an f1 helper phage, R408 (Stratagene). Both strands of the cDNA were sequenced by the dideoxy-nucleotide chain termination method using a double-strand DNA as a template (Sanger et al. Proc. Natl. Acad. Sci. USA 74:5463–5467, 1977). Protein-sequence similarity was analyzed by the IG Suite software package (Intelligenetics Co., Mountain View, Calif.) and the NCBI non-redundant protein database on the international network.

DNA and RNA blot analyses. Genomic DNA was isolated by the cetyltrimethylammonium bromide (CTAB) method from two-week-old rice seedlings grown hydroponically (Rogers and Bendich, Plant Molecular Biology Manual Kluwer Academic, Dordrecht, Belguim, pp. A6/1-101988). Eight μg of genomic DNA was digested with the appropriate restriction enzymes, separated on a 0.7% agarose gel, blotted onto a nylon membrane, and hybridized with a $^{32}$P-labeled probe for 16 h at 65° C., followed by a wash with a solution containing 2× SSC and 0.5% SDS for 20 min at 65° C., followed by a wash with a solution of 0.1X SSC and 0.1% SDS for 15 min at the same temperature. Total RNA was isolated by the guanidium thiocyanate method (Sambrook et al., 1989). Leaf and root samples were harvested from the two-week-old seedlings. Floral organ samples were obtained by dissecting late vacuolated-stage flowers under a dissecting microscope. Twenty-five μg of total RNA was fractionated on a 1.3% agarose gel as described previously (Sambrook et al., 1989). After RNA transfer onto a nylon membrane, the resulting blot was hybridized in a solution containing 0.5 M NaPO$_4$ (pH 7.2), 1 mM EDTA, 1% BSA, and 7% SDS for 20 h at 60° C. (Church and Gilbert, Proc. Natl. Acad. Sci. USA 81:1191–1195, 1984). After hybridization, the blot was washed twice with a solution containing 0.1× SSPE and 0.1% SDS for 5 min at room temperature followed by two washes of the same solution at 60° C. for 15 min.

Mapping procedures. An F11 recombinant inbred population consisting of 164 lines derived from a cross between Milyang 23 and Gihobyeo was used to construct a molecular map. Three-week old leaf tissue was harvested from over one hundred seedlings for each F11 line and bulked for DNA extraction. DNA was digested with restriction enzymes (BamHI, DraI, EcoRI, HindIII, EcoRV, ScaI, XbaI, KpnI) and 8 μg per lane was used to make mapping filters. DNA blotting and hybridization were performed as described above. Linkage analysis was performed using Mapmaker Version 3.0 (Lander et al., Genomics 12:174–181, 1987) on a Macintosh Power PC 8100/80AV. Map units (cM) were derived using the Kosambi function (Kosambi, Ann. Eugen. 12:172–175, 1994).

Results

Isolation of rice cDNA clones encoding MADS box protein. Three cDNA clones were isolated by screening a λZapII cDNA library that was prepared from rice floral primordia using OsMADS1 cDNA as a probe (described above). These clones were designated OsMADS6, OsMADS7, and OsMADS8. DNA sequence analysis showed that these clones are 1180 bp to 1259 bp long and encode putative proteins 248 to 250 amino acid residues long (OsMADS6: FIG. 4, SEQ ID NO:12 and SEQ ID NO:13; OsMADS7: FIG. 5, SEQ ID NO:14 and SEQ ID NO:15; OsMADS8: FIG. 6, SEQ ID NO:16 and SEQ ID NO:17). The 5'-untranslated region of the OsMADS8 cDNA contains eight repeats of the GGA sequence and the 5'-untranslated region of OsMADS7 cDNA contains six repeats of the GGT sequence, a so-called microsatellite (Browne and Litt, Nucl. Acids Res. 20:141, 1991; Stalings, Genomics 17:890–891, 1992). Such repeat sequences have been observed in other rice MADS-box genes (Chung et al., Plant Mol. Biol. 26:657–665, 1994).

The MADS-box domain of the cDNA clone is located between the 2nd and 57th amino acids of each protein (FIG. 4, SEQ ID NO:12 and SEQ ID NO:13; FIG. 5, SEQ ID NO:14 and SEQ ID NO:15; FIG. 6, SEQ ID NO:16 and SEQ ID NO:17). Comparison with other MADS-box genes shows that this region is the most conserved. A second conserved domain, the K box, is located between residues 91 and 156 in OsMADS6 and between the residues 95 and 160 in both OsMADS7 and OsMADS8 (FIG. 4, SEQ ID NO:12 and SEQ ID NO:13; FIG. 5, SEQ ID NO:14 and SEQ ID NO:15; FIG. 6, SEQ ID NO:16 and SEQ ID NO:17). These genes contain two variable regions, the I-region between the MADS and K boxes, and the C-region downstream of the K box (Purugganan et al., Genetics 140:345–356, 1995). The structure of the proteins encoded by OsMADS6, OsMADS7, and OsMADS8 is therefore typical of the plant MADS-box gene family.

Based on the amino-acid sequence similarity of the entire coding region, the OsMADS6, OsMADS7, and OsMADS8 proteins can be grouped into the AGL2 family, which includes AGL2, AGL4 and AGL6 of Arabidopsis (Ma et al., Genes Dev. 5:484–495, 1991), ZAG2 and ZAG5 of maize (Mena et al., Plant J. 8:845–854, 1995), FBP2 of petunia (Angenent et al., Plant J. 5:33–44, 1994), TM5 of tomato (Pnueli et al., Plant Cell 6:175–186, 1994), OM1 of orchid (Lu et al., Plant Mol. Biol. 23:901–904, 1993), and OsMADS1 of rice. Among these genes, the OsMADS6 protein was most homologous to ZAG3 (84w homology) and ZAG5 (82% homology), while the OsMADS7 and OsMADS8 proteins were most homologous to OM1 (61% and 65%, respectively) and FBP2 (60% and 64% homology, respectively). OsMADS6, OsMADS7, and OsMADS8 proteins had 50% amino acid sequence homology to OsMADS1.

Alignment of the OsMADS6, OsMADS6, and OsMADS8 proteins with other members of the AGL2 family showed that the MADS-box (FIG. 7A, SEQ ID NOS:2, 13, 15, and 17–29), K-box (FIG. 7B, SEQ ID NOS:2, 13, 15, 17, and 30–41), and C-terminal end regions (FIG. 7C, SEQ ID NOS:2, 13, 15, 17, and 42–53) share significant sequence homologies (FIG. 7). The MADS-box region of OsMADS6 is 100% identical to that of ZAG3 and differs from the MADS-box region of OsMADS7 and OsMADS8 in two positions; the 22nd and 50th amino acid serines in OsMADS6 are replaced with alanine and asparagine, respectively, in both OsMADS7 and OsMADS8. The MADS-box sequences of OsMADS6, OsMADS7, and OsMADS8 share at least 89% identity to the MADS-box sequences of other AGL2 proteins. The sequence homology in the K box region is lower compared to the MADS box region, but still significant. These regions of OsMADS6, OsMADS7, and OsMADS8 are at least 43% identical to other members of the family, whereas the homology was much lower with distantly related MADS-box proteins such as AG, AP3, and PI. The sequence homology at the C-terminal end was much lower. However, there are two blocks of conserved regions at the end of the proteins, and these AGL2-specific sequences were not found in other MADS box proteins. FIG. 7 shows the structure of MADS-box proteins, including the MADS-box region, I region, K-box region, C-terminal region, and C-terminal end region.

RNA blot analysis. There are a large number of MADS-box genes in the rice genome. Genomic DNA blot analyses were conducted to identify a region that would not cross hybridize with other MADS box genes. Rice genomic DNA was digested with EcoRI, HindIII, or PstI, fractionated on a 0.8% agarose gel, and hybridized with the gene specific probes located at the 3' region of each cDNA. The 300 bp PstI-EcoRI fragment, which is located at the C-terminal region of OsMADS6, hybridized to single DNA fragments.

Likewise, the 280 bp PstI-EcoRI fragment of OsMADS7 and 220 bp NheI-EcoRI fragment of OsMADS8 were shown to be gene-specific regions.

RNA blot analyses of the OsMADS6, OsMADS7, and OsMADS8 transcripts in rice were conducted. Ten μg of total RNA isolated from roots and leaves of two-week-old seedlings, and paleas/lemmas, anthers, and carpels of late vacuolated-stage flowers were hybridized with the gene-specific probes. The OsMADS6 transcript was detectable primarily in carpels and also weakly in palea and lemma of late vacuolated pollen-stage flowers. However, the transcript was not detectable in anthers or vegetative organs. This expression pattern is similar to that of OsMADS1. Spatial expression patterns of the OsMADS7 and OsMADS8 clones were different from that of OsMADS6. Transcripts of both clones were detectable primarily in carpels and also weakly in anthers. This expression patter is similar to those of OsMADS3 and OsMADS4 (Chung et al., Plant Science 109:45–56, 1995; Kang et al., Plant Mol. Biol. 29:1–10, 1995).

The temporal expression pattern of Os[]MADS genes during flower development was also examined. Twenty-five μg of total RNA isolated from rice flowers at three different developmental stages were used for detection of the OsMADS gene expression. The stages examined were: young flowers at the panicle size (1 to 5 cm); flowers at the early vacuolated pollen stage; and flowers at the late vacuolated pollen stage. Ethidium bromide staining of 25S and 17S rRNAs were shown to demonstrate equal amounts of RNA loading. During flower development the OsMADS6 and OsMADS7 genes were strongly expressed at the young flower stage and expression gradually decreased as the flower further developed to the mature flower stage. The expression of OsMADSB was weak at the young flower stage and expression gradually increased as the flower developed.

Chromosomal mapping of the OsMADS genes. An F11 recombinant inbred population of rice was used to locate the OsMADS genes on a genetic map. C-terminal DNA fragments that were shown to be unique to each OsMADS gene were used. These experiments revealed that OsMADS6 is located on the long arm of chromosome 2, OsMADS7 on the long arm of chromosome 8, and OsMADS8 on the long arm of chromosome 9 (FIG. 8). We also mapped two additional rice MADS box genes, OsMADS2 and OsMADS3. It was shown that OsMADS2 is a member of GLOBOSA family. This gene is located on the long arm of chromosome 1 (FIG. 8). OsMADS3 is a rice homolog of Arabidopsis AGAMOUS and is located on the short arm of chromosome 1.

Ectopic expression. The functional roles of the three rice MADS box genes were studied using tobacco plants as a heterologous expression system. The cDNA clones were placed under the control of the CaMV 35S promoter and transcript 7 terminator using the binary vector pGA748 (An et al., in: Plant Molecular Biology Manual, Gelvin and Schilperoort, eds., Kluwer Academic, Dordrecht, Belgium, pp. A3/1–19, 1988). The chimeric molecules were transferred to tobacco plants using a kanamycin-resistance marker and an Agrobacterium-mediated Ti plasmid vector system. Ten independent T1 transgenic plants were regenerated to avoid any artifacts. Some of the primary transgenic plants were shorter and bloomed earlier than control plants, which were transformed with the Ti plasmid vector alone, while others showed normal growth RNA-blot analyses of transgenic plants expressing the OsMADS6, OsMADS7, and OsMADS8 transcripts were performed in order to investigate the expression level of the transgenes. Ten μg of total RNAs isolated from young leaves of the tobacco transgenic plants were hybridized with gene-specific probes. In order to minimize the variation due to the stage of development, young leaves at anthesis of the first flower were used for RNA isolation. It was found that plants showing the early flowering phenotype expressed higher levels of the transgene compared with transgenic plants exhibiting a weak or no early flowering phenotype. The transgenic lines OsMADS6-2, -4, -5, and -7 accumulated higher levels of the transgene transcript and flowered earlier.

Transgenic lines OsMADS7–5, -9, and -10, and OsMADS8–4 and -5 accumulated higher levels of the transgene transcript and flowered earlier.

Transgenic lines (T2 generation) that expressed OsMADS6, OsMADS7, and OsMADS8 and displayed the most severe phenotypes were selected to examine the inheritance of the characteristics. The results showed that the early flowering phenotypes was co-inherited with the kanamycin resistance gene to the next generation. The transgenic plant line OsMADS6-7 flowered an average of 10 days earlier that control plants and was 30 cm shorter than controls. Similarly, both OsMADS7–10 and OsMADS8–5 flowered an average of nine days earlier than control plants and were significantly shorter than wild-type control plants.

Discussion

The three additional rice MADS-box genes that were isolated are probably involved in controlling the timing of flowering. The deduced amino acid sequences of the gene products showed a high homology to the AGL2 family proteins. The homology was extensive, covering the entire protein. It was observed that the AGL2 family of proteins could be further divided into several subgroups depending on the protein sequence similarity in the K box and the two variable regions (Theiβen and Saedler, Curr. Opinion in Genet. and Dev. 5:628–639, 1995). Our results (see FIG. 7) show that OsMADS6 belongs to the AGL6 subfamily and OsMADS7 and OsMADS8 both belong to the FBP2 subfamily.

The sequence identity of these genes suggest that they share similar biological function. Using the co-suppression approach (Angenent et al., Plant J. 5:33–44, 1994), it was found that suppression of FBP2 expression in petunia flowers resulted in aberrant flowers with modified whorl two, three, and four organs. The flower possessed a green corolla, petaloid stamens, and dramatically altered carpel structure. Therefore, FBP2 is apparently involved in the determination of the central parts of the generative meristem. Using an antisense RNA approach, TM5 has been observed to have similar effects on the development of the three whorls. As discussed above, transgenic plants overexpressing OsMADS1 exhibited early flowering and dwarf phenotypes, indicating that OsMADS[]i is involved in controlling the timing of flowering. No morphological alteration of the floral organs was observed. These observations suggest that the FBP2 and TM5 genes function differently than the OsMADS1 gene. Interestingly, the length of the OsMADS6, OsMADS7, and OsMADS8 proteins is similar to OsMADS1 and AP1 proteins, but much longer than the FBP2 and TM5 proteins. Therefore, it is possible that the additional amino acid sequences encoded by the OsMADS genes are responsible for controlling the timing of flowering RNA blot analyses showed that the OsMADS6, OsMADS7, and OsMADS8 genes were expressed specifically in flowers, which coincides with the expression of genes of the AGL2 family. This indicates that the genes of the AGL2 family function primarily during the flower development. The expression of the OsMADS genes started at the early stage of the flower development and extended into the later stages of flower development, indicating that the OsMADS genes play critical roles during the early stages and continue to function as the flower further develops. Such expression patterns were also observed from other AGL2 members, including AGL2, AGL4, FBP2, TM5 (Angenent et al., Plant Cell 4:983–993, 1992; Ma et al., Genes Dev. 5:484–495, 1991; Pnueli et al., Plant J. 1:255–266, 1991), and OsMADS1. However, not all members of the AGL2 family are expressed at early stages of development. The OM1 transcript is detectable only after flower organs have fully developed (Lu et al., Plant Mol. Biol. 23:901–904, 1993). In mature flowers, the OsMADS6 gene was preferentially expressed in the carpels and palea/lemma. Similar expression patterns were found in OsMADS1, AP1, and SQUA, suggesting a possibility that they belong to a functionally similar group. The FBP2 and TM5 genes are expressed in the whorls 2, 3 and 4 (Pnueli et al., Plant Cell 6:175–186, 1994; Angenent et al., Plant Cell 4:983–993, 1992). Unlike most dicots, rice flowers contain a single perianth, the palea/lemma, which more closely resembles a sepal than a petal. The palea/lemma contains chlorophyll and remains attached to mature seeds. Therefore, expression of FBP2 homologs in dicots is expected to be restricted in sepals and petals. The OsMADS7 and OsMADS8 genes were expressed in the inner two whorls, coinciding with the expected expression pattern.

OsMADS6, OsMADS7, and OsMADS8 mapped to rice chromosomes 2, 8, and 9, respectively. The EF-1 gene, which controls the timing of flowering in rice, is located on chromosome 10, and the Se genes, which determine photoperiod sensitivity, are located on chromosomes 6 or 7 (Khush and Kinoshita, in *Rice Biotechnology*, Khush and Toennesson, eds., C.A.B. International and International Rice Research Institute, pp. 93–106, 1991). Therefore, it is evident that none of the early flowering MADS-box genes are linked to previously mapped markers that are involved in controlling the timing of flowering. The relationship of OsMADS6, OsMADS7, and OsMADS8 to other genes involved in the timing of flowering, such as E-1, E-2, E-3, lf-1 and lf-2, can be resolved when these genes are mapped.

We also mapped the OsMADS2 gene, which is a member of the GLOBOSA family OsMADS2 is located between RG109 and EstI-2 on chromosome 1. It was previously reported that the RG109 and the EstI-2 markers are tightly linked to the semidwarf gene, sd-1, which is important for controlling the culm length and flowering time (Cho et al., Theor. Appl. Genet. 89:54–59, 1994; Causse, Genetics 138:1251–1274, 1994).

To elucidate the functions of the rice MADS-box genes, we have generated transgenic tobacco plants that express a chimeric fusion between the CaMV 35S promoter and an OsMADS cDNA. OsMADS6, OsMADS7, and OsMADS8 genes caused early flowering and dwarf phenotypes when strongly expressed in transgenic plants, as does OsMADS1.

EXAMPLE 6
Isolation and Characterization of a Rice MADS-Box Gene, OsMADS5, That Belongs to the AGL2 Gene Fami 1Y
Materials and Methods Bacterial strains, plant materials, and plant transformation. *Escherichia coli* JM 83 was used as a recipient for routine cloning experiments. *Agrobacterium tumefaciens* LBA4404 (Hoekema et al., Nature 303:179–181, 1983) containing the Ach5 chromosomal background and a disarmed helper-Ti plasmid pAL4404 was used for transformation of tobacco plants (*N. tabacum* L. cv. Xanthi) by the cocultivation method (An et al., in: Plant Molecular Biology Manual, Gelvin and Schilperoort, eds., Kluwer Academic, Dordrecht, Belgium, pp. A3/1–19, 1988). Transgenic plants were maintained under greenhouse conditions. Rice (*Oryza sativa* L. cv. M201) plants were grown in a growth chamber at 290C with a 10.5 h day cycle.

Library screening and sequence analysis. cDNA libraries were constructed from mRNA prepared from rice flowers at floral primordia and young flowers (length of the panicle was below 1 cm). Hybridization was performed with 105 plaques using a 32P-labeled probe of the OsMADS1 coding region. The cDNA insert was rescued in vivo using an fl helper phage, R408 (Stratagene). Both strands of the cDNA were sequenced by the dideoxy-nucleotide chain termination method using a double-strand DNA as a template.

Analysis of protein sequence. Protein sequence similarity was analyzed by the IG Suite software package (Intelligentics Co., Mountain View, Calif.) and the NCBI non-redundant protein database on the international network.

DNA and RNA blot analyses. Total genomic DNA was isolated by the CTAB method from two-week-old rice seedlings grown hydroponically (Rogers and Bendich, Plant Molecular Biology Manual, Kluwer Academic, Dordrecht, Belgium, pp. A6/1–10, 1988). Total DNA (8 μg) was digested with the appropriate restriction enzymes, separated on a 0.7% agarose gel, blotted onto a nylon membrane, and hybridized with a $^{32}$p-labeled probe for 16 h at 65° C. in a solution containing 6×SSC and 0.2w BLOTTO (Sambrook et al., 1989). After hybridization, the blot was washed with a solution of 0.1× SSC and 0.1% SDS for 15 min at the same temperature. Total RNA was isolated by the guanidium thiocyanate method (Sambrook et al., 1989). Leaf and root samples were harvested from the two-week-old seedlings. Floral organ samples were obtained by dissecting late vacuolated stage flowers under a dissecting microscope. Twenty-five mg of total RNA was fractionated on a 1.3% agarose gel as described previously (Sambrook, et al., 1989). After RNA transfer onto a nylon membrane, the blot was hybridized in a solution containing 0.5 M NaPO$_4$ (pH 7.2), 1 mM EDTA, 1% BSA, and 7% SDS for 20 h at 60° C. (Church and Gilbert, Proc. Natl. Acad. Sci. USA 81:1191–1195, 1984). After hybridization, the blot was washed twice with a solution containing 0.1×SSPE and 0.1 SDS for 5 min at room temperature followed by two washes of the same solution at 60° C. for 15 min.

Results

Isolation of a rice cDNA clone encoding a MADS-box protein. A cDNA clone, OsMADS5, was isolated by screening a λZapII cDNA library prepared from floral primordia of rice using OsMADS1 cDNA as a probe, as described above. DNA sequence analysis shows that OsMADS5 contains 1027 nucleotides and encodes a putative protein 225 amino acid residues in length (FIG. 9). SEQ ID NO:54 and SEQ ID NO:55. The 5'-untranslated region of OsMADS5 cDNA contains four repeats of the GAGAGAGA sequence and of the GAGA sequence, a so-called microsatellite (Browne and Litt, Nucl. Acids Res. 20:141, 1991; Stalings, Genomics 17:890–891, 1992). The conserved MADS-box domain is located between amino acid residues 2 and 57 (FIG. 9) SEQ ID NO:54 and the conserved K-box domain is located between residues 94 and 154 (FIG. 9, SEQ ID NO:54). The OsMADS5 gene contains two variable regions, the I-region between the MADS-box and K-box regions, and the C-region downstream of the K box (Purugganan et al., Genetics 140:345–356, 1995). These observations suggest that OsMADS5 encodes a protein having the typical structure of the plant MADS-box gene family. Based on amino-acid sequence similarity, the OsMADS5 protein was grouped into the AGL2 family, which includes AGL2, AGL4 and AGL6 of *A. thaliana*, DEFH24 of *A. majus*, FBP2 of petunia, ZAG3 and ZAG5 of maize (Mena et al., 1995), TM5 of tomato, OM1 of orchid, and OsMADS1 of rice (FIG. 10) MADS-box: SEQ ID NOS:56 [consensus], 55 [OsMADS5], 2 [OsMADS1], and 18–29 [other MADS-box genes]; I-region: SEQ ID NOS:57 [consensus], 55 [OsMADS5], 2 [OsMADS1], and 58–69 [other MADS-box genes]; and K-box: SEQ ID NOS:70 [consensus], 55 [OsMADS5], 2 [OsMADS1], and 30–41 [other MADS-box genes]. Among these genes, the OsMADS5 protein was most homologous to the OsMADS1 protein: 72% sequence identity in the entire sequence, 94.6% in the MADS-box, and 83% in the K-box.

RNA blot analysis. Because there are a large number of MADS box genes in the rice genome, it was necessary to identify a region of the OsMADS5 cDNA that does not cross hybridize with other MADS-box genes. Rice genomic DNA was digested with HindIII, PstI, or SacI, fractionated on a 0.8% agarose gel, and hybridized with the 260-bp EcoRI-HindIII fragment located at the 3'-end region of the OsMADS5 cDNA. The DNA blot analysis showed that a single DNA fragment of the genomic DNA specifically hybridized with the 260 bp EcoRI-HindIII fragment.

RNA blot analyses were conducted using the 260-bp OsMADS5-specific region. Ten μg of total RNA isolated from roots and leaves of two-week-old seedlings, and paleas/lemmas, anthers, and carpels of late vacuolated-stage flowers were hybridized with the OsMADS5-specific probe. The OsMADS5 transcript was detectable primarily in anthers and also weakly in carpels of late vacuolated pollen-stage flowers. However, the transcript was not detectable primarily in the palea/lemma or vegetative organs.

The temporal expression of OsMADS5 during flower development was also studied. Twenty-five μg of total RNA was isolated from rice organs at the following stages of development: leaves of two-week-old seedlings, roots of two-week-old seedlings; young flowers at the panicle size (1–5 cm); flowers at the early vacuolated pollen stage; and flowers at the late vacuolated pollen stage. (Ethidium bromide staining of 25S and 17S rRNAs demonstrated equal amounts of RNA loading.) The OsMADS5 gene was strongly expressed at the young flower stage and expression gradually decreased as the flowers further developed to the mature flower stage.

Ectopic expression. The functional role of OsMADS5 were studied using tobacco plants as a heterologous expression system. The pGA1348 plasmid carrying the OsMADS5 cDNA under the control of the CaMV 35S promoter was transferred into tobacco plants using a binary Ti vector and Agrobacterium. Twenty independent T1 transgenic plants were studied to avoid any artifact. The resulting primary transgenic plants of OsMADS5 tended to be shorter and bloomed earlier than control plants transformed with the Ti plasmid vector alone. These phenotypes were inherited by subsequent generations as a dominant Mendelian trait.

RNA blot analysis was conducted with on ten independent T1 transgenic plants that expressed the OsMADS5 transcript. Ten μg of total RNA isolated from young leaves of each transgenic plant was fractionated by gel electrophoresis, transferred to a membrane, and hybridized with the OsMADS5-specific probe. The result showed that transgenic plant #9, which displayed the most severe phenotype, likewise accumulated the highest level of the transcript. These plants (T2 generation) flowered about 10 days earlier and were about 35 cm shorter than wild-type Xanthi tobacco control plants.

Discussion

We have isolated and characterized a rice MADS box gene, OsMADS5. The deduced amino-acid sequence of the gene product showed a high homology to MADS-box proteins. The OsMADS5 clone appears to be nearly full length, since the cDNA has a long 5'-untranslated region and a poly-A tail in the C-terminal end. In addition, the estimated transcript length as determined by RNA blot analysis was similar to that revealed by sequence analysis. OsMADS5 was grouped into the AGL2 gene family based on the sequence similarity in the MADS-box domain. Sequence comparison suggests that the MADS-box sequences of these regulatory genes have co-evolved with the rest of the genes (Theißen and Saedler, Curr. Opinion in Genet. and Dev. 5:628–639, 1995). The AGL2 family can be further divided into several groups on the basis of protein sequence similarity in the K-box and the two variable regions (FIG. 10). Overall, OsMADS5 is most homologous to OsMADS1, and these two genes can be separated from the other proteins of the AGL-2 family.

RNA blot analysis showed that the OsMADS5 gene was expressed specifically in the flower, a specificity coinciding with that of genes of the AGL2 family, which likely function primarily during the flower development. The OsMADS5 gene was highly expressed in flowers at an early stage of development and the expression level gradually decreased as the flower further developed. In mature flowers, the genes was preferentially expressed in anthers, and also expressed very weakly in carpels. This expression pattern is different from that of the OsMADS1 gene which is highly expressed in the late floral stage and in the palea/lemma and carpel. This indicates that a high amino acid homology between MADS-box genes does not necessarily indicate a similarity in their expression patterns.

To elucidate the functions of the two MADS box genes of rice, we have generated transgenic tobacco plants expressing a chimeric fusion between the CaMV 35S promoter and the OsMADS5 cDNA. Transgenic plants showed early-flowering and dwarf phenotypes. Both the early-flowering and the dwarf phenotype were stronger in plants that were grown under natural sunlight than those grown under artificial illumination, suggesting that such phenotypes are affected by environmental cues such as light and temperature.

It is commonly believed that one MADS-box gene is involved in determining flower initiation in each plant species. Mutations of AP1 of Arabidopsis or SQUA of Antirrhinum led to alteration of flower initiation. In addition, ectopic expression of rice OsMADS1 or Arabidopsis AP1 resulted in early flowering. We have shown that more than one MADS-box gene is involved in controlling flower development of rice.

All publications and published patent documents cited in this specification are incorporated herein by reference to the same extent as if each individual publication or patent application was specifically and individually indicated to be incorporated by reference.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

SEQUENCE LISTING (1) GENERAL INFORMATION:

(iii) NUMBER OF SEQUENCES: 70

(2) INFORMATION FOR SEQ ID NO: 1:

(i) SEQUENCE CHARACTERISTICS:
       (A) LENGTH: 1141 base pairs
       (B) TYPE: nucleic acid
       (C) STRANDEDNESS: double stranded
       (D) TOPOLOGY: linear (xi) SEQUENCE DESCRIPTION: SEQ ID NO:1:

```
AAAACTAGCT TGCAAAGGGG ATAGAGTAGT AGAGAGAGAG AGAGAGGAGA GGAGGAGGAA      60

GAAG                                                                  64

ATG GGG AGG GGG AAG GTG GAG CTG AAG CGG ATC GAG AAC AAG ATC AGC      112
Met Gly Arg Gly Lys Val Glu Leu Lys Arg Ile Glu Asn Lys Ile Ser
                  5                  10                  15

CGG CAG GTG ACG TTC GCC AAG CGC AGG AAC GGC CTG CTC AAG AAG GCC      160
Arg Gln Val Thr Phe Ala Lys Arg Arg Asn Gly Leu Leu Lys Lys Ala
             20                  25                  30

TAC GAG CTC TCC CTC CTC TGC GAC GCC GAG GTC GCC CTC ATC ATC TTC      208
Tyr Glu Leu Ser Leu Leu Cys Asp Ala Glu Val Ala Leu Ile Ile Phe
         35                  40                  45

TCC GGC CGC GGC CGC CTC TTC GAG TTC TCC AGC TCA TCA TGC ATG TAC      256
Ser Gly Arg Gly Arg Leu Phe Glu Phe Ser Ser Ser Ser Cys Met Tyr
     50                  55                  60

AAA ACC TTG GAG AGG TAC CGC AGC TGC AAC TAC AAC TCA CAG GAT GCA      304
Lys Thr Leu Glu Arg Tyr Arg Ser Cys Asn Tyr Asn Ser Gln Asp Ala
 65                  70                  75                  80

GCA GCT CCA GAA AAC GAA ATT AAT TAC CAA GAA TAC CTG AAG CTG AAA      352
Ala Ala Pro Glu Asn Glu Ile Asn Tyr Gln Glu Tyr Leu Lys Leu Lys
                 85                  90                  95

ACA AGA GTT GAA TTT CTT CAA ACC ACA CAG AGA AAT ATT CTT GGT GAG      400
Thr Arg Val Glu Phe Leu Gln Thr Thr Gln Arg Asn Ile Leu Gly Glu
             100                 105                 110

GAT TTG GGC CCA CTA AGC ATG AAG GAG CTG GAG CAG CTT GAG AAC CAG      448
Asp Leu Gly Pro Leu Ser Met Lys Glu Leu Glu Gln Leu Glu Asn Gln
         115                 120                 125

ATA GAA GTA TCC CTC AAA CAA ATC AGG TCA AGA AAG AAC CAA GCA CTG      496
Ile Glu Val Ser Leu Lys Gln Ile Arg Ser Arg Lys Asn Gln Ala Leu
     130                 135                 140

CTT GAT CAG CTG TTT GAT CTG AAG AGC AAG GAG CAA CAG CTG CAA GAT      544
Leu Asp Gln Leu Phe Asp Leu Lys Ser Lys Glu Gln Gln Leu Gln Asp
145                 150                 155                 160

CTC AAC AAA GAC TTG AGG AAA AAG TTA CAG GAA ACC AGT GCA GAG AAT      592
Leu Asn Lys Asp Leu Arg Lys Lys Leu Gln Glu Thr Ser Ala Glu Asn
                 165                 170                 175

GTG CTC CAT ATG TCC TGG CAA GAT GGT GGT GGG CAC AGC GGT TCT AGC      640
Val Leu His Met Ser Trp Gln Asp Gly Gly Gly His Ser Gly Ser Ser
             180                 185                 190

ACT GTT CTT GCT GAT CAG CCT CAT CAC CAT CAG GGT CTT CTC CAC CCT      688
Thr Val Leu Ala Asp Gln Pro His His His Gln Gly Leu Leu His Pro
         195                 200                 205

CAC CCA GAT CAG GGT GAC CAT TCC CTG CAG ATT GGG TAT CAT CAC CCT      736
His Pro Asp Gln Gly Asp His Ser Leu Gln Ile Gly Tyr His His Pro
     210                 215                 220
```

```
CAT GCT CAC CAT CAC CAG GCC TAC ATG GAC CAT CTG AGC AAT GAA GCA         784
His Ala His His His Gln Ala Tyr Met Asp His Leu Ser Asn Glu Ala
225                 230                 235                 240

GCA GAC ATG GTT GCT CAT CAC CCC AAT GAA CAC ATC CCA TCC GGC TGG         832
Ala Asp Met Val Ala His His Pro Asn Glu His Ile Pro Ser Gly Trp
                245                 250                 255

ATA TGA                                                                 838
Ile

TGTGTGTGTT CAGTTCAGGC TTCAGGCTTC AGAGAAGCCA ATGCAAACAG TGTCCTGTAA       898

TCCAGTAATT ACAGGGCATA TGAATGTAA TGTAATGTAA TCCCTGATCT ATATTTTGCT        958

AAGTACGTGC GTGCTCTCTT ACGACCTTCT CCCCCAAACA GTTAATCAGG GGAATAATAA      1018

TTTCGTTTGA TGCACGTACT GTATGTCTGT ATCTGTCACT GTATCGTAGG ACCGTCCATG      1078

TATAACAATT TCCGTTTTGG ATGTGGTAAC AATTAATTGG CACTTAAATT TATATTTGTG      1138

ATG                                                                   1141
```

(2) INFORMATION FOR SEQ ID NO: 2:

(i) SEQUENCE CHARACTERISTICS:
        (A) LENGTH: 257 amino acid residues
        (B) TYPE: amino acid
        (D) TOPOLOGY: linear (xi) SEQUENCE DESCRIPTION: SEQ ID NO:2:

```
Met Gly Arg Gly Lys Val Glu Leu Lys Arg Ile Glu Asn Lys Ile Ser
                5                  10                  15

Arg Gln Val Thr Phe Ala Lys Arg Arg Asn Gly Leu Leu Lys Lys Ala
             20                  25                  30

Tyr Glu Leu Ser Leu Leu Cys Asp Ala Glu Val Ala Leu Ile Ile Phe
         35                  40                  45

Ser Gly Arg Gly Arg Leu Phe Glu Phe Ser Ser Ser Cys Met Tyr
 50                  55                  60

Lys Thr Leu Glu Arg Tyr Arg Ser Cys Asn Tyr Asn Ser Gln Asp Ala
 65                  70                  75                  80

Ala Ala Pro Glu Asn Glu Ile Asn Tyr Gln Tyr Leu Lys Leu Lys
                 85                  90                  95

Thr Arg Val Glu Phe Leu Gln Thr Thr Gln Arg Asn Ile Leu Gly Glu
            100                 105                 110

Leu Ser Met Asp Leu Gly Pro Lys Glu Leu Glu Gln Leu Glu Asn Gln
            115                 120                 125

Ile Glu Val Ser Leu Lys Gln Ile Arg Ser Arg Lys Asn Gln Ala Leu
130                 135                 140

Leu Asp Gln Leu Phe Asp Leu Lys Ser Lys Glu Gln Gln Leu Gln Asp
145                 150                 155                 160

Leu Asn Lys Asp Leu Arg Lys Lys Leu Gln Glu Thr Ser Ala Glu Asn
                165                 170                 175

Val Leu His Met Ser Trp Gln Asp Gly Gly His Ser Gly Ser Ser
            180                 185                 190

Thr Val Leu Ala Asp Gln Pro His His Gln Gly Leu Leu His Pro
        195                 200                 205

His Pro Asp Gln Gly Asp His Ser Leu Gln Ile Gly Tyr His His Pro
    210                 215                 220

His Ala His His His Gln Ala Tyr Met Asp His Leu Ser Asn Glu Ala
225                 230                 235                 240
```

```
Ala Asp Met Val Ala His His Pro Asn Glu His Ile Pro Ser Gly Trp
                245                 250                 255
Ile
```

(2) INFORMATION FOR SEQ ID NO: 3:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:3:

```
Gly Arg Gly Lys Val Glu Leu Lys Arg Ile Glu Asn Lys Ile Ser Arg
                 5                  10                  15

Gln Val Thr Phe Ala Lys Arg Arg Asn Gly Leu Leu Lys Lys Ala Tyr
                20                  25                  30

Glu Leu Ser Leu Leu Cys Asp Ala Glu Val Ala Leu Ile Ile Phe Ser
                35                  40                  45

Gly Arg Gly Arg Leu Phe Glu Phe
50                  55
```

(2) INFORMATION FOR SEQ ID NO: 4:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:4:

```
Gly Arg Gly Arg Val Gln Leu Lys Arg Ile Glu Asn Lys Ile Asn Arg
                 5                  10                  15

Gln Val Thr Phe Ser Lys Arg Arg Ala Gly Leu Leu Lys Lys Ala His
                20                  25                  30

Glu Ile Ser Val Leu Cys Asp Ala Glu Val Ala Leu Val Val Phe Ser
                35                  40                  45

His Lys Gly Lys Leu Phe Glu Tyr
50                  55
```

(2) INFORMATION FOR SEQ ID NO: 5:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:5:

```
Gly Arg Gly Lys Val Gln Leu Lys Arg Ile Glu Asn Lys Ile Asn Arg
                 5                  10                  15

Gln Val Thr Phe Ser Lys Arg Arg Gly Gly Leu Leu Lys Lys Ala His
                20                  25                  30

Glu Leu Ser Val Leu Cys Asp Ala Glu Val Ala Leu Ile Val Phe Ser
                35                  40                  45

Asn Lys Gly Lys Leu Phe Glu Tyr
50                  55
```

(2) INFORMATION FOR SEQ ID NO: 6:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:6:

Gly Arg Gly Lys Ile Glu Ile Lys Arg Ile Glu Asn Thr Thr Asn Arg
                  5                   10                  15

Gln Val Thr Phe Cys Lys Arg Arg Asn Gly Leu Leu Lys Lys Ala Tyr
                 20                  25                  30

Glu Leu Ser Val Leu Cys Asp Ala Glu Val Ala Leu Ile Val Phe Ser
                 35                  40                  45

Ser Arg Gly Arg Leu Tyr Glu Tyr
        50                  55

(2) INFORMATION FOR SEQ ID NO: 7:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:7:

Gly Arg Gly Lys Ile Glu Ile Lys Arg Ile Glu Asn Ile Thr Asn Arg
                  5                   10                  15

Gln Val Thr Phe Cys Lys Arg Arg Asn Gly Leu Leu Lys Lys Ala Tyr
                 20                  25                  30

Glu Leu Ser Val Leu Cys Asp Ala Glu Val Ala Leu Val Val Phe Ser
                 35                  40                  45

Ser Arg Gly Arg Leu Tyr Glu Tyr
        50                  55

(2) INFORMATION FOR SEQ ID NO: 8:

(i) SEQUENCE CHARACTERISTICS:
        (A) LENGTH: 56 amino acids
        (B) TYPE: amino acid
        (D) TOPOLOGY: linear (xi) SEQUENCE DESCRIPTION: SEQ ID NO:8:

Gly Gly Gly Arg Val Gln Leu Lys Arg Ile Glu Asn Gln Thr Asn Arg
                  5                   10                  15

Gln Val Thr Tyr Ser Lys Arg Arg Asn Gly Leu Phe Lys Lys Ala His
                 20                  25                  30

Glu Leu Thr Val Leu Cys Asp Ala Arg Val Ser Ile Ile Met Phe Ser
                 35                  40                  45

Ser Ser Asn Lys Leu His Glu Tyr
        50                  55

(2) INFORMATION FOR SEQ ID NO: 9:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:9:

Ala Arg Gly Lys Ile Gln Ile Lys Arg Ile Glu Asn Gln Thr Asn Arg
                  5                   10                  15

Gln Val Thr Tyr Ser Lys Arg Arg Asn Gly Leu Phe Lys Lys Ala His
                 20                  25                  30

Glu Leu Ser Val Leu Cys Asp Ala Lys Val Ser Ile Ile Met Ile Ser
                 35                  40                  45

Ser Thr Gln Lys Leu His Glu Tyr
        50                  55

(2) INFORMATION FOR SEQ ID NO: 10:

(i) SEQUENCE CHARACTERISTICS:
        (A) LENGTH: 945 base pairs
        (B) TYPE: nucleic acid
        (C) STRANDEDNESS: double stranded
        (D) TOPOLOGY: linear (xi) SEQUENCE DESCRIPTION: SEQ ID NO:10:

```
CCGGCCGCTG AAAAA                                                         15

ATG GGA AGG GGT AGG GTT GAG CTT AAG AGA ATA GAG AAC AAG ATC AAC          63
Met Gly Arg Gly Arg Val Glu Leu Lys Arg Ile Glu Asn Lys Ile Asn
1               5                   10                  15

AGG CAA GTG ACC TTC GCT AAG AGA AGA AAT GGA CTT TTG AAA AAA GCT          111
Arg Gln Val Thr Phe Ala Lys Arg Arg Asn Gly Leu Leu Lys Lys Ala
                20                  25                  30

TAT GAG CTT TCT GTT CTT TGT GAT GCT GAG GTT GCT CTC ATC ATC TTC          159
Tyr Glu Leu Ser Val Leu Cys Asp Ala Glu Val Ala Leu Ile Ile Phe
            35                  40                  45

TCC AAT AGG GGA AAA CTG TAC GAG TTC TGC AGT AGC TCT AGC ATG CTC          207
Ser Asn Arg Gly Lys Leu Tyr Glu Phe Cys Ser Ser Ser Ser Met Leu
        50                  55                  60

AAG ACA TTA GAG AGG TAC CAG AAG TGC AAC TAC GGA GCA CCA GAG ACC          255
Lys Thr Leu Glu Arg Tyr Gln Lys Cys Asn Tyr Gly Ala Pro Glu Thr
65                  70                  75                  80

AAT ATA TCC ACA CGA GAA GCA CTG GAA ATA AGT AGC CAA CAA GAA TAC          303
Asn Ile Ser Thr Arg Glu Ala Leu Glu Ile Ser Ser Gln Gln Glu Tyr
                85                  90                  95

TTG AAG CTT AAA GCA CGT TAC GAA GCA TTA CAG CGA TCA CAG AGA AAT          351
Leu Lys Leu Lys Ala Arg Tyr Glu Ala Leu Gln Arg Ser Gln Arg Asn
            100                 105                 110

CTT CTT GGT GAA GAT CTT GGC CCT TTG AAT AGC AAG GAA CTT GAA TCA          399
Leu Leu Gly Glu Asp Leu Gly Pro Leu Asn Ser Lys Glu Leu Glu Ser
        115                 120                 125

CTT GAG AGG CAG CTT GAT ATG TCA CTG AAA CAG ATT CGA TCA ACT CGG          447
Leu Glu Arg Gln Leu Asp Met Ser Leu Lys Gln Ile Arg Ser Thr Arg
130                 135                 140

ACT CAG TTA ATG TTG GAT CAA CTT ACA GAT CTT CAG AGA AAG GAA CAT          495
Thr Gln Leu Met Leu Asp Gln Leu Thr Asp Leu Gln Arg Lys Glu His
145                 150                 155                 160

GCA TTA AAC GAA GCA AAC AGA ACC TTG AAA CAA AGG TTG ATG GAA GGA          543
Ala Leu Asn Glu Ala Asn Arg Thr Leu Lys Gln Arg Leu Met Glu Gly
                165                 170                 175

AGC CAA CTA AAT CTG CAG TGG CAA CAA AAT GCA CAA GAT ATG GGC TAC          591
Ser Gln Leu Asn Leu Gln Trp Gln Gln Asn Ala Gln Asp Met Gly Tyr
            180                 185                 190

GGC CGG CAA ACA ACT CAA ACT CAG GGC GAT GGC TTT TTT CAT CCT TTG          639
Gly Arg Gln Thr Thr Gln Thr Gln Gly Asp Gly Phe Phe His Pro Leu
        195                 200                 205

GAA TGT GAA CCC ACT TTG CAA ATT GGG TAT CAG AAT GAT CCA ATA ACA          687
Glu Cys Glu Pro Thr Leu Gln Ile Gly Tyr Gln Asn Asp Pro Ile Thr
    210                 215                 220

GTA GGA GGA GCA GGG CCC AGT GTG AAT AAC TAC ATG GCT GGC TGG TTG          735
Val Gly Gly Ala Gly Pro Ser Val Asn Asn Tyr Met Ala Gly Trp Leu
225                 230                 235                 240

CCT TGA                                                                  741
Pro

AATTAAGCTC ATTTCCGATA AGATTGATTA TATAAACATA TGCTCAATGT TTTTCCTATC       801

ATAAACACTC TCCTAATTTG TGTTATATGT TGTTTGCCGA ATTCTGGACT AATTTGGGAT       861
```

```
CCATAAGACA GACCCGTTAT TGTTACTTAA TCATAAACTA GATTTCCCTG AGTGACTAAT    921

CACTAAAGCT TATTACTTTC CTCC                                          945
```

(2) INFORMATION FOR SEQ ID NO: 11:

(i) SEQUENCE CHARACTERISTICS:
        (A) LENGTH: 241 amino acid residues
        (B) TYPE: amino acid
        (D) TOPOLOGY: linear (xi) SEQUENCE DESCRIPTION: SEQ ID NO:11:

```
Met Gly Arg Gly Arg Val Glu Leu Lys Arg Ile Glu Asn Lys Ile Asn
  1               5                  10                  15

Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ala Leu Ile Ile Phe
             35                  40                  45

Ser Asn Arg Gly Lys Leu Tyr Glu Gly Cys Ser Ser Ser Met Leu
 50                  55                  60

Lys Thr Leu Glu Arg Tyr Gln Lys Cys Asn Tyr Gly Ala Pro Glu Thr
 65                  70                  75                  80

Asn Ile Ser Thr Arg Glu Ala Leu Glu Ile Ser Ser Gln Gln Glu Tyr
                 85                  90                  95

Leu Lys Leu Lys Ala Arg Tyr Glu Ala Leu Gln Arg Ser Gln Arg Asn
                100                 105                 110

Leu Leu Gly Glu Asp Leu Gly Pro Leu Asn Ser Lys Glu Leu Glu Ser
                115                 120                 125

Leu Glu Arg Gln Leu Asp Met Ser Leu Lys Gln Ile Arg Ser Thr Arg
130                 135                 140

Thr Gln Leu Met Leu Asp Gln Leu Thr Asp Leu Gln Arg Lys Glu His
145                 150                 155                 160

Ala Leu Asn Glu Ala Asn Arg Thr Leu Lys Gln Arg Leu Met Glu Gly
                165                 170                 175

Ser Gln Leu Asn Leu Gln Trp Gln Gln Asn Ala Gln Asp Met Gly Tyr
                180                 185                 190

Gly Arg Gln Thr Thr Gln Thr Gln Gly Asp Gly Phe Phe His Pro Leu
            195                 200                 205

Glu Cys Glu Pro Thr Leu Gln Ile Gly Tyr Gln Asn Asp Pro Ile Thr
210                 215                 220

Val Gly Gly Ala Gly Pro Ser Val Asn Asn Tyr Met Ala Gly Trp Leu
225                 230                 235                 240

Pro
```

(2) INFORMATION FOR SEQ ID NO: 12:

(i) SEQUENCE CHARACTERISTICS:
        (A) LENGTH: 1043 base pairs
        (B) TYPE: nucleic acid
        (C) STRANDEDNESS: double stranded
        (D) TOPOLOGY: linear (xi) SEQUENCE DESCRIPTION: SEQ ID NO:12:

```
TACCCGCGGG AATCGTTCGA TCGATCGGGC GAG                                 33

ATG GGG AGG GGA AGA GTT GAG CTG AAG CGC ATC GAG AAC AAG ATC AAC      81
Met Gly Arg Gly Arg Val Glu Leu Lys Arg Ile Glu Asn Lys Ile Asn
              5                  10                  15
```

| | | | | | | | | | | | | | | |
|---|---|---|---|---|---|---|---|---|---|---|---|---|---|---|
| AGG | CAG | GTC | ACC | TTC | TCC | AAG | CGC | CGC | AAC | GGC | CTC | CTC | AAG AAG GCC | 129 |
| Arg | Gln | Val | Thr | Phe | Ser | Lys | Arg | Arg | Asn | Gly | Leu | Leu | Lys Lys Ala | |
| | | | 20 | | | | 25 | | | | | 30 | | |
| TAC | GAG | CTG | TCC | GTT | CTC | TGC | GAC | GCC | GAG | GTC | GCG | CTC | ATC ATC TTC | 177 |
| Tyr | Glu | Leu | Ser | Val | Leu | Cys | Asp | Ala | Glu | Val | Ala | Leu | Ile Ile Phe | |
| | | 35 | | | | | 40 | | | | | 45 | | |
| TCC | AGC | CGC | GGC | AAG | CTC | TAC | GAG | TTC | GGC | AGC | GCC | GGC | ATA ACA AAG | 225 |
| Ser | Lys | Ser | Arg | Gly | Leu | Tyr | Glu | Phe | Gly | Ser | Ala | Gly | Ile Thr Lys | |
| 50 | | | | | | 55 | | | | | 60 | | | |
| ACT | TTA | GAA | AGG | TAC | CAA | CAT | TGT | TGC | TAC | AAT | GCT | CAA | GAT TCC AAC | 273 |
| Thr | Leu | Glu | Arg | Tyr | Gln | His | Cys | Cys | Tyr | Asn | Ala | Gln | Asp Ser Asn | |
| 65 | | | | 70 | | | | | 75 | | | | 80 | |
| AAT | GCA | CTT | TCT | GAA | ACT | CAG | AGT | TGG | TAC | CAT | GAA | ATG | TCA AAG TTG | 321 |
| Asn | Ala | Leu | Ser | Glu | Thr | Gln | Ser | Trp | Tyr | His | Glu | Met | Ser Lys Leu | |
| | | | | 85 | | | | | 90 | | | | | 95 |
| AAA | GCA | AAA | TTT | GAA | GCT | TTG | CAG | CGC | ACT | CAA | AGG | CAC | TTG CTT GGG | 369 |
| Lys | Ala | Lys | Phe | Glu | Ala | Leu | Gln | Arg | Thr | Gln | Arg | His | Leu Leu Gly | |
| | | | 100 | | | | | 105 | | | | | 110 | |
| GAG | GAT | CTT | GGA | CCA | CTC | AGC | GTC | AAA | GAA | TTG | CAG | CAG | CTG GAG AAA | 417 |
| Glu | Asp | Leu | Gly | Pro | Leu | Ser | Val | Lys | Glu | Leu | Gln | Gln | Leu Glu Lys | |
| | | | 115 | | | | | 120 | | | | | 125 | |
| CAG | CTT | GAA | TGT | GCA | CTA | TCA | CAG | GCG | AGA | CAG | AGA | AAG | ACG CAA CTG | 465 |
| Gln | Leu | Glu | Cys | Ala | Leu | Ser | Gln | Ala | Arg | Gln | Arg | Lys | Thr Gln Leu | |
| | 130 | | | | | 135 | | | | | 140 | | | |
| ATG | ATG | GAA | CAG | GTG | GAG | GAA | CTT | CGC | AGA | AAG | GAG | CGT | CAG CTG GGT | 513 |
| Met | Met | Glu | Gln | Val | Glu | Glu | Leu | Arg | Arg | Lys | Glu | Arg | Gln Leu Gly | |
| 145 | | | | | 150 | | | | | 155 | | | | 160 |
| GAA | ATT | AAT | AGG | CAA | CTC | AAG | CAC | AAG | CTC | GAG | GTT | GAA | GGT TCC ACC | 561 |
| Glu | Ile | Asn | Arg | Gln | Leu | Lys | His | Lys | Leu | Glu | Val | Glu | Gly Ser Thr | |
| | | | | 165 | | | | | 170 | | | | | 175 |
| AGC | AAC | TAC | AGA | GCC | ATG | CAG | CAA | GCC | TCC | TGG | GCT | CAG | GGC GCC GTG | 609 |
| Ser | Asn | Tyr | Arg | Ala | Met | Gln | Gln | Ala | Ser | Trp | Ala | Gln | Gly Ala Val | |
| | | | 180 | | | | | 185 | | | | | 190 | |
| GTG | GAG | AAT | GGC | GCC | GCA | TAC | GTG | CAG | CCG | CCG | CCA | CAC | TCC GCG GCC | 657 |
| Val | Glu | Asn | Gly | Ala | Ala | Tyr | Val | Gln | Pro | Pro | Pro | His | Ser Ala Ala | |
| | | 195 | | | | | 200 | | | | | 205 | | |
| ATG | GAC | TCT | GAA | CCC | ACC | TTG | CAA | ATT | GGG | TAT | CCT | CAT | CAA TTT GTG | 705 |
| Met | Asp | Ser | Glu | Pro | Thr | Leu | Gln | Ile | Gly | Tyr | Pro | His | Gln Phe Val | |
| 210 | | | | | 215 | | | | | 220 | | | | | |
| CCT | GCT | GAA | GCA | AAC | ACT | ATT | CAG | AGG | AGC | ACT | GCC | CCT | GCA GGT GCA | 753 |
| Pro | Ala | Glu | Ala | Asn | Thr | Ile | Gln | Arg | Ser | Thr | Ala | Pro | Ala Gly Ala | |
| 225 | | | | 230 | | | | | 235 | | | | 240 | |
| GAG | AAC | AAC | TTC | ATG | CTG | GGA | TGG | GTT | CTT | TGA | | | | 786 |
| Glu | Asn | Asn | Phe | Met | Leu | Gly | Trp | Val | Leu | | | | | |
| | | | | 245 | | | | 250 | | | | | | |

GCTAAGCAGC CATCGATCAG CTGTCAGAAG TTGGAGCTAA TAATAAAAGG GATGTGGAGT 846

GGGCTACATG TATCTCGGAT CTCTCTGCGA GCCACCTAAT GGTCTTGCGT GGCCCTTTAA 906

TCTGTATGTT TTTGTGTGTA AGCTACTGCT AGCTGTTTGC ACCTTCTGCG TCCGTGGTTG 966

TGTTTCCGTG CTACCTTTTT ATGTTTTGAT TTGGATCTTG TTTGAAAATA ATCTTACCAG 1026

CTTTGGGTAA ACTGTTT 1043

(2) INFORMATION FOR SEQ ID NO: 13:

(i) SEQUENCE CHARACTERISTICS:
        (A) LENGTH: 250 amino acid residues
        (B) TYPE: amino acid
        (D) TOPOLOGY: linear (xi) SEQUENCE DESCRIPTION: SEQ ID NO:13:

| | | | | | | | | | | | | | | |
|---|---|---|---|---|---|---|---|---|---|---|---|---|---|---|
|Met|Gly|Arg|Gly|Arg|Val|Glu|Leu|Lys|Arg|Ile|Glu|Asn|Lys|Ile|Asn|
| | | | |5| | | | |10| | | | |15| |

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
         35                  40                  45

Ser Lys Ser Arg Gly Leu Tyr Glu Phe Gly Ser Ala Gly Ile Thr Lys
 50                      55                  60

Thr Leu Glu Arg Tyr Gln His Cys Cys Tyr Asn Ala Gln Asp Ser Asn
 65              70                  75                  80

Asn Ala Leu Ser Glu Thr Gln Ser Trp Tyr His Glu Met Ser Lys Leu
                 85                  90                  95

Lys Ala Lys Phe Glu Ala Leu Gln Arg Thr Gln Arg His Leu Leu Gly
             100                 105                 110

Glu Asp Leu Gly Pro Leu Ser Val Lys Glu Leu Gln Gln Leu Glu Lys
         115                 120                 125

Gln Leu Glu Cys Ala Leu Ser Gln Ala Arg Gln Arg Lys Thr Gln Leu
 130                 135                 140

Met Met Glu Gln Val Glu Glu Leu Arg Arg Lys Glu Arg Gln Leu Gly
145                 150                 155                 160

Glu Ile Asn Arg Gln Leu Lys His Lys Leu Glu Val Glu Gly Ser Thr
                165                 170                 175

Ser Asn Tyr Arg Ala Met Gln Gln Ala Ser Trp Ala Gln Gly Ala Val
             180                 185                 190

Val Glu Asn Gly Ala Ala Tyr Val Gln Pro Pro His Ser Ala Ala
         195                 200                 205

Met Asp Ser Glu Pro Thr Leu Gln Ile Gly Tyr Pro His Gln Phe Val
    210                 215                 220

Pro Ala Glu Ala Asn Thr Ile Gln Arg Ser Thr Ala Pro Ala Gly Ala
225                 230                 235                 240

Glu Asn Asn Phe Met Leu Gly Trp Val Leu
                245                 250

(2) INFORMATION FOR SEQ ID NO: 14:

(i) SEQUENCE CHARACTERISTICS:
        (A) LENGTH: 1059 base pairs
        (B) TYPE: nucleic acid
        (C) STRANDEDNESS: double stranded
        (D) TOPOLOGY: linear (xi) SEQUENCE DESCRIPTION: SEQ ID NO:14:

```
TATCCCCTTC CTCCAGGTGG CTTGTTTCTT GCAGTGGTGG TGGTGGTGGT GGTGAGATCT      60

AGCTTGGTTG TTGGTGGCA GCTGGAGATC GATCGGG                                97

ATG GGG AGG GGG CGG GTG GAG CTG AAG AGG ATC GAG AAC AAG ATC AAC       145
Met Gly Arg Gly Arg Val Glu Leu Lys Arg Ile Glu Asn Lys Ile Asn
             5                   10                  15

CGG AAG GTG ACG TTC GCC AAG AGG AGG AAT GGC CTG CTC AAG AAG GCG       193
Arg Lys Val Thr Phe Ala Lys Arg Arg Asn Gly Leu Leu Lys Lys Ala
              20                  25                  30

TAC GAG CTC TCC GTC CTC TGC GAC GCC GAG GTC GCC CTC ATC ATC TTC       241
Tyr Glu Leu Ser Val Leu Cys Asp Ala Glu Val Ala Leu Ile Ile Phe
           35                  40                  45

TCC AAC CGC GGC AAG CTC TAC GAG TTC TGC AGC ACC CAG AGC ATG ACT       289
Ser Asn Arg Gly Lys Leu Tyr Glu Phe Cys Ser Thr Gln Ser Met Thr
         50                  55                  60
```

```
AAA ACG CTT GAG AAG TAT CAG AAA TGC AGT TAC GCA GGA CCC GAA ACA       337
Lys Thr Leu Glu Lys Tyr Gln Lys Cys Ser Tyr Ala Gly Pro Glu Thr
 65                  70                  75                  80

GCT GTC CAA AAT AGA GAA AGT GAG CAA TTG AAA GCT AGC CGC AAT GAA       385
Ala Val Gln Asn Arg Glu Ser Glu Gln Leu Lys Ala Ser Arg Asn Glu
                     85                  90                  95

TAC CTC AAA CTG AAG GCA AGG GTT GAA AAT TTA CAA CGG ACT CAA AGA       433
Tyr Leu Lys Leu Lys Ala Arg Val Glu Asn Leu Gln Arg Thr Gln Arg
                100                 105                 110

AAT TTG CTG GGT CCA GAT CTT GAT TCA TTA GGC ATA AAA GAG CTC GAG       481
Asn Leu Leu Gly Pro Asp Leu Asp Ser Leu Gly Ile Lys Glu Leu Glu
            115                 120                 125

AGC CTA GAG AAG CAG CTT GAT TCA TCC CTG AAG CAC GTC AGA ACT ACA       529
Ser Leu Glu Lys Gln Leu Asp Ser Ser Leu Lys His Val Arg Thr Thr
130                 135                 140

AGG ACA AAA CAT CTG GTC GAC CAA CTG ACG GAG CTT CAG AGA AAG GAA       577
Arg Thr Lys His Leu Val Asp Gln Leu Thr Glu Leu Gln Arg Lys Glu
145                 150                 155                 160

CAA ATG GTT TCT GAA GCA AAT AGA TGC CTT AGG AGA AAA CTG GAG GAA       625
Gln Met Val Ser Glu Ala Asn Arg Cys Leu Arg Arg Lys Leu Glu Glu
                165                 170                 175

AGC AAC CAT GTT CGC GGG CAG CAA GTG TGG GAG CAG GGC TGC AAC TTA       673
Ser Asn His Val Arg Gly Gln Gln Val Trp Glu Gln Gly Cys Asn Leu
                180                 185                 190

ATT GGC TAT GAA CGT CAG CCT GAA GTG CAG CAG CCT CTT CAC GGC GGC       721
Ile Gly Tyr Glu Arg Gln Pro Glu Val Gln Gln Pro Leu His Gly Gly
            195                 200                 205

AAT GGG TTC TTC CAT CCA CTT GAT GCT GCT GGT GAA CCC ACC CTT CAG       769
Asn Gly Phe Phe His Pro Leu Asp Ala Ala Gly Glu Pro Thr Leu Gln
            210                 215                 220

ATT GGG TAC CCT GCA GAG CAT CAT GAG GCG ATG AAC AGT GCG TGC ATG       817
Ile Gly Tyr Pro Ala Glu His His Glu Ala Met Asn Ser Ala Cys Met
225                 230                 235                 240

AAC ACC TAC ATG CCC CCA TGG CTA CCA TGA                               847
Asn Thr Tyr Met Pro Pro Trp Leu Pro
                245

TGATGACGGG ACAATGAATT ACGAAATAAC AAGGATATGT GGCATATATG TGGTGCCGCA     907

TACATGCATG TATCATGGCT AGCTACTTAA TTGGAGTGAT GGATTTGAAC TAGTTTCGTA     967

TGTAGCCTGT TTGTGTGTAA CTTGTGTGAG ATACTACCTT AAAAACTATC GGTGTCTGTT    1027

GAACATATTC TGCGATCAAC TTTAAGCGTA TT                                  1059

(2) INFORMATION FOR SEQ ID NO: 15:

(i) SEQUENCE CHARACTERISTICS:
        (A) LENGTH:  249 amino acid residues
        (B) TYPE:    amino acid
        (D) TOPOLOGY: linear (xi) SEQUENCE DESCRIPTION:  SEQ ID NO:15:

Met Gly Arg Gly Arg Val Glu Leu Lys Arg Ile Glu Asn Lys Ile Asn
                 5                  10                  15

Arg Lys Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Thr Gln Ser Met Thr
        50                  55                  60

Lys Thr Leu Glu Lys Tyr Gln Lys Cys Ser Tyr Ala Gly Pro Glu Thr
 65                  70                  75                  80
```

```
Ala Val Gln Asn Arg Glu Ser Glu Gln Leu Lys Ala Ser Arg Asn Glu
                85                  90                  95

Tyr Leu Lys Leu Lys Ala Arg Val Glu Asn Leu Gln Arg Thr Gln Arg
            100                 105                 110

Asn Leu Leu Gly Pro Asp Leu Asp Ser Leu Gly Ile Lys Glu Leu Glu
            115                 120                 125

Ser Leu Glu Lys Gln Leu Asp Ser Ser Leu Lys His Val Arg Thr Thr
    130                 135                 140

Arg Thr Lys His Leu Val Asp Gln Leu Thr Glu Leu Gln Arg Lys Glu
145                 150                 155                 160

Gln Met Val Ser Glu Ala Asn Arg Cys Leu Arg Arg Lys Leu Glu Glu
                165                 170                 175

Ser Asn His Val Arg Gly Gln Gln Val Trp Glu Gln Gly Cys Asn Leu
                180                 185                 190

Ile Gly Tyr Glu Arg Gln Pro Gln Val Gln Gln Pro Leu His Gly Gly
            195                 200                 205

Asn Gly Phe Phe His Pro Leu Asp Ala Ala Gly Glu Pro Thr Leu Gln
            210                 215                 220

Ile Gly Tyr Pro Ala Glu His His Glu Ala Met Asn Ser Ala Cys Met
225                 230                 235                 240

Asn Thr Tyr Met Pro Pro Trp Leu Pro
                245
```

(2) INFORMATION FOR SEQ ID NO: 16:

(i) SEQUENCE CHARACTERISTICS:
        (A) LENGTH: 1180 base pairs
        (B) TYPE: nucleic acid
        (C) STRANDEDNESS: double stranded
        (D) TOPOLOGY: linear (xi) SEQUENCE DESCRIPTION: SEQ ID NO:16:

```
TGCTTTCCCC TCTCTTCCGC TTCGCGAGAT TGGTTGATTC ATCTCGCGAT TGATCGAGCT      60

CGAGCGGCGG TGAGGTGAGG TGGAGGAGGA GGAGGAGGAG GAGATCGGG                 109

ATG GGG AGA GGG AGG GTG GAG CTG AAG AGG ATC GAG AAC AAG ATC AAC      157
Met Gly Arg Gly Arg Val Glu Leu Lys Arg Ile Glu Asn Lys Ile Asn
                 5                  10                  15

AGG CAG GTG ACG TTC GCG AAG CGG AGG AAT GGG CTG CTC AAG AAG GCG      205
Arg Gln Val Thr Phe Ala Lys Arg Arg Asn Gly Leu Leu Lys Lys Ala
             20                  25                  30

TAC GAG CTC TCC GTG CTC TGC GAC GCC GAG GTC GCC CTC ATC ATC TTC      253
Tyr Glu Leu Ser Val Leu Cys Asp Ala Glu Val Ala Leu Ile Ile Phe
         35                  40                  45

TCC AAC CGC GGC AAG CTC TAC GAG TTC TGC AGC GGC CAA AGC ATG ACC      301
Ser Asn Arg Gly Lys Leu Tyr Glu Phe Cys Ser Gly Gln Ser Met Thr
 50                  55                  60

AGA ACT TTG GAA AGA TAC CAA AAA TTC AGT TAT GGT GGG CCA GAT ACT      349
Arg Thr Leu Glu Arg Tyr Gln Lys Phe Ser Tyr Gly Gly Pro Asp Thr
 65                  70                  75                  80

GCA ATA CAG AAC AAG GAA AAT GAG TTA GTG CAA AGC AGC CGC AAT GAG      397
Ala Ile Gln Asn Lys Glu Asn Glu Leu Val Gln Ser Ser Arg Asn Glu
                 85                  90                  95

TAC CTC AAA CTG AAG GCA CGG GTG GAA AAT TTA CAG AGG ACC CAA AGG      445
Tyr Leu Lys Leu Lys Ala Arg Val Glu Asn Leu Gln Arg Thr Gln Arg
            100                 105                 110

AAT CTT CTT GGT GAA GAT CTT GGG ACA CTT GGC ATA AAA GAG CTA GAG      493
Asn Leu Leu Gly Glu Asp Leu Gly Thr Leu Gly Ile Lys Glu Leu Glu
            115                 120                 125
```

```
CAG CTT GAG AAA CAA CTT GAT TCA TCC TTG AGG CAC ATT AGA TCC ACA        541
Gln Leu Glu Lys Gln Leu Asp Ser Ser Leu Arg His Ile Arg Ser Thr
    130                 135                 140

AGG ACA CAG CAT ATG CTT GAT CAG CTC ACT GAT CTC CAG AGG AGG GAA        589
Arg Thr Gln His Met Leu Asp Gln Leu Thr Asp Leu Gln Arg Arg Glu
145                 150                 155                 160

CAA ATG TTG TGT GAA GCA AAT AAG TGC CTC AGA AGA AAA CTG GAG GAG        637
Gln Met Leu Cys Glu Ala Asn Lys Cys Leu Arg Arg Lys Leu Glu Glu
                165                 170                 175

AGC AAC CAG TTG CAT GGA CAA GTG TGG GAG CAC GGC GCC ACC CTA CTC        685
Ser Asn Gln Leu His Gly Gln Val Trp Glu His Gly Ala Thr Leu Leu
            180                 185                 190

GGC TAC GAG CGG CAG TCG CCT CAT GCC GTC CAG CAG GTG CCA CCG CAC        733
Gly Tyr Glu Arg Gln Ser Pro His Ala Val Gln Gln Val Pro Pro His
        195                 200                 205

GGT GGC AAC GGA TTC TTC CAT TCC CTG GAA GCT GCC GCC GAG CCC ACC        781
Gly Gly Asn Gly Phe Phe His Ser Leu Glu Ala Ala Ala Glu Pro Thr
    210                 215                 220

TTG CAG ATC GGG TTT ACT CCA GAG CAG ATG AAC AAC TCA TGC GTG ACT        829
Leu Gln Ile Gly Phe Thr Pro Glu Gln Met Asn Asn Ser Cys Val Thr
225                 230                 235                 240

GCC TTC ATG CCG ACA TGG CTA CCC TGA                                    856
Ala Phe Met Pro Thr Trp Leu Pro
                245

ACTCCTGAAG GCCGATGCGA CAACCAATAA AAACGGATGT GACGACACAG ATCAAGTCGC      916

ACCATTAGAT TGATCTTCTC CTACAAGAGT GAGACTAGTA ATTCCGCGTT TGTGTGCTAG      976

CGTGTTGAAA CTTTTCTGAT GTGATGCACG CACTTTTAAT TATTATTAAG CGTTCAAGGA     1036

CTAGTATGTG GTATAAAAGC CCGTACGTGA CAGCCTATGG TTATATGCTG CGCAAAAACT     1096

ACGTATGGTA CAGTGCAGTG CCTGTACATT TCATAATTTG CGGGTAAAGT TTATTGACTA     1156

TATATCCAGT GTGTCAAATA TAAT                                            1180

(2) INFORMATION FOR SEQ ID NO: 17:

(i) SEQUENCE CHARACTERISTICS:
        (A) LENGTH:  248 amino acid residues
        (B) TYPE:  amino acid
        (D) TOPOLOGY:  linear (xi) SEQUENCE DESCRIPTION:  SEQ ID NO:17:

Met Gly Arg Gly Arg Val Glu Leu Lys Arg Ile Glu Asn Lys Ile Asn
                5                  10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Gly Gln Ser Met Thr
    50                  55                  60

Arg Thr Leu Glu Arg Tyr Gln Lys Phe Ser Tyr Gly Gly Pro Asp Thr
65                  70                  75                  80

Ala Ile Gln Asn Lys Glu Asn Glu Leu Val Gln Ser Ser Arg Asn Glu
                85                  90                  95

Tyr Leu Lys Leu Lys Ala Arg Val Glu Asn Leu Gln Arg Thr Gln Arg
            100                 105                 110

Asn Leu Leu Gly Glu Asp Leu Gly Thr Leu Gly Ile Lys Glu Leu Glu
        115                 120                 125
```

-continued

Gln Leu Glu Lys Gln Leu Asp Ser Ser Leu Arg His Ile Arg Ser Thr
130                 135                 140

Arg Thr Gln His Met Leu Asp Gln Leu Thr Asp Leu Gln Arg Glu
145                 150                 155                 160

Gln Met Leu Cys Glu Ala Asn Lys Cys Leu Arg Arg Lys Leu Glu Glu
                165                 170                 175

Ser Asn Gln Leu His Gly Gln Val Trp Glu His Gly Ala Thr Leu Leu
            180                 185                 190

Gly Tyr Glu Arg Gln Ser Pro His Ala Val Gln Gln Val Pro Pro His
        195                 200                 205

Gly Gly Asn Gly Phe Phe His Ser Leu Glu Ala Ala Ala Glu Pro Thr
210                 215                 220

Leu Gln Ile Gly Phe Thr Pro Glu Gln Met Asn Asn Ser Cys Val Thr
225                 230                 235                 240

Ala Phe Met Pro Thr Trp Leu Pro
                245

(2) INFORMATION FOR SEQ ID NO: 18:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:18:

Gly Arg Gly Arg Val Glu Leu Lys Arg Ile Glu Asn Lys Ile Asn Arg
                5                   10                  15

Gln Val Thr Phe Ser Lys Arg Arg Asn Gly Leu Leu Lys Lys Ala Tyr
            20                  25                  30

Glu Leu Ser Val Leu Cys Asp Ala Glu Val Ala Leu Ile Ile Phe Ser
        35                  40                  45

Ser Arg Gly Lys Leu Tyr Glu Phe
50                  55

(2) INFORMATION FOR SEQ ID NO: 19:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:19:

Gly Arg Gly Arg Val Glu Leu Lys Arg Ile Glu Asn Lys Ile Asn Arg
                5                   10                  15

Gln Val Thr Phe Ser Lys Arg Arg Asn Gly Leu Leu Lys Lys Ala Tyr
            20                  25                  30

Glu Leu Ser Val Leu Cys Asp Ala Glu Val Ala Leu Ile Ile Phe Ser
        35                  40                  45

Gly Arg Gly Lys Leu Tyr Glu Phe
50                  55

(2) INFORMATION FOR SEQ ID NO: 20:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:20:

Gly Arg Gly Arg Val Glu Met Lys Arg Ile Glu Asn Lys Ile Asn Arg
                5                   10                  15

Gln Val Thr Phe Ser Lys Arg Arg Asn Gly Leu Leu Lys Lys Ala Tyr
            20                  25                  30

Glu Leu Ser Val Leu Cys Asp Ala Glu Val Ala Leu Ile Ile Phe Ser
            35                  40                  45

Ser Arg Gly Lys Leu Tyr Glu Phe
        50                  55

(2) INFORMATION FOR SEQ ID NO: 21:

(i) SEQUENCE CHARACTERISTICS:
        (A) LENGTH:  56 amino acid residues
        (B) TYPE:  amino acid
        (D) TOPOLOGY:  linear (xi) SEQUENCE DESCRIPTION:  SEQ ID NO:21:

Gly Arg Gly Arg Val Glu Leu Lys Arg Ile Glu Asn Lys Ile Asn Arg
                5                   10                  15

Gln Val Thr Phe Ala Lys Arg Arg Asn Gly Leu Leu Lys Lys Ala Tyr
            20                  25                  30

Glu Leu Ser Val Leu Cys Asp Ala Glu Val Ala Leu Ile Ile Phe Ser
            35                  40                  45

Asn Arg Gly Lys Leu Tyr Glu Phe
        50                  55

(2) INFORMATION FOR SEQ ID NO: 22:

(i) SEQUENCE CHARACTERISTICS:
        (A) LENGTH:  56 amino acid residues
        (B) TYPE:  amino acid
        (D) TOPOLOGY:  linear (xi) SEQUENCE DESCRIPTION:  SEQ ID NO:22:

Gly Arg Gly Arg Val Glu Leu Lys Arg Ile Glu Gly Lys Ile Asn Arg
                5                   10                  15

Gln Val Thr Phe Ala Lys Arg Arg Asn Gly Leu Leu Lys Lys Ala Tyr
            20                  25                  30

Glu Leu Ser Val Leu Cys Asp Ala Glu Val Ala Leu Ile Ile Phe Ser
            35                  40                  45

Asn Arg Gly Lys Leu Tyr Glu Phe
        50                  55

(2) INFORMATION FOR SEQ ID NO: 23:

(i) SEQUENCE CHARACTERISTICS:
        (A) LENGTH:  56 amino acid residues
        (B) TYPE:  amino acid
        (D) TOPOLOGY:  linear (xi) SEQUENCE DESCRIPTION:  SEQ ID NO:23:

Gly Arg Gly Arg Val Glu Leu Lys Met Ile Glu Asn Lys Ile Asn Arg
                5                   10                  15

Gln Val Thr Phe Ala Lys Arg Arg Lys Arg Leu Leu Lys Lys Ala Tyr
            20                  25                  30

Glu Leu Ser Val Leu Cys Asp Ala Glu Val Ala Leu Ile Ile Phe Ser
            35                  40                  45

Asn Arg Gly Lys Leu Tyr Glu Phe
        50                  55

(2) INFORMATION FOR SEQ ID NO: 24:

(i) SEQUENCE CHARACTERISTICS:
        (A) LENGTH:  56 amino acid residues (B) TYPE: amino acid
(D) TOPOLOGY: linear (xi) SEQUENCE DESCRIPTION: SEQ ID NO:24:

Gly Arg Gly Arg Val Glu Leu Lys Arg Ile Glu Asn Lys Ile Asn Arg
                5                   10                  15
Gln Val Thr Phe Ala Lys Arg Arg Asn Gly Leu Leu Lys Lys Ala Tyr
            20                  25                  30
Glu Leu Ser Val Leu Cys Asp Ala Glu Val Ala Leu Ile Ile Phe Ser
        35                  40                  45
Asn Arg Gly Lys Leu Tyr Glu Phe
50                  55

(2) INFORMATION FOR SEQ ID NO: 25:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:25:

Gly Arg Gly Arg Val Glu Leu Lys Arg Ile Glu Asn Lys Ile Asn Arg
                5                   10                  15
Gln Val Thr Phe Ala Lys Arg Arg Asn Gly Leu Leu Lys Lys Ala Tyr
            20                  25                  30
Glu Leu Ser Val Leu Cys Asp Ala Glu Val Ser Leu Ile Val Phe Ser
        35                  40                  45
Asn Arg Gly Lys Leu Tyr Glu Phe
50                  55

(2) INFORMATION FOR SEQ ID NO: 26:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:26:

Gly Arg Gly Arg Val Gln Leu Lys Arg Ile Glu Asn Lys Ile Asn Arg
                5                   10                  15
Gln Val Thr Phe Ser Lys Arg Arg Ala Gly Leu Leu Lys Lys Ala His
            20                  25                  30
Glu Ile Ser Val Leu Cys Asp Ala Glu Val Ala Leu Val Val Phe Ser
        35                  40                  45
His Lys Gly Lys Leu Phe Glu Tyr
50                  55

(2) INFORMATION FOR SEQ ID NO: 27:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:27:

Gly Arg Gly Lys Ile Glu Ile Lys Arg Ile Glu Asn Thr Thr Asn Arg
                5                   10                  15
Gln Val Thr Phe Cys Lys Arg Arg Asn Gly Leu Leu Lys Lys Ala Tyr
            20                  25                  30
Glu Leu Ser Val Leu Cys Asp Ala Glu Val Ala Leu Ile Val Phe Ser
        35                  40                  45

```
Ser Arg Gly Arg Leu Tyr Glu Tyr
 50                  55
```

(2) INFORMATION FOR SEQ ID NO: 28:

(i) SEQUENCE CHARACTERISTICS:
        (A) LENGTH:  56 amino acid residues
        (B) TYPE:  amino acid
        (D) TOPOLOGY:  linear (xi) SEQUENCE DESCRIPTION:  SEQ ID NO:28:

```
Ala Arg Gly Lys Ile Gln Ile Lys Arg Ile Glu Asn Gln Thr Asn Arg
             5                  10                  15
Gln Val Thr Tyr Ser Lys Arg Arg Asn Gly Leu Phe Lys Lys Ala His
             20                  25                  30
Glu Leu Thr Val Leu Cys Asp Ala Arg Val Ser Ile Ile Met Phe Ser
             35                  40                  45
Ser Ser Asn Lys Leu His Glu Tyr
 50                  55
```

(2) INFORMATION FOR SEQ ID NO: 29:

(i) SEQUENCE CHARACTERISTICS:
        (A) LENGTH:  56 amino acid residues
        (B) TYPE:  amino acid
        (D) TOPOLOGY:  linear (xi) SEQUENCE DESCRIPTION:  SEQ ID NO:29:

```
Gly Arg Gly Lys Ile Glu Ile Lys Arg Ile Glu Asn Ala Asn Asn Arg
             5                  10                  15
Val Val Thr Phe Ser Lys Arg Arg Asn Gly Leu Val Lys Lys Ala Lys
             20                  25                  30
Glu Ile Thr Val Leu Cys Asp Ala Lys Val Ala Leu Ile Ile Phe Ala
             35                  40                  45
Ser Asn Gly Lys Met Ile Asp Tyr
 50                  55
```

(2) INFORMATION FOR SEQ ID NO: 30:

(i) SEQUENCE CHARACTERISTICS:
        (A) LENGTH:  65 amino acid residues
        (B) TYPE:  amino acid
        (D) TOPOLOGY:  linear (xi) SEQUENCE DESCRIPTION:  SEQ ID NO:30:

```
Gln Glu Met Ser Lys Leu Arg Ala Lys Phe Glu Ala Leu Gln Arg Thr
             5                  10                  15
Gln Arg His Leu Leu Gly Glu Glu Leu Gly Pro Leu Ser Val Lys Glu
             20                  25                  30
Leu Gln Gln Leu Glu Lys Gln Leu Glu Cys Ala Leu Ser Gln Ala Arg
             35                  40                  45
Gln Arg Lys Thr Gln Leu Met Met Glu Gln Val Glu Glu Leu Arg Arg
 50                  55                  60
Lys
 65
```

(2) INFORMATION FOR SEQ ID NO: 31:

(i) SEQUENCE CHARACTERISTICS:
        (A) LENGTH:  65 amino acid residues
        (B) TYPE:  amino acid
        (D) TOPOLOGY:  linear (xi) SEQUENCE DESCRIPTION:  SEQ ID NO:31:

Gln Glu Met Ser Lys Leu Arg Ala Lys Phe Glu Ala Leu Gln Arg Thr
                5                  10                 15

Gln Arg His Leu Leu Gly Glu Asp Leu Gly Pro Leu Ser Val Lys Glu
            20                  25                 30

Leu Gln Gln Leu Glu Lys Gln Leu Glu Cys Ala Leu Ser Gln Ala Arg
            35                  40                 45

Gln Arg Lys Thr Gln Val Met Met Glu Gln Val Glu Glu Leu Arg Arg
    50                  55                  60

Thr
65

(2) INFORMATION FOR SEQ ID NO: 32:

(i) SEQUENCE CHARACTERISTICS:
        (A) LENGTH: 65 amino acid residues
        (B) TYPE: amino acid
        (D) TOPOLOGY: linear (xi) SEQUENCE DESCRIPTION: SEQ ID NO:32:

Gln Glu Val Thr Lys Leu Lys Ser Lys Tyr Glu Ser Leu Val Arg Thr
                5                  10                 15

Asn Arg Asn Leu Leu Gly Glu Asp Leu Gly Glu Met Gly Val Lys Glu
            20                  25                 30

Leu Gln Ala Leu Glu Arg Gln Leu Glu Ala Ala Leu Thr Ala Thr Arg
            35                  40                 45

Gln Arg Lys Thr Gln Val Met Met Glu Glu Met Glu Asp Leu Arg Lys
    50                  55                  60

Lys
65

(2) INFORMATION FOR SEQ ID NO: 33:

(i) SEQUENCE CHARACTERISTICS:
        (A) LENGTH: 65 amino acid residues
        (B) TYPE: amino acid
        (D) TOPOLOGY: linear (xi) SEQUENCE DESCRIPTION: SEQ ID NO:33:

Gln Glu Tyr Leu Lys Leu Lys Ala Arg Tyr Glu Ala Leu Gln Arg Ser
                5                  10                 15

Gln Arg Asn Leu Leu Gly Glu Asp Leu Gly Pro Leu Asn Ser Lys Glu
            20                  25                 30

Leu Glu Ser Leu Glu Arg Gln Leu Asp Met Ser Leu Lys Gln Ile Arg
            35                  40                 45

Ser Thr Arg Thr Gln Leu Met Leu Asp Gln Leu Gln Asp Leu Gln Arg
    50                  55                  60

Lys
65

(2) INFORMATION FOR SEQ ID NO: 34:

(i) SEQUENCE CHARACTERISTICS:
        (A) LENGTH: 65 amino acid residues
        (B) TYPE: amino acid
        (D) TOPOLOGY: linear (xi) SEQUENCE DESCRIPTION: SEQ ID NO:34:

Gln Glu Tyr Leu Lys Leu Lys Gly Arg Tyr Glu Ala Leu Gln Arg Ser
                5                  10                 15

Gln Arg Asn Leu Leu Gly Glu Asp Leu Gly Pro Leu Asn Ser Lys Glu
            20                  25                  30

Leu Glu Ser Leu Glu Arg Gln Leu Asp Met Ser Leu Lys Gln Ile Arg
            35                  40                  45

Ser Thr Arg Thr Gln Leu Met Leu Asp Gln Leu Thr Asp Tyr Gln Arg
            50                  55                  60

Lys
65

(2) INFORMATION FOR SEQ ID NO: 35:

(i) SEQUENCE CHARACTERISTICS:
       (A) LENGTH: 65 amino acid residues
       (B) TYPE: amino acid
       (D) TOPOLOGY: linear (xi) SEQUENCE DESCRIPTION: SEQ ID NO:35:

Gln Glu Tyr Leu Lys Leu Lys Asn Arg Val Glu Ala Leu Gln Arg Ser
              5                  10                  15

Gln Arg Asn Leu Leu Gly Glu Asp Leu Gly Pro Leu Gly Ser Lys Glu
            20                  25                  30

Leu Glu Gln Leu Glu Arg Gln Leu Asp Ser Ser Leu Arg Gln Ile Arg
            35                  40                  45

Ser Thr Arg Thr Gln Phe Met Leu Asp Gln Leu Ala Asp Leu Gln Arg
            50                  55                  60

Arg
65

(2) INFORMATION FOR SEQ ID NO: 36:

(i) SEQUENCE CHARACTERISTICS:
       (A) LENGTH: 65 amino acid residues
       (B) TYPE: amino acid
       (D) TOPOLOGY: linear (xi) SEQUENCE DESCRIPTION: SEQ ID NO:36:

Arg Glu Tyr Leu Lys Leu Lys Gly Arg Tyr Glu Asn Leu Gln Arg Gln
              5                  10                  15

Gln Arg Asn Leu Leu Gly Glu Asp Leu Gly Pro Leu Asn Ser Lys Glu
            20                  25                  30

Leu Glu Gln Leu Glu Arg Gln Leu Asp Gly Ser Leu Lys Gln Val Arg
            35                  40                  45

Ser Ile Lys Thr Gln Tyr Met Leu Asp Gln Leu Ser Asp Leu Gln Asn
            50                  55                  60

Lys
65

(2) INFORMATION FOR SEQ ID NO: 37:

(i) SEQUENCE CHARACTERISTICS:
       (A) LENGTH: 65 amino acid residues
       (B) TYPE: amino acid
       (D) TOPOLOGY: linear (xi) SEQUENCE DESCRIPTION: SEQ ID NO:37:

Arg Glu Tyr Leu Lys Leu Lys Gly Arg Tyr Glu Asn Leu Gln Arg Gln
              5                  10                  15

Gln Arg Asn Leu Leu Gly Glu Asp Leu Gly Pro Leu Asn Ser Lys Glu
            20                  25                  30

Leu Glu Gln Leu Glu Arg Gln Leu Asp Gly Ser Leu Lys Gln Val Arg
            35                  40                  45

```
Cys Ile Lys Thr Gln Tyr Met Leu Asp Gln Leu Ser Asp Leu Gln Gly
     50                  55                  60

Lys
65

(2) INFORMATION FOR SEQ ID NO: 38:

(i) SEQUENCE CHARACTERISTICS:
        (A) LENGTH:   65 amino acid residues
        (B) TYPE:  amino acid
        (D) TOPOLOGY:  linear (xi) SEQUENCE DESCRIPTION:  SEQ ID NO:38:

Met Glu Tyr Asn Arg Leu Lys Ala Lys Ile Glu Leu Leu Glu Arg Asn
                 5                  10                  15

Gln Arg His Tyr Leu Gly Glu Asp Leu Gln Ala Met Ser Pro Lys Glu
             20                  25                  30

Leu Gln Asn Leu Glu Gln Gln Leu Asp Thr Ala Leu Lys His Ile Arg
             35                  40                  45

Thr Arg Lys Asn Gln Leu Met Tyr Glu Ser Ile Asn Glu Leu Gln Lys
     50                  55                  60

Lys
65

(2) INFORMATION FOR SEQ ID NO: 39:

(i) SEQUENCE CHARACTERISTICS:
        (A) LENGTH:   65 amino acid residues
        (B) TYPE:  amino acid
        (D) TOPOLOGY:  linear (xi) SEQUENCE DESCRIPTION:  SEQ ID NO:39:

Gln Glu Ser Ala Lys Leu Arg Gln Gln Ile Ile Ser Ile Gln Asn Ser
                 5                  10                  15

Asn Arg Gln Leu Met Gly Glu Thr Ile Gly Ser Met Ser Pro Lys Glu
             20                  25                  30

Leu Arg Asn Leu Glu Gly Arg Leu Glu Arg Ser Ile Thr Arg Ile Arg
             35                  40                  45

Ser Lys Lys Asn Glu Leu Leu Phe Ser Glu Ile Asp Tyr Met Gln Lys
     50                  55                  60

Arg
65

(2) INFORMATION FOR SEQ ID NO: 40:

(i) SEQUENCE CHARACTERISTICS:
        (A) LENGTH:   66 amino acid residues
        (B) TYPE:  amino acid
        (D) TOPOLOGY:  linear (xi) SEQUENCE DESCRIPTION:  SEQ ID NO:40:

Gln Glu Thr Lys Arg Lys Leu Leu Glu Thr Asn Arg Asn Leu Arg Thr
                 5                  10                  15

Gln Ile Lys Gln Arg Leu Gly Glu Cys Leu Asp Glu Leu Asp Ile Gln
             20                  25                  30

Glu Leu Arg Arg Leu Glu Asp Glu Met Glu Asn Thr Phe Lys Leu Val
             35                  40                  45

Arg Glu Arg Lys Phe Lys Ser Leu Gly Asn Gln Ile Glu Thr Thr Lys
     50                  55                  60
```

```
Lys Lys
65

(2) INFORMATION FOR SEQ ID NO: 41:

(i) SEQUENCE CHARACTERISTICS:
        (A) LENGTH:  61 amino acid residues
        (B) TYPE:  amino acid
        (D) TOPOLOGY:  linear (xi) SEQUENCE DESCRIPTION:  SEQ ID NO:41:

Asn Glu Ile Asp Arg Ile Lys Lys Glu Asn Asp Ser Leu Gln Leu Glu
                 5                  10                  15

Leu Arg His Leu Lys Gly Glu Asp Ile Gln Ser Leu Asn Leu Lys Asn
             20                  25                  30

Leu Met Ala Val Glu His Ala Ile Glu His Gly Leu Asp Lys Val Arg
             35                  40                  45

Asp His Gln Met Glu Ile Leu Ile Ser Lys Arg Arg Asn
         50                  55                  60

(2) INFORMATION FOR SEQ ID NO: 42:

(i) SEQUENCE CHARACTERISTICS:
        (A) LENGTH:  39 amino acid residues
        (B) TYPE:  amino acid
        (D) TOPOLOGY:  linear (xi) SEQUENCE DESCRIPTION:  SEQ ID NO:42:

Glu Pro Thr Leu Gln Ile Gly Tyr Pro His His Gln Phe Pro Pro Pro
                 5                  10                  15

Glu Ala Val Asn Asn Ile Pro Arg Ser Ala Ala Thr Gly Glu Asn Asn
             20                  25                  30

Phe Met Leu Gly Trp Val Leu
         35

(2) INFORMATION FOR SEQ ID NO: 43:

(i) SEQUENCE CHARACTERISTICS:
        (A) LENGTH:  40 amino acid residues
        (B) TYPE:  amino acid
        (D) TOPOLOGY:  linear (xi) SEQUENCE DESCRIPTION:  SEQ ID NO:43:

Glu Pro Thr Leu Gln Ile Gly Tyr Pro Pro His His Gln Phe Leu Pro
                 5                  10                  15

Ser Glu Ala Ala Asn Asn Ile Pro Arg Ser Pro Pro Gly Gly Glu Asn
             20                  25                  30

Asn Phe Met Leu Gly Trp Val Leu
         35                  40

(2) INFORMATION FOR SEQ ID NO: 44:

(i) SEQUENCE CHARACTERISTICS:
        (A) LENGTH:  38 amino acid residues
        (B) TYPE:  amino acid
        (D) TOPOLOGY:  linear (xi) SEQUENCE DESCRIPTION:  SEQ ID NO:44:

Glu Pro Phe Leu Gln Ile Gly Phe Gly Gln His Tyr Tyr Val Gly Gly
                 5                  10                  15

Glu Gly Ser Ser Val Ser Lys Ser Asn Val Ala Gly Glu Thr Asn Phe
             20                  25                  30
```

```
Val Gln Gly Trp Val Leu
        35

(2) INFORMATION FOR SEQ ID NO: 45:

(i) SEQUENCE CHARACTERISTICS:
        (A) LENGTH:  31 amino acid residues
        (B) TYPE:  amino acid
        (D) TOPOLOGY:  linear (xi) SEQUENCE DESCRIPTION:  SEQ ID NO:45:

Glu Pro Thr Leu Gln Ile Gly Tyr Gln Asn Asp Pro Ile Thr Val Gly
                 5                  10                  15

Gly Ala Gly Pro Ser Val Asn Asn Tyr Met Ala Gly Trp Leu Pro
             20                  25                  30

(2) INFORMATION FOR SEQ ID NO: 46:

(i) SEQUENCE CHARACTERISTICS:
        (A) LENGTH:  31 amino acid residues
        (B) TYPE:  amino acid
        (D) TOPOLOGY:  linear (xi) SEQUENCE DESCRIPTION:  SEQ ID NO:46:

Glu Pro Thr Leu Gln Ile Gly Tyr Gln Asn Asp Pro Ile Thr Val Gly
                 5                  10                  15

Gly Ala Gly Pro Ser Val Asn Asn Tyr Met Ala Gly Trp Leu Pro
             20                  25                  30

(2) INFORMATION FOR SEQ ID NO: 47:

(i) SEQUENCE CHARACTERISTICS:
        (A) LENGTH:  32 amino acid residues
        (B) TYPE:  amino acid
        (D) TOPOLOGY:  linear (xi) SEQUENCE DESCRIPTION:  SEQ ID NO:47:

Glu Pro Thr Leu Gln Ile Gly Tyr His Ser Asp Ile Thr Met Ala Thr
                 5                  10                  15

Ala Thr Ala Ser Thr Val Asn Asn Tyr Met Pro Pro Gly Trp Leu Gly
             20                  25                  30

(2) INFORMATION FOR SEQ ID NO: 48:

(i) SEQUENCE CHARACTERISTICS:
        (A) LENGTH:  37 amino acid residues
        (B) TYPE:  amino acid
        (D) TOPOLOGY:  linear (xi) SEQUENCE DESCRIPTION:  SEQ ID NO:48:

Asn Pro Thr Leu Gln Met Gly Tyr Asp Asn Pro Val Cys Ser Glu Gln
                 5                  10                  15

Ile Thr Ala Thr Thr Gln Ala Gln Ala Gln Pro Gly Asn Gly Tyr Ile
             20                  25                  30

Pro Gly Trp Met Leu
        35

(2) INFORMATION FOR SEQ ID NO: 49:

(i) SEQUENCE CHARACTERISTICS:
        (A) LENGTH:  37 amino acid residues
        (B) TYPE:  amino acid
        (D) TOPOLOGY:  linear (xi) SEQUENCE DESCRIPTION:  SEQ ID NO:49:
```

```
Asp Pro Thr Leu Gln Ile Gly Tyr Ser His Pro Val Cys Ser Glu Gln
                  5                  10                  15

Met Ala Val Thr Val Gln Gly Gln Ser Gln Gln Gly Asn Gly Tyr Ile
             20                  25                  30

Pro Gly Trp Met Leu
         35
```

(2) INFORMATION FOR SEQ ID NO: 50:

(i) SEQUENCE CHARACTERISTICS:
        (A) LENGTH: 39 amino acid residues
        (B) TYPE: amino acid
        (D) TOPOLOGY: linear (xi) SEQUENCE DESCRIPTION: SEQ ID NO:50:

```
Ser Pro Phe Leu Asn Met Gly Gly Leu Tyr Gln Glu Asp Asp Pro Met
                  5                  10                  15

Ala Met Arg Asn Asp Leu Glu Leu Thr Leu Glu Pro Val Tyr Asn Cys
             20                  25                  30

Asn Leu Gly Cys Phe Ala Ala
         35
```

(2) INFORMATION FOR SEQ ID NO: 51:

(i) SEQUENCE CHARACTERISTICS:
        (A) LENGTH: 25 amino acid residues
        (B) TYPE: amino acid
        (D) TOPOLOGY: linear (xi) SEQUENCE DESCRIPTION: SEQ ID NO:51:

```
Val Ala Ala Leu Gln Pro Asn Asn His His Tyr Ser Ser Ala Gly Arg
                  5                  10                  15

Gln Asp Gln Thr Ala Leu Gln Leu Val
             20                  25
```

(2) INFORMATION FOR SEQ ID NO: 52:

(i) SEQUENCE CHARACTERISTICS:
        (A) LENGTH: 29 amino acid residues
        (B) TYPE: amino acid
        (D) TOPOLOGY: linear (xi) SEQUENCE DESCRIPTION: SEQ ID NO:52:

```
Phe His Gln Asn His His His Tyr Tyr Pro Asn His Gly Leu His Ala
                  5                  10                  15

Pro Ser Ala Ser Asp Ile Ile Thr Phe His Leu Leu Glu
             20                  25
```

(2) INFORMATION FOR SEQ ID NO: 53:

(i) SEQUENCE CHARACTERISTICS:
        (A) LENGTH: 18 amino acid residues
        (B) TYPE: amino acid
        (D) TOPOLOGY: linear (xi) SEQUENCE DESCRIPTION: SEQ ID NO:53:

```
Val Ala Ala Leu Gln Pro Asn Leu Gln Glu Lys Ile Met Ser Leu Val
                  5                  10                  15

Ile Asp
```

(2) INFORMATION FOR SEQ ID NO: 54:

(i) SEQUENCE CHARACTERISTICS:
        (A) LENGTH: 1027 base pairs (B) TYPE: nucleic acid
    (C) STRANDEDNESS: double stranded
    (D) TOPOLOGY: linear (xi) SEQUENCE DESCRIPTION: SEQ ID NO:54:

| | |
|---|---:|
| AAGACTGCAA GGGAGAGGGA GAGAGAGGGA AGCTTGCAGG CTGCAGCTAA CTAGCTAGGC | 60 |
| AAGGAGAGAG AGGAGATAGA TCAAGAAGAG ATTTTGAGAC CGAGAGAGAG CTAGAGAGAG | 120 |
| ATCG | 124 |

```
ATG GGG CGA GGG AAA GTA GAG CTG AAG CGG ATC GAG AAC AAG ATA AGC      172
Met Gly Arg Gly Lys Val Glu Leu Lys Arg Ile Glu Asn Lys Ile Ser
            5                  10                  15

CGG CAG GTG ACG TTC GCG AAG AGG AGG AAC GGG CTG CTG AAG AAG GCG      220
Arg Gln Val Thr Phe Ala Lys Arg Arg Asn Gly Leu Leu Lys Lys Ala
        20                  25                  30

TAC GAG CTG TCC GTG CTC TGC GAC GCC GAG GTC GCC CTC ATC ATC TTC      268
Tyr Glu Leu Ser Val Leu Cys Asp Ala Glu Val Ala Leu Ile Ile Phe
    35                  40                  45

TCC ACC CGC GGC CGC CTC TTC GAG TTC TCC ACC TCC TCC TGT ATG TAC      316
Ser Thr Arg Gly Arg Leu Phe Glu Phe Ser Thr Ser Ser Cys Met Tyr
50                  55                  60

AAG ACA CTG GAG CGA TAC CGC AGT TGC AAC TAC AAC CTT AAC TCA TGT      364
Lys Thr Leu Glu Arg Tyr Arg Ser Cys Asn Tyr Asn Leu Asn Ser Cys
65                  70                  75                  80

GAA GCA TCT GCT GCA CTG GAA ACT GAA CTA AGC AAT TAC CAA GAG TAC      412
Glu Ala Ser Ala Ala Leu Glu Thr Glu Leu Ser Asn Tyr Gln Glu Tyr
                85                  90                  95

TTA AAG TTA AAG ACA AGA GTT GAG TTC CTA CAA ACA ACT CAG AGA AAT      460
Leu Lys Leu Lys Thr Arg Val Glu Phe Leu Gln Thr Thr Gln Arg Asn
            100                 105                 110

CTT CTT GGC GAG GAC TTG GTT CCA CTT AGC TTG AAG GAG CTC GAG CAA      508
Leu Leu Gly Glu Asp Leu Val Pro Leu Ser Leu Lys Glu Leu Glu Gln
        115                 120                 125

CTT GAG AAC CAG ATC GAG ATA TCC CTC ATG AAT ATC AGG TCA TCA AAG      556
Leu Glu Asn Gln Ile Glu Ile Ser Leu Met Asn Ile Arg Ser Ser Lys
    130                 135                 140

AAT CAA CAG TTG CTT GAT CAA GTA TTT GAG CTC AAA CGT AAG GAA CAA      604
Asn Gln Gln Leu Leu Asp Gln Val Phe Glu Leu Lys Arg Lys Glu Gln
145                 150                 155                 160

CAA CTT CAA GAT GCT AAT AAA GAC TTA AAA AGG AAG ATA CAA GAA ACT      652
Gln Leu Gln Asp Ala Asn Lys Asp Leu Lys Arg Lys Ile Gln Glu Thr
                165                 170                 175

AGT GGA GAA AAT ATG CTT CAT ATA TCT TGC CAA GAT GTA GGG CCC AGT      700
Ser Gly Glu Asn Met Leu His Ile Ser Cys Gln Asp Val Gly Pro Ser
            180                 185                 190

GGC CAT GCT AGT GAA GCT AAC CAA GAG TTT CTC CAT CAT GCA ATT TGT      748
Gly His Ala Ser Glu Ala Asn Gln Glu Phe Leu His His Ala Ile Cys
        195                 200                 205

GAC CCT TCC CTG CAT ATA GGG TAT CAA GCT TAC ATG GAT CAC CTC AAC      796
Asp Pro Ser Leu His Ile Gly Tyr Gln Ala Tyr Met Asp His Leu Asn
    210                 215                 220

CAA TGA                                                              802
Gln
225
```

| | |
|---|---:|
| ATGAATTGCT TATCACATTA ATGGACATCT CCTATGTTGG ATGTGGTGTT TGACGTAATG | 862 |
| CTCTCTTTTA CATGCGGGTT TTACCTTAAG TGTGTGTGCT AAATTTAGTG CGTTTGTTTA | 922 |
| TGCTCTTTTG AACTGAACAA AGGAATGATC CCGGTTTGAT TGATGAATGC TGCAAGAACA | 982 |
| TAATCTATAT GTTAGTCTGA ATTCAGTATG TAATGAAGAT GTTTT | 1027 |

(2) INFORMATION FOR SEQ ID NO: 55:

(i) SEQUENCE CHARACTERISTICS:
        (A) LENGTH: 225 amino acid residues
        (B) TYPE: amino acid
        (D) TOPOLOGY: linear (xi) SEQUENCE DESCRIPTION: SEQ ID NO:55:

```
Met Gly Arg Gly Lys Val Glu Leu Lys Arg Ile Glu Asn Lys Ile Ser
              5                  10                  15

Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ala Leu Ile Ile Phe
             35                  40                  45

Ser Thr Arg Gly Arg Leu Phe Glu Phe Ser Thr Ser Ser Cys Met Tyr
 50                  55                  60

Lys Thr Leu Glu Arg Tyr Arg Ser Cys Asn Tyr Asn Leu Asn Ser Cys
 65                  70                  75                  80

Glu Ala Ser Ala Ala Leu Glu Thr Glu Leu Ser Asn Tyr Gln Glu Tyr
                 85                  90                  95

Leu Lys Leu Lys Thr Arg Val Glu Phe Leu Gln Thr Thr Gln Arg Asn
                100                 105                 110

Leu Leu Gly Glu Asp Leu Val Pro Leu Ser Leu Lys Glu Leu Glu Gln
            115                 120                 125

Leu Glu Asn Gln Ile Glu Ile Ser Leu Met Asn Ile Arg Ser Ser Lys
            130                 135                 140

Asn Gln Gln Leu Leu Asp Gln Val Phe Glu Leu Lys Arg Lys Glu Gln
145                 150                 155                 160

Gln Leu Gln Asp Ala Asn Lys Asp Leu Lys Arg Lys Ile Gln Glu Thr
                165                 170                 175

Ser Gly Glu Asn Met Leu His Ile Ser Cys Gln Asp Val Gly Pro Ser
                180                 185                 190

Gly His Ala Ser Glu Ala Asn Gln Glu Phe Leu His His Ala Ile Cys
            195                 200                 205

Asp Pro Ser Leu His Ile Gly Tyr Gln Ala Tyr Met Asp His Leu Asn
            210                 215                 220
Gln
225
```

(2) INFORMATION FOR SEQ ID NO: 56:

(i) SEQUENCE CHARACTERISTICS:
        (A) LENGTH: 56 amino acid residues
        (B) TYPE: amino acid
        (D) TOPOLOGY: linear (xi) SEQUENCE DESCRIPTION: SEQ ID NO:56:

```
Gly Arg Gly Arg Val Glu Leu Lys Arg Ile Glu Asn Lys Ile Asn Arg
              5                  10                  15

Gln Val Thr Phe Ala Lys Arg Arg Asn Gly Leu Leu Lys Lys Ala Tyr
             20                  25                  30

Glu Leu Ser Val Leu Cys Asp Ala Glu Val Ala Leu Ile Ile Phe Ser
             35                  40                  45

Ser Arg Gly Lys Leu Tyr Glu Phe
 50                  55
```

(2) INFORMATION FOR SEQ ID NO: 57:

(i) SEQUENCE CHARACTERISTICS:
    (A) LENGTH: 40 amino acid residues
    (B) TYPE: amino acid
    (D) TOPOLOGY: linear (xi) SEQUENCE DESCRIPTION: SEQ ID NO:57:

Cys Ser Gly Ser Ser Ser Met Leu Lys Thr Leu Glu Glu Arg Tyr Gln
                        5                    10                15

Lys Cys Asn Tyr Asn Ala Pro Glu Ser Asn Asn Ser Ala Ala Glu Glu
      20                    25                  30

Leu Glu Ser Ser Tyr Gln Trp Ser
      35                  40

(2) INFORMATION FOR SEQ ID NO: 58:

(i) SEQUENCE CHARACTERISTICS:
        (A) LENGTH: 36 amino acid residues
        (B) TYPE: amino acid
        (D) TOPOLOGY: linear (xi) SEQUENCE DESCRIPTION: SEQ ID NO:58:

Cys Ser Ser Ser Ser Met Leu Lys Thr Leu Glu Arg Tyr Gln Lys Cys
                        5                    10                15

Asn Tyr Gly Ala Pro Glu Thr Asn Ile Ser Thr Arg Glu Ala Leu Glu
      20                    25                  30

Ile Ser Ser Gln
      35

(2) INFORMATION FOR SEQ ID NO: 59:

(i) SEQUENCE CHARACTERISTICS:
        (A) LENGTH: 36 amino acid residues
        (B) TYPE: amino acid
        (D) TOPOLOGY: linear (xi) SEQUENCE DESCRIPTION: SEQ ID NO:59:

Cys Ser Ser Ser Ser Met Leu Lys Thr Leu Glu Arg Tyr Gln Lys Cys
                        5                    10                15

Asn Tyr Gly Ala Pro Glu Pro Asn Ile Ser Thr Arg Glu Ala Leu Glu
      20                    25                  30

Ile Ser Ser Gln
      35

(2) INFORMATION FOR SEQ ID NO: 60:

(i) SEQUENCE CHARACTERISTICS:
        (A) LENGTH: 35 amino acid residues
        (B) TYPE: amino acid
        (D) TOPOLOGY: linear (xi) SEQUENCE DESCRIPTION: SEQ ID NO:60:

Cys Ser Thr Ser Asn Met Leu Lys Thr Leu Glu Arg Tyr Gln Lys Cys
                        5                    10                15

Ser Tyr Gly Ser Ile Glu Val Asn Asn Lys Pro Ala Lys Glu Leu Glu
      20                    25                  30

Asn Ser Tyr
      35

(2) INFORMATION FOR SEQ ID NO: 61:

(i) SEQUENCE CHARACTERISTICS:
        (A) LENGTH: 35 amino acid residues
        (B) TYPE: amino acid (D) TOPOLOGY: linear (xi) SEQUENCE DESCRIPTION: SEQ ID NO:61:

Cys Ser Ser Ser Asn Met Leu Lys Thr Leu Asp Arg Tyr Gln Lys Cys
                5                  10                  15
Ser Tyr Gly Ser Ile Glu Val Asn Asn Lys Pro Ala Lys Glu Leu Glu
             20                  25                  30
Asn Ser Tyr
         35

(2) INFORMATION FOR SEQ ID NO: 62:

(i) SEQUENCE CHARACTERISTICS:
        (A) LENGTH: 34 amino acid residues
        (B) TYPE: amino acid
        (D) TOPOLOGY: linear (xi) SEQUENCE DESCRIPTION: SEQ ID NO:62:

Cys Ser Ser Thr Ser Met Leu Lys Thr Leu Glu Lys Tyr Gln Lys Cys
                5                  10                  15
Asn Phe Gly Ser Pro Glu Ser Thr Ile Ile Ser Arg Glu Thr Gln Ser
             20                  25                  30
Ser Gln (2) INFORMATION FOR SEQ ID NO: 63:

(i) SEQUENCE CHARACTERISTICS:
        (A) LENGTH: 33 amino acid residues
        (B) TYPE: amino acid
        (D) TOPOLOGY: linear (xi) SEQUENCE DESCRIPTION: SEQ ID NO:63:

Gly Ser Ala Gly Ile Thr Lys Thr Leu Glu Arg Tyr Gln His Cys Cys
                5                  10                  15
Tyr Asn Ala Gln Asp Ser Asn Gly Ala Leu Ser Glu Thr Gln Ser Trp
             20                  25                  30
Tyr (2) INFORMATION FOR SEQ ID NO: 64:

(i) SEQUENCE CHARACTERISTICS:
        (A) LENGTH: 34 amino acid residues
        (B) TYPE: amino acid
        (D) TOPOLOGY: linear (xi) SEQUENCE DESCRIPTION: SEQ ID NO:64:

Gly Ser Ala Gly Val Thr Lys Thr Leu Glu Arg Tyr Gln His Cys Cys
                5                  10                  15
Tyr Asn Ala Gln Asp Ser Asn Asn Ser Ala Leu Ser Glu Ser Gln Ser
             20                  25                  30
Trp Tyr (2) INFORMATION FOR SEQ ID NO: 65:

(i) SEQUENCE CHARACTERISTICS:
        (A) LENGTH: 33 amino acid residues
        (B) TYPE: amino acid
        (D) TOPOLOGY: linear (xi) SEQUENCE DESCRIPTION: SEQ ID NO:65:

Gly Ser Val Gly Ile Glu Ser Thr Ile Glu Arg Tyr Asn Arg Cys Tyr
                5                  10                  15

```
Asn Cys Ser Leu Ser Asn Asn Lys Pro Glu Glu Thr Thr Gln Ser Trp
            20                  25                  30
Cys
```

(2) INFORMATION FOR SEQ ID NO: 66:

(i) SEQUENCE CHARACTERISTICS:
        (A) LENGTH: 35 amino acid residues
        (B) TYPE: amino acid
        (D) TOPOLOGY: linear (xi) SEQUENCE DESCRIPTION: SEQ ID NO:66:

```
Ser Thr Asp Ser Cys Met Glu Lys Ile Leu Glu Arg Tyr Glu Arg Tyr
                 5                  10                  15
Ser Tyr Ala Glu Arg Gln Leu Ile Ala Pro Glu Ser Asp Val Asn Thr
            20                  25                  30
Asn Trp Ser
        35
```

(2) INFORMATION FOR SEQ ID NO: 67:

(i) SEQUENCE CHARACTERISTICS:
        (A) LENGTH: 30 amino acid residues
        (B) TYPE: amino acid
        (D) TOPOLOGY: linear (xi) SEQUENCE DESCRIPTION: SEQ ID NO:67:

```
Ile Ser Pro Asn Thr Thr Thr Lys Glu Ile Val Asp Leu Tyr Gln Thr
                 5                  10                  15
Ile Ser Asp Val Asp Val Trp Ala Thr Gln Tyr Glu Arg Met
            20                  25                  30
```

(2) INFORMATION FOR SEQ ID NO: 68:

(i) SEQUENCE CHARACTERISTICS:
        (A) LENGTH: 29 amino acid residues
        (B) TYPE: amino acid
        (D) TOPOLOGY: linear (xi) SEQUENCE DESCRIPTION: SEQ ID NO:68:

```
Pro Ser Met Asp Leu Gly Ala Met Leu Asp Gln Tyr Gln Lys Leu Ser
                 5                  10                  15
Gly Lys Lys Leu Trp Asp Ala Lys His Glu Asn Leu Ser
            20                  25
```

(2) INFORMATION FOR SEQ ID NO: 69:

(i) SEQUENCE CHARACTERISTICS:
        (A) LENGTH: 34 amino acid residues
        (B) TYPE: amino acid
        (D) TOPOLOGY: linear (xi) SEQUENCE DESCRIPTION: SEQ ID NO:69:

```
Ser Asn Asn Ser Val Lys Gly Thr Ile Glu Arg Tyr Lys Lys Ala Ile
                 5                  10                  15
Ser Asp Asn Ser Asn Thr Gly Ser Val Ala Glu Ile Asn Ala Gln Tyr
            20                  25                  30
Tyr Gln
```

(2) INFORMATION FOR SEQ ID NO: 70:

(i) SEQUENCE CHARACTERISTICS:
        (A) LENGTH: 66 amino acid residues
        (B) TYPE: amino acid -continued (D) TOPOLOGY: linear (xi) SEQUENCE DESCRIPTION: SEQ ID NO:70:

```
Gln Glu Thr Tyr Leu Lys Leu Lys Ala Arg Tyr Glu Ala Leu Gln Arg
                 5                   10                  15

Thr Gln Arg Asn Leu Leu Gly Glu Asp Leu Gly Pro Leu Ser Ser Lys
             20                  25                  30

Glu Leu Glu Gln Leu Glu Arg Gln Leu Glu Ala Ser Leu Lys Gln Ile
         35                  40                  45

Arg Ser Arg Lys Thr Gln Leu Met Leu Asp Gln Leu Glu Asp Leu Gln
     50                  55                  60

Arg Lys
65
```

What is claimed is:

1. An isolated nucleic acid molecule encoding a protein comprising an amino acid sequence selected from the group consisting of:
   a) a sequence as shown in SEQ ID NO:13; and
   b) a sequence that differs from the sequence as shown in SEQ ID NO:13 by one or more conservative amino acid substitutions, wherein said isolated nucleic acid molecule comprises at least 100 contiguous nucleotides of SEQ ID NO:12.

2. A recombinant nucleic acid molecule comprising a promoter sequence operably linked to the nucleic acid molecule of claim 1.

3. A cell transformed with the recombinant nucleic acid molecule of claim 2.

4. A transgenic plant comprising the recombinant nucleic acid molecule of claim 2.

5. An isolated nucleic acid molecule encoding a protein comprising an amino acid sequence selected from the group consisting of:
   a) a sequence as shown in SEQ ID NO:55; and
   b) a sequence that differs from the sequence as shown in SEQ ID NO:55 by one or more conservative amino acid substitutions, wherein expression of the protein in a transgenic plant causes the transgenic plant to exhibit diminished apical dominance and early flowering compared to a nontransgenic control plant.

6. A recombinant nucleic acid molecule comprising a promoter sequence operably linked to the nucleic acid molecule of claim 5.

7. A cell transformed with the recombinant nucleic acid molecule of claim 6.

8. A transgenic plant comprising the recombinant nucleic acid molecule of claim 6.

9. An isolated nucleic acid molecule encoding a protein comprising an amino acid sequence selected from the group consisting of:
   a) a sequence as shown in SEQ ID NO:15; and
   b) a sequence that differs from the sequence as shown in SEQ ID NO:15 by one or more conservative amino acid substitutions, wherein said isolated nucleic acid molecule comprises at least 50 contiguous nucleotides of SEQ ID NO:14.

10. A recombinant nucleic acid molecule comprising a promoter sequence operably linked to the nucleic acid molecule of claim 9.

11. A cell transformed with the recombinant nucleic acid molecule of claim 10.

12. A transgenic plant comprising the recombinant nucleic acid molecule of claim 10.

13. An isolated nucleic acid molecule encoding a protein comprising an amino acid sequence selected from the group consisting of:
   a) a sequence as shown in SEQ ID NO:17; and
   b) a sequence that differs from the sequence as shown in SEQ ID NO:17 by one or more conservative amino acid substitutions, wherein said isolated nucleic acid molecule comprises at least 50 contiguous nucleotides of SEQ ID NO:16.

14. A recombinant nucleic acid molecule comprising a promoter sequence operably linked to the nucleic acid molecule of claim 13.

15. A cell transformed with the recombinant nucleic acid molecule of claim 14.

16. A transgenic plant comprising the recombinant nucleic acid molecule of claim 14.

17. An isolated nucleic acid molecule comprising at least 50 consecutive nucleotides of the sequence as shown in SEQ ID NO:54.

18. A recombinant nucleic acid molecule comprising a promoter sequence operably linked to the nucleic acid molecule of claim 17.

19. A cell transformed with the recombinant nucleic acid molecule of claim 18.

20. A transgenic plant comprising the recombinant nucleic acid molecule of claim 18.

21. An isolated nucleic acid molecule comprising at least 100 consecutive nucleotides of the sequence as shown in SEQ ID NO:12.

22. A recombinant nucleic acid molecule comprising a promoter sequence operably linked to the nucleic acid molecule of claim 21.

23. A cell transformed with the recombinant nucleic acid molecule of claim 22.

24. A transgenic plant comprising the recombinant nucleic acid molecule of claim 22.

25. An isolated nucleic acid molecule comprising at least 100 consecutive nucleotides that hybridizes with a portion of a nucleotide sequence as shown in SEQ ID NO:54, the portion not including MADS-box and K-box regions, the hybridization being under hybridization wash conditions of 0.1× SSC and 0.1% SDS at 65° C.

26. A recombinant nucleic acid molecule comprising a promoter sequence operably linked to the nucleic acid molecule of claim 25.

27. A cell transformed with the recombinant nucleic acid molecule of claim 26.

28. A transgenic plant comprising the recombinant nucleic acid molecule of claim 26.

29. An isolated nucleic acid comprising at least 100 consecutive nucleotides having at least 80% sequence identity with a portion of a nucleotide sequence as shown in SEQ ID NO:54, the portion not including MADS-box and K-box regions.

30. A recombinant nucleic acid molecule comprising a promoter sequence operably linked to the nucleic acid molecule of claim 29.

31. A cell transformed with the recombinant nucleic acid molecule of claim 30.

32. A transgenic plant comprising the recombinant nucleic acid molecule of claim 30.

33. An isolated nucleic acid molecule comprising a sequence selected from the group consisting of:

a nucleic acid sequence as shown in SEQ ID NO:12;

a nucleic acid sequence as shown in SEQ ID NO:54;

a nucleic acid sequence as shown in SEQ ID NO:14; and a nucleic acid sequence as shown in SEQ ID NO:16.

* * * * *

UNITED STATES PATENT AND TRADEMARK OFFICE
CERTIFICATE OF CORRECTION

PATENT NO. : 5,990,386
DATED : November 23, 1999
INVENTOR(S) : Gynheung An

Page 1 of 3

It is certified that error appears in the above-identified patent and that said Letters Patent is hereby corrected as shown below:

Title page,
In the Inventor name, "Gynhueng An" should read -- Gynheung An --.

Column 2,
Line 7, "21:4769-4776 1993) should read -- 21:4769-4776, 1993) --.
Line 16, "Theiβen" should read -- Theißen --.
Line 36, "Theiβen" should read -- Theißen --.

Column 3,
Line 21, "gene (SEQ ID NO:16) gene" should read -- gene (SEQ ID NO:16) --.
Lines 39-40, "SEQ ID:2" should read -- SEQ ID NO:2 --.
Line 46, "OsMADSI (residues 2-57) (SEQ ID NO:3" should read -- OsMADSI cDNA (residues 2-57) (SEQ ID NO:3) --.
Line 54, "SEQ ID NO:11)" should read -- SEQ ID NO:11). --

Column 4,
Line 28, "end]" should read -- end) --.

Column 6,
Line 38, delete the word "for".
Line 39, "eliminated" should read -- eliminated. --.

Column 7,
Line 49, delete the word "an".
Line 64, "fragment" should read -- A "fragment" --.

Column 8,
Line 67, "et al[]" should read -- et al. --.

Column 11,
Line 58, "Polvpeptide" should read -- Polypeptide --.
Line 58, "homoloqy" should read -- homology --.

Column 12,
Line 1, delete the close parenthesis.

Column 14,
Line 46, "template" should read -- template. --.

UNITED STATES PATENT AND TRADEMARK OFFICE
CERTIFICATE OF CORRECTION

PATENT NO. : 5,990,386
DATED : November 23, 1999
INVENTOR(S) : Gynheung An

It is certified that error appears in the above-identified patent and that said Letters Patent is hereby corrected as shown below:

Column 20,
Line 46, ":179-181 1983)" should read -- :179-181, 1983) --.

Column 22,
Line 32, "OsMADS6" should read -- OsMADS7 --.
Line 38, delete "(FIG. 7)"
Line 56, "FIG. 7" should read -- FIG. 7D --.

Column 23,
Line 17, "patter" should read -- pattern --.
Line 21, "Os[]MADS" should read -- OsMADS --.
Line 34, "OsMADSB" should read -- OsMADS8 --.
Line 64, "growth" should read -- growth. --.

Column 24,
Lines 10-11, no new paragraph.
Line 21, "that" should read -- than --.
Line 34, "Theiβen" should read -- Theißen --.
Line 52, OsMADS[]i" should read -- OsMADS1 --.

Column 25,
Line 43, "family" should read -- family. --.

Column 26,
Line 9, "105" should read -- $10^5$ --.
Line 10, "32P" should be -- $^{32}P$ --.
Line 28, "0.2w" should read -- 0.2% --.
Line 43, "0.1" should read -- 0.1% --.

Column 27,
Line 57, delete "with".

UNITED STATES PATENT AND TRADEMARK OFFICE
CERTIFICATE OF CORRECTION

PATENT NO. : 5,990,386
DATED : November 23, 1999
INVENTOR(S) : Gynheung An

It is certified that error appears in the above-identified patent and that said Letters Patent is hereby corrected as shown below:

Column 28,
Line 15, "Theiβen" should read -- Theißen --.

Signed and Sealed this

Twenty-second Day of January, 2002

Attest:

JAMES E. ROGAN
Attesting Officer
Director of the United States Patent and Trademark Office